US011904322B2

(12) United States Patent
Sosa et al.

(10) Patent No.: US 11,904,322 B2
(45) Date of Patent: Feb. 20, 2024

(54) METHODS AND SYSTEMS FOR NUCLEIC ACID ANALYSIS

(71) Applicant: Ultima Genomics, Inc., Newark, CA (US)

(72) Inventors: Jose Martin Sosa, Newark, CA (US); Joseph Anthony, Newark, CA (US); Nathan Beckett, Newark, CA (US); Gilad Almogy, Newark, CA (US); Chandan Shee, Newark, CA (US); Phillip You Fai Lee, Newark, CA (US); Yuto Watanabe, Newark, CA (US)

(73) Assignee: ULTIMA GENOMICS, INC., Fremont, CA (US)

( * ) Notice: Subject to any disclaimer, the term of this patent is extended or adjusted under 35 U.S.C. 154(b) by 0 days.

(21) Appl. No.: 17/673,444

(22) Filed: Feb. 16, 2022

(65) Prior Publication Data

US 2022/0168745 A1 Jun. 2, 2022

Related U.S. Application Data

(63) Continuation of application No. PCT/US2021/040200, filed on Jul. 1, 2021.
(Continued)

(51) Int. Cl.
*B01L 7/00* (2006.01)
*B01L 3/00* (2006.01)
(Continued)

(52) U.S. Cl.
CPC .................. *B01L 7/52* (2013.01); *B01L 3/508* (2013.01); *B01L 2200/0647* (2013.01);
(Continued)

(58) Field of Classification Search
CPC ....... B01L 2200/0647; B01L 2300/042; B01L 2300/0829; B01L 2300/0883;
(Continued)

(56) References Cited

U.S. PATENT DOCUMENTS 8,715,934 B2   5/2014   Diehl et al.
9,260,751 B2   2/2016   Diehl et al.
(Continued)

FOREIGN PATENT DOCUMENTS

EP          2912196 B1     8/2018
WO     WO-2007149432 A2   12/2007
(Continued)

OTHER PUBLICATIONS

Dumousseau, et al. MELTING, a flexible platform to predict the melting temperatures of nucleic acids. BMC Bioinformatics 13, 101 (2012). https://doi.org/10.1186/1471-2105-13-101.
(Continued)

*Primary Examiner* — Lydia Edwards
(74) *Attorney, Agent, or Firm* — Wilson Sonsini Goodrich & Rosati

(57) ABSTRACT

The present disclosure provides methods and processes for increasing the efficiency and accuracy of nucleic acid sequencing using techniques such as polymerase chain reaction (PCR). Methods and systems provided herein may facilitate performing reactions such as emulsion PCR (ePCR) on samples comprising nucleic acids and beads. The methods provided herein may provide a higher throughput compared to existing technologies.

18 Claims, 23 Drawing Sheets

Related U.S. Application Data

(60) Provisional application No. 63/047,763, filed on Jul. 2, 2020.

(51) Int. Cl.
  *B01L 99/00* (2010.01)
  *C12Q 1/686* (2018.01)

(52) U.S. Cl.
  CPC .................. *B01L 2300/1805* (2013.01); *B01L 2400/0415* (2013.01); *C12Q 1/686* (2013.01)

(58) Field of Classification Search
  CPC ..... B01L 2300/1805; B01L 2400/0415; B01L 3/502761; B01L 3/508; B01L 7/52; B03C 1/30; C12N 13/00; C12Q 1/686
  See application file for complete search history.

(56) References Cited

U.S. PATENT DOCUMENTS

| | | |
|---|---|---|
| 9,803,226 B2 | 10/2017 | Diehl et al. |
| 11,118,223 B2 | 9/2021 | Almogy et al. |
| D956,263 S | 6/2022 | Beckett et al. |
| 2004/0248087 A1 | 12/2004 | Burg et al. |
| 2006/0081462 A1 | 4/2006 | Goto et al. |
| 2008/0179555 A1 | 7/2008 | Landers et al. |
| 2011/0072887 A1 | 3/2011 | Oki |
| 2015/0258544 A1* | 9/2015 | Stern ................ B01L 3/502746 506/40 |
| 2019/0088517 A1 | 3/2019 | Kosakai et al. |

FOREIGN PATENT DOCUMENTS

| | | |
|---|---|---|
| WO | WO-2007149432 A3 | 12/2008 |
| WO | WO-2014068407 A2 | 5/2014 |
| WO | WO-2020118172 A1 | 6/2020 |
| WO | WO-2022006468 A1 | 1/2022 |

OTHER PUBLICATIONS

PCT/US2021/040200 International Search Report and Written Opinion dated Dec. 7, 2021.

Whitesides, George M. The origins and the future of microfluidics. Nature vol. 442,7101 (2006): 368-73. doi:10.1038/nature05058.

\* cited by examiner

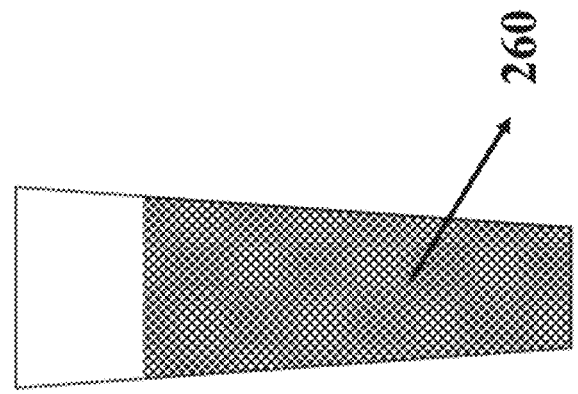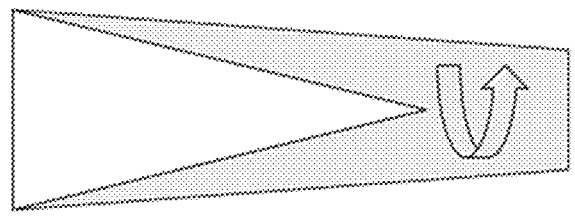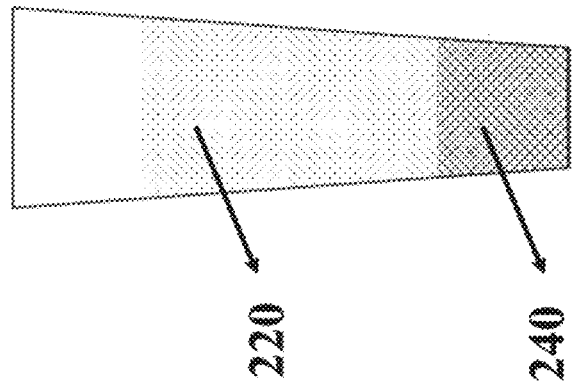
FIG. 2

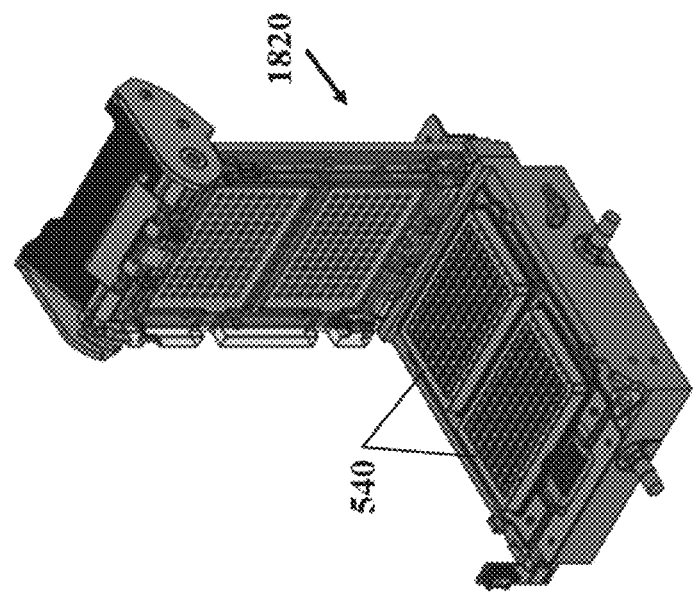
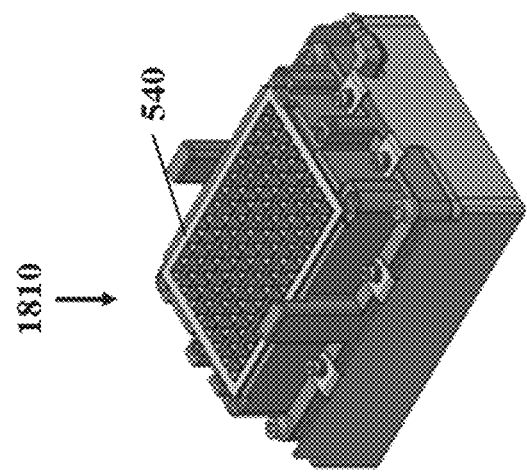
FIG. 18

METHODS AND SYSTEMS FOR NUCLEIC ACID ANALYSIS

CROSS-REFERENCE

This application is a continuation of International Application Serial No. PCT/US2021/040200, filed Jul. 1, 2021, which claims priority to U.S. Provisional Patent Application No. 63/047,763, filed Jul. 2, 2020, which is entirely incorporated herein by reference for all purposes.

BACKGROUND

Advances in the study of biological molecules have been led, in part, by improvements in technologies used to characterize molecules and/or their biological reactions. In particular, the study of nucleic acids has benefited from developing technologies used for sequence analysis. Sequencing of nucleic acids has various applications in the fields of molecular biology and medicine (e.g., diagnosis and treatment monitoring). Nucleic acid sequencing may provide information that may be used to diagnose a certain condition in a subject and/or tailor a treatment plan. Sequencing is widely used for molecular biology applications, including vector designs, gene therapy, vaccine design, industrial strain design and verification.

SUMMARY

In many cases, the available methods for analyzing nucleic acid molecules may be limited to relatively small sample sizes, low throughput, and/or time consuming. Recognized herein is a need for methods and systems for high-throughput nucleic analysis to facilitate analyzing larger sample sizes in a given period of time. The methods, processes, and compositions provided herein can facilitate increasing the efficiency, accuracy, throughput, and/or speed of nucleic acid analysis methods such as polymerase chain reaction (PCR) (e.g., emulsion PCR).

The present disclosure provides methods and systems for analyzing and/or processing nucleic acid molecules (e.g., those found in biological samples) with high accuracy, sensitivity, efficient reagent usage, and high throughput. The methods and systems provided herein may facilitate processing and/or analyzing larger volumes of sample within a given time. The methods and systems provided herein may facilitate processing and/or analyzing a given volume of sample at a greater speed or rate, and/or at higher efficiency, and therefore at a shorter period of time.

In an aspect, the present disclosure provides a system, comprising: a container having a volume of at most 1 liter (L). The container may comprise a first surface and a second surface substantially opposite from the first surface. The system further comprises a first electrostatic block in electrical communication with the first surface, wherein the first electrostatic block comprises one or more first electrodes. The system further comprises a second electrostatic block in electrical communication with the second surface. The second electrostatic block may comprise one or more second electrodes. The system further comprises a thermal block in thermal communication with the container; and a controller operatively coupled to the first electrostatic block, said second electrostatic block, and said thermal block, and configured to: simultaneously (i) activate said first electrostatic block and said second electrostatic block to subject an electrode of said first electrostatic block or said second electrostatic block to alternate between positive and neutralizing ion at a predetermined frequency and (ii) using said thermal block, change or maintain a temperature of a content of said container at a predetermined temperature or temperature range.

In some embodiments, the container has a volume of at most 500 milliliters (mL). In some embodiments, the container has a volume of at most 300 mL. In some embodiments, the container has a volume of at most 200 mL. In some embodiments, the container has a volume of at most 100 mL.

In some embodiments, the predetermined frequency is at least 30 Hertz (Hz). In some embodiments, the predetermined frequency is at least 50 Hz. In some embodiments, the predetermined frequency is at least 60 Hz. In some embodiments, the controller is configured to activate the first electrostatic block and the second electrostatic block to subject each electrode of the first electrostatic block or the second electrostatic block to alternate between a positive and neutralizing ion at the predetermined frequency.

In some embodiments, the predetermined temperature or temperature range is at least 30 degrees Celsius (° C.). In some embodiments, the predetermined temperature or temperature range is at least 50 degrees Celsius (° C.). In some embodiments, the predetermined temperature or temperature range is at least 60 degrees Celsius (° C.). In some embodiments, the predetermined temperature or temperature range is from about 70 degrees Celsius (° C.) to about 100 degrees Celsius (° C.). In some embodiments, the predetermined temperature or temperature range is from about 75 degrees Celsius (° C.) to about 95 degrees Celsius (° C.). In some embodiments, the predetermined temperature or temperature range is from about 80 degrees Celsius (° C.) to about 90 degrees Celsius (° C.).

In some embodiments, the one or more first electrodes comprises at least 5 electrodes. In some embodiments, the one or more first electrodes comprises at least 10 electrodes. In some embodiments, the one or more first electrodes comprises at least 12 electrodes. In some embodiments, the at least two of the one or more first electrodes are spaced at least ⅛ inch apart. In some embodiments, the at least two of the one or more first electrodes are spaced at least ⅜ inch apart.

In some embodiments, the container has a third surface and a fourth surface different from the first surface and the second surface. The third surface may be substantially opposite the fourth surface, and the thermal block may be in thermal communication with the third surface or fourth surface.

In some embodiments, the system further comprises a second thermal block in thermal communication with the third surface, and the thermal block is in thermal communication with the fourth surface.

In an aspect, the present disclosure provides a system, comprising: a first fluid source container, wherein the first fluid source container is configured to maintain fluid within at a first temperature or temperature range. The system further comprises a second fluid source container, wherein the second fluid source container is configured to maintain fluid within at a second temperature or temperature range different from the first temperature or temperature range. The system further comprises a thermocycler comprising a plurality of fins and a fluid channel in thermal communication with the plurality of fins, wherein the fluid channel is fluidically connected to the first fluid source container and the second fluid source container, and the thermocycler is configured to receive a cartridge comprising a plurality of containers between at least a subset of the plurality of fins.

The system further comprises a controller operably coupled to the thermocycler, the first fluid source container, and the second fluid source container, wherein the controller is configured to, when the plurality of containers is received by the thermocycler, (i) subject a gap between the at least the subset of the plurality of fins and the plurality of containers to negative pressure, thereby creating a vacuum to decrease a distance of the gap, and (ii) subject fluid from the first fluid source container and the second fluid source container, in sequence, to flow through the fluid channel, thereby thermocycling a sample in the plurality of containers.

In some embodiments, the plurality of thermal fins comprise metal. In some embodiments, the plurality of thermal fins comprise aluminum. In some embodiments, the system comprises a lid configured to close the thermocycler. In some embodiments, the controller is operably coupled to the lid and configured to maintain the lid at a temperature or temperature threshold.

In some embodiments, the thermocycler further comprises a fluid channel in thermal communication with the plurality of fins, wherein the fluid channel is fluidically connected to a first fluid source container and a second fluid source container.

In some embodiments, the system further comprising the cartridge. In some embodiments, the cartridge comprises at least 50 containers. In some embodiments, the cartridge comprises at least 70 containers. In some embodiments, the cartridge comprises at least 80 containers. In some embodiments, the cartridge comprises at least 90 containers. In some embodiments, the cartridge comprises at least 100 containers. In some embodiments, the plurality of containers are a plurality of wells. In some embodiments, a container of the plurality of containers is configured to hold at least 1 milliliter (1 mL) of fluid.

In an aspect, the present disclosure provides a method of sample processing comprising: (a) providing (i) a thermocycler comprising a plurality of fins and a fluid channel in thermal communication with the plurality of fins, (ii) a first fluid source container, wherein the first fluid source container is configured to maintain fluid within at a first temperature or temperature range and (iii) a second fluid source container, wherein the second fluid source container is configured to maintain fluid within at a second temperature or temperature range different from the first temperature or temperature range, wherein the fluid channel is fluidically connected to the first fluid source container and the second fluid source container; (b) receiving a cartridge comprising a plurality of containers between at least a subset of the plurality of fins in the thermocycler, wherein a container of the plurality of containers comprises a sample; and (c) thermocycling the sample by (i) subjecting a gap between the at least the subset of the plurality of fins and the plurality of containers to negative pressure, thereby creating a vacuum to decrease a distance of the gap, and (ii) subjecting fluid from the first fluid source container and the second fluid source container, in sequence, to flow through the fluid channel.

In some embodiments, subsequent to (c), further comprising subjecting the sample to washing in a washing module operably coupled to the thermocycler. In some embodiments, the method further comprises, prior to the washing, receiving a second cartridge in the thermocycler, wherein the second cartridge comprises a second sample. In some embodiments, the method further comprises, during the washing of the sample in the washing module, subjecting the second sample to thermocycling in the thermocycler.

In some embodiments, the method further comprises, subsequent to washing of the sample, subjecting the sample to enrichment in an enrichment module operably coupled to the washing module. In some embodiments, the method further comprises, prior to the enrichment, receiving a third cartridge on the thermocycler, wherein the third cartridge comprises a third sample. In some embodiments, the method further comprises, during the enrichment of the sample, subjecting the third sample to thermocycling. In some embodiments, subsequent to the washing, the method further comprises subjecting the sample to enrichment in an enrichment module operably coupled to the washing module.

In some embodiments, the method further comprises, prior to the enrichment, receiving a second cartridge on the thermocycler, wherein the second cartridge comprises a second sample. In some embodiments, the method further comprises, during the enrichment of the sample, subjecting the second sample to thermocycling. In some embodiments, subsequent to the washing, the method further comprises incubating the sample at a predetermined temperature or a range thereof. In some embodiments, subsequent to the incubating, the method further comprises subjecting the sample to enrichment in an enrichment module. In some embodiments, further comprising, subsequent to (c), subjecting the sample to sequencing. In some embodiments, (b) comprises loading the cartridge by an operator. In some embodiments, (b) is automated In an aspect, provided herein is a system, comprising: a thermocycler comprising (i) a plurality of fins configured to receive a cartridge comprising a plurality of containers between at least a subset of the plurality of fins and (ii) a fluid channel in thermal communication with the plurality of fins. A cavity defined by at least two of the plurality of fins may be configured to receive therein at least two containers of the plurality of containers. The system may further comprise a controller operably coupled to the thermocycler. The controller may be configured to, when the plurality of containers is received by the thermocycler, (i) subject a gap between respective walls of the at least two containers and respective walls of the cavity to negative pressure, thereby creating a vacuum to decrease a distance of the gap, and (ii) subject fluid to flow through the fluid channel, thereby thermocycling a sample in the plurality of containers.

In some embodiments, the plurality of thermal fins may comprise metal. In some embodiments, the plurality of thermal fins comprise aluminum. In some embodiments, the system comprises a lid configured to enclose and/or cover the thermocycler. In some embodiments, the controller is operably coupled to the lid and configured to maintain the lid at a temperature or temperature threshold.

In some embodiments, the system further comprises the cartridge. In some embodiments, the plurality of containers is a plurality of wells. In some embodiments, a container of plurality of containers is configured to hold at least 1 milliliter (1 mL) of fluid. In some embodiments, the cavity is configured to receive therein at least four containers of the plurality of containers. In some embodiments, the cavity is configured to receive therein at least eight containers of the plurality of containers. In some embodiments, the cavity is configured to receive therein at least twelve containers of the plurality of containers. In some embodiments, a plurality of cavities is defined by the plurality of fins, wherein each cavity of the plurality of cavities is configured to receive at least two containers of the plurality of containers. In some embodiments, the plurality of cavities is disposed as an array of substantially parallel lanes of cavities. In some embodiments the cavity comprises one or more features configured to guide individual containers of the at least two containers within said cavity. In some embodiments, the one or more features are coupled to one or more walls of the plurality of fins. In some embodiments, the one or more features are integrated with one or more walls of the plurality of fins. In some embodiments, the cavity comprises a first substantially planar wall, and wherein a container of the at least two containers comprise a second substantially planar wall configured to interface the first substantially planar wall.

In an aspect, provided herein is a method of sample processing comprising: (a) providing a thermocycler comprising (i) a plurality of fins configured to receive a cartridge comprising a plurality of containers between at least a subset of the plurality of fins and (ii) a fluid channel in thermal communication with the plurality of fins, wherein a cavity defined by at least two of the plurality of fins is configured to receive therein at least two containers of the plurality of containers; (b) receiving a cartridge comprising a plurality of containers between at least a subset of the plurality of fins in the thermocycler, wherein a container of the plurality of containers comprises a sample; and (c) thermocycling the sample by (i) subjecting a gap between respective walls of the at least two containers and respective walls of the cavity to negative pressure, thereby creating a vacuum to decrease a distance of the gap, and (ii) subjecting fluid to flow through the fluid channel, thereby thermocycling a sample in the plurality of containers.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows an example method of emulsion formation.

FIG. 18 shows an additional system or platform according to the methods of the present disclosure.

DETAILED DESCRIPTION

Figure 1:
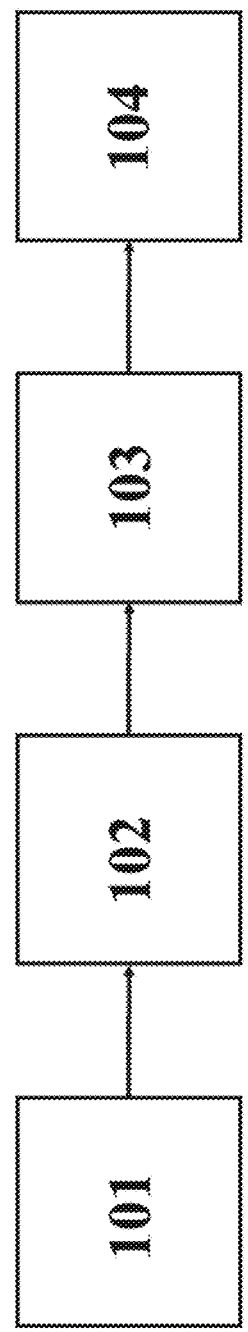
FIG. 1 shows an example workflow for performing the methods of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

Ranges may be expressed herein as from "about" one particular value, and/or to "about" another particular value. The terms "about" and "approximately" shall generally mean an acceptable degree of error or variation for a given value or range of values, such as, for example, a degree of error or variation that is within 20 percent (%), within 15%, within 10%, or within 5% of a given value or range of values.

The term "at least partially" as used herein, generally refers to any fraction of a whole amount. For example, "at least partially" may refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 99.9% of a whole amount.

The term "amplification," as used herein, generally refers to the production of one or more copies of a nucleic acid molecule or an extension product (e.g., a product of a primer extension reaction on the nucleic acid molecule). Amplification of a nucleic acid molecule may yield a single strand hybridized to the nucleic acid molecule, or multiple copies of the nucleic acid molecule or complement thereof. An amplicon can be a single-stranded or double-stranded nucleic acid molecule that is generated by an amplification procedure from a starting template nucleic acid molecule. The amplicon may comprise a nucleic acid strand, of which at least a portion may be substantially identical or substantially complementary to at least a portion of the starting template. Where the starting template is a double-stranded nucleic acid molecule, an amplicon may comprise a nucleic acid strand that is substantially identical to at least a portion of one strand and is substantially complementary to at least a portion of either strand. The amplicon can be single-stranded or double-stranded irrespective of whether the initial template is single-stranded or double-stranded. Amplification may yield a clonal population of nucleic acid molecules.

Amplification of a nucleic acid may be linear, exponential, or a combination thereof. Amplification may be emulsion based or may be non-emulsion based. Methods for amplification may comprise reverse transcription, primer extension, polymerase chain reaction (e.g., PCR), ligase chain reaction, helicase-dependent amplification, asymmetric amplification, rolling circle amplification, and multiple displacement amplification (MDA). Examples of amplification methods include polymerase chain reaction (PCR), variants of PCR (e.g., real-time PCR, allele-specific PCR, assembly PCR, asymmetric PCR, digital PCR, emulsion PCR (i.e., ePCR), dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). In some cases, amplification may be achieved with nested PCR, which may improve sensitivity of detecting amplified products. Paired-end adapters may be used for PCR amplification to increase accuracy and/or sensitivity (e.g., by increasing the signal-to-noise ratio) for analyzing a biological sample.

Amplification reactions may span for various time periods (e.g., several minutes or several hours). The time period over which amplification yields a detectable amount of amplified product indicative of the presence of a target nucleic acid molecule in a biological sample may vary depending upon the biological sample from which the target nucleic acid molecule may be obtained, the particular nucleic acid amplification reactions that may be conducted, the particular number of cycles of amplification reaction that may be performed, and the partitioning process conducted such as the generation of a plurality of droplets. Various detection and sequencing schemes may also permit varying detection limits. For example, amplification of a target nucleic acid molecule may yield a detectable amount of amplified product indicative of the presence of the target nucleic acid over a time period of 240 minutes or less; 120 minutes or less; 90 minutes or less; 60 minutes or less; 50 minutes or less; 45 minutes or less; 40 minutes or less; 35 minutes or less; 30 minutes or less; 25 minutes or less; 20 minutes or less; 15 minutes or less; 10 minutes or less; or 5 minutes or less. Alternatively, the time period may be greater than 240 minutes or more. In some cases, a single copy or complement of a nucleic acid molecule may be detectable (e.g., using a nucleic acid sequencing assay).

An amplification reaction of the present disclosure may be performed using a system configured to partition and/or process a library of templates and a plurality of beads into a plurality of partitions, such as a plurality of droplets and/or wells. For example, within a partition (e.g., a droplet), amplification yields a bead-nucleic acid molecule complex, in which a bead comprises a clonal population of nucleic acid molecules coupled thereto. Upon completion of an amplification process (e.g., after a certain duration of time and/or number of amplification cycles), the plurality of beads (e.g., the plurality of bead-nucleic acid molecule complexes) distributed amongst the plurality of partitions may be recovered, and the beads may be separated (e.g., magnetically separated) from the emulsion or mixture. Subsequently, the nucleic acid molecules or any derivatives thereof may be assayed or analyzed, such as by determining the nucleotide sequence in a sequencer. In some cases, only nucleic acid molecules (e.g., amplification products or derivatives thereof) coupled to beads are sequenced. In some cases, only nucleic acid molecules that are in monoclonal populations coupled to beads (substantially a single colony per bead) are sequenced.

The term "denaturation," as used herein, generally refers to separation of a double-stranded molecule (e.g., DNA) into single-stranded molecules. Denaturation may be complete or partial denaturation. In partial denaturation, a single-stranded region may form in a double-stranded molecule by denaturation of the two deoxyribonucleic acid (DNA) strands flanked by double-stranded regions in DNA. Denaturation may occur during an amplification reaction.

The term "clonal" or "colony," as used herein, generally refers to a population of nucleic acids for which a substantial portion (e.g., greater than 50%, 60%, 70%, 80%, 90%, 95%, or 99%) of its members have substantially identical sequences. Members of a clonal population of nucleic acid molecules may have sequence homology to one another. In some instances, such members may have sequence homology to a template nucleic acid molecule. In some instances, such members may have sequence homology to a complement of the template nucleic acid molecule (if single stranded). The members of the clonal population may be double stranded or single stranded. Members of a population may not be 100% identical or complementary because, e.g., "errors" may occur during the course of synthesis such that a minority of a given population may not have sequence homology with a majority of the population. For example, at least 50% of the members of a population may be substantially identical to each other or to a reference nucleic acid molecule (i.e., a molecule of defined sequence used as a basis for a sequence comparison). At least 60%, at least 70%, at least 80%, at least 90%, at least 95%, at least 99%, or more of the members of a population may be substantially identical to the reference nucleic acid molecule. Two molecules may be considered substantially identical (or homologous) if the percent identity between the two molecules is at least 60%, 70%, 75%, 80%, 85%, 90%, 95%, 98%, 99%, 99.9% or greater. Two molecules may be considered substantially complementary if the percent complementarity between the two molecules is at least 60%, 70%, 75%, 80%, 85%, 90%, 95%, 98%, 99%, 99.9% or greater. A low or insubstantial level of mixing of non-homologous nucleic acids may occur, and thus a clonal population may contain a minority of diverse nucleic acids (e.g., less than 30%, e.g., less than 10%).

The term "% sequence identity" may be used interchangeably herein with the term "% identity" and may refer to the level of nucleotide sequence identity between two or more nucleotide sequences, when aligned using a sequence alignment program. As used herein, 80% identity may be the same thing as 80% sequence identity determined by a defined algorithm and means that a given sequence is at least 80% identical to another length of another sequence. The % identity may be selected from, e.g., at least 60%, at least 65%, at least 70%, at least 75%, at least 80%, at least 85%, at least 90%, at least 95%, or at least 99% or more sequence identity to a given sequence. The % identity may be in the range of, e.g., about 60% to about 70%, about 70% to about 80%, about 80% to about 85%, about 85% to about 90%, about 90% to about 95%, or about 95% to about 99%.

The terms "% sequence homology" or "percent sequence homology" or "percent sequence identity" may be used interchangeably herein with the terms "% homology," "% sequence identity," or "% identity" and may refer to the level of nucleotide sequence homology between two or more nucleotide sequences, when aligned using a sequence alignment program. For example, as used herein, 80% homology may be the same thing as 80% sequence homology determined by a defined algorithm, and accordingly a homologue of a given sequence has greater than 80% sequence homology over a length of the given sequence. The % homology may be selected from, e.g., at least 60%, at least 65%, at least 70%, at least 75%, at least 80%, at least 85%, at least 90%, at least 95%, or at least 99% or more sequence homology to a given sequence. The % homology may be in the range of, e.g., about 60% to about 70%, about 70% to about 80%, about 80% to about 85%, about 85% to about 90%, about 90% to about 95%, or about 95% to about 99%.

The term "complementary sequence," as used herein, generally refers to a sequence that hybridizes to another sequence. Hybridization between two single-stranded nucleic acid molecules may involve the formation of a double-stranded structure that is stable under certain conditions. Two single-stranded polynucleotides may be considered to be hybridized if they are bonded to each other by two or more sequentially adjacent base pairings. A substantial proportion of nucleotides in one strand of a double-stranded structure may undergo Watson-Crick base-pairing with a nucleoside on the other strand. Hybridization may also include the pairing of nucleoside analogs, such as deoxyinosine, nucleosides with 2-aminopurine bases, and the like, that may be employed to reduce the degeneracy of probes, whether or not such pairing involves formation of hydrogen bonds.

The term "polymerizing enzyme," as used herein, generally refers to a substance catalyzing a polymerization reaction. A polymerizing enzyme may be used to extend a nucleic acid primer paired with a template strand by incorporation of nucleotides or nucleotide analogs. A polymerizing enzyme may add a new strand of DNA by extending the 3' end of an existing nucleotide chain, adding new nucleotides matched to the template strand one at a time via the creation of phosphodiester bonds. A polymerizing enzyme may be a polymerase such as a nucleic acid polymerase. A polymerase may be naturally occurring or synthesized. A polymerase may have relatively high processivity, namely the capability of the polymerase to consecutively incorporate nucleotides into a nucleic acid template without releasing the nucleic acid template. A polymerizing enzyme may be a transcriptase. Examples of polymerases may comprise a DNA polymerase, an RNA polymerase, a thermostable polymerase, a wild-type polymerase, a modified polymerase, E. coli DNA polymerase I, T7 DNA polymerase, bacteriophage T4 DNA polymerase, 029 (phi29) DNA polymerase, Taq polymerase, Tth polymerase, Tli polymerase, Pfu polymerase, Pwo polymerase, VENT polymerase, DEEPVENT polymerase, EXTaq polymerase, LA-Taq polymerase, Sso polymerase, Poc polymerase, Pab polymerase, Mth polymerase, ES4 polymerase, Tru polymerase, Tac polymerase, Tne polymerase, Tma polymerase, Tea polymerase, Tih polymerase, Tfi polymerase, Platinum Taq polymerases, Tbr polymerase, Tfl polymerase, Pfutubo polymerase, Pyrobest polymerase, Pwo polymerase, KOD polymerase, Bst polymerase, Sac polymerase, Klenow fragment, polymerase with 3' to 5' exonuclease activity, and variants, modified products and derivatives thereof. A polymerase may be a single subunit polymerase.

The term "melting temperature" or "melting point," as used herein, generally refers to the temperature at which at least a portion of a strand of a nucleic acid molecule in a sample has separated from at least a portion of a complementary strand. The melting temperature may be the temperature at which a double-stranded nucleic acid molecule has partially or completely denatured. The melting temperature may refer to a temperature of a sequence among a plurality of sequences of a given nucleic acid molecule, or a temperature of the plurality of sequences. Different regions of a double-stranded nucleic acid molecule may have different melting temperatures. For example, a double-stranded nucleic acid molecule may include a first region having a first melting point and a second region having a second melting point that is higher than the first melting point. Accordingly, different regions of a double-stranded nucleic acid molecule may melt (e.g., partially denature) at different temperatures. The melting point of a nucleic acid molecule or a region thereof (e.g., a nucleic acid sequence) may be determined experimentally (e.g., via a melt analysis or other procedure) or may be estimated based upon the sequence and length of the nucleic acid molecule. For example, a software program such as MELTING may be used to estimate a melting temperature for a nucleic acid sequence (Dumousseau M, Rodriguez N, Juty N, Le Novère N, MELTING, a flexible platform to predict the melting temperatures of nucleic acids. BMC Bioinformatics. 2012 May 16; 13:101. doi: 10.1186/1471-2105-13-101). Accordingly, a melting point as described herein may be an estimated melting point. A true melting point of a nucleic acid sequence may vary based upon the sequences or lack thereof adjacent to the nucleic acid sequence of interest as well as other factors.

The term "nucleotide," as used herein, generally refers to a substance including a base (e.g., a nucleobase), sugar moiety, and phosphate moiety. A nucleotide may comprise a free base with attached phosphate groups. A substance including a base with three attached phosphate groups may be referred to as a nucleoside triphosphate. When a nucleotide is being added to a growing nucleic acid molecule strand, the formation of a phosphodiester bond between the proximal phosphate of the nucleotide to the growing chain may be accompanied by hydrolysis of a high-energy phosphate bond with release of the two distal phosphates as a pyrophosphate. The nucleotide may be naturally occurring or non-naturally occurring (e.g., a modified or engineered nucleotide).

The term "nucleotide analog," as used herein, may comprise a nucleotide that may or may not be a naturally occurring nucleotide. For example, a nucleotide analog may be derived from and/or include structural similarities to a canonical nucleotide such as adenine—(A), thymine—(T), cytosine—(C), uracil—(U), or guanine—(G) including nucleotide. A nucleotide analog may comprise one or more differences or modifications relative to a natural nucleotide. Examples of nucleotide analogs include inosine, diaminopurine, 5-fluorouracil, 5-bromouracil, 5-chlorouracil, 5-iodouracil, hypoxanthine, xanthine, deazaxanthine, deazaguanine, isocytosine, isoguanine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, ethynyl nucleotide bases, 1-propynyl nucleotide bases, azido nucleotide bases, phosphoroselenoate nucleic acids, and modified versions thereof (e.g., by oxidation, reduction, and/or addition of a substituent such as an alkyl, hydroxyalkyl, hydroxyl, or halogen moiety). Nucleic acid molecules (e.g., polynucleotides, double-stranded nucleic acid molecules, single-stranded nucleic acid molecules, primers, adapters, etc.) may be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety, or phosphate backbone. In some cases, a nucleotide may include a modification in its phosphate moiety, including a modification to a triphosphate moiety. Additional examples of modifications may comprise phosphate chains of greater length (e.g., a phosphate chain having, 4, 5, 6, 7, 8, 9, 10 or more phosphate moieties), modifications with thiol moieties (e.g., alpha-thio triphosphate and beta-thiotriphosphates), and modifications with selenium moieties (e.g., phosphoroselenoate nucleic acids). A nucleotide or nucleotide analog may comprise a sugar selected from the group consisting of ribose, deoxyribose, and modified versions thereof (e.g., by oxidation, reduction, and/or addition of a substituent such as an alkyl, hydroxyalkyl, hydroxyl, or halogen moiety). A nucleotide analog may also comprise a modified linker moiety (e.g., in lieu of a phosphate moiety). Nucleotide analogs may also contain amine-modified groups, such as aminoallyl-dUTP (aa-dUTP) and aminohexylacrylamide-dCTP (aha-dCTP) to allow covalent attachment of amine reactive moieties, such as N-hydroxysuccinimide esters (NHS). Alternatives to standard DNA base pairs or RNA base pairs in the oligonucleotides of the present disclosure may provide, for example, higher density in bits per cubic mm, higher safety (resistant to accidental or purposeful synthesis of natural toxins), easier discrimination in photo-programmed polymerases, and/or lower secondary structure. Nucleotide analogs may be capable of reacting or bonding with detectable moieties for nucleotide detection.

The term "support" or "substrate," as used herein, generally refers to any solid or semi-solid article on which reagents such as nucleic acid molecules may be immobilized. Nucleic acid molecules or other molecules may be synthesized, attached, ligated, or otherwise immobilized. Nucleic acid molecules may be immobilized on a substrate using any suitable method such as physical adsorption, by ionic or covalent bond formation, or combinations thereof. A substrate may be 2-dimensional (e.g., a planar 2D substrate) or 3-dimensional. In some cases, a substrate may be a component of a flow cell and/or may be included within or adapted to be received by a sequencing instrument. A substrate may include a polymer, a glass, or a metallic material. Examples of substrates include a membrane, a planar substrate, a microtiter plate, a bead (e.g., a magnetic bead), a filter, a test strip, a slide, a cover slip, and a test tube. A substrate may comprise organic polymers such as polystyrene, polyethylene, polypropylene, polyfluoroethylene, polyethyleneoxy, and polyacrylamide (e.g., polyacrylamide gel), as well as co-polymers and grafts thereof. A substrate may comprise latex or dextran. A substrate may also be inorganic, such as glass, silica, gold, controlled-pore-glass (CPG), or reverse-phase silica. The configuration of a support may be, for example, in the form of beads, spheres, particles, granules, a gel, a porous matrix, or a substrate. In some cases, a substrate may be a single solid or semi-solid article (e.g., a single particle), while in other cases a substrate may comprise a plurality of solid or semi-solid articles (e.g., a collection of particles). Substrates may be planar, substantially planar, or non-planar. Substrates may be porous or non-porous and may have swelling or non-swelling characteristics. A substrate may be shaped to comprise one or more wells, depressions, or other containers, vessels, features, or locations. A plurality of substrates may be configured in an array at various locations. A substrate may be addressable (e.g., for robotic delivery of reagents), or by detection approaches, such as scanning by laser illumination and confocal or deflective light gathering. For example, a substrate may be in optical and/or physical communication with a detector. Alternatively, a substrate may be physically separated from a detector by a distance. An amplification substrate (e.g., a bead) can be placed within or on another substrate (e.g., within a well of a second support).

As used herein, the term "bead" generally refers to a solid support, resin, gel (e.g., hydrogel), colloid, or particle of any shape and dimensions. A bead may comprise any suitable material such as glass or ceramic, one or more polymers, and/or metals. Examples of suitable polymers include nylon, polytetrafluoroethylene, polystyrene, polyacrylamide, agarose, cellulose, cellulose derivatives, or dextran. Examples of suitable metals include paramagnetic metals, such as iron. A bead may be magnetic or non-magnetic. For example, a bead may comprise one or more polymers bearing one or more magnetic labels. A magnetic bead may be manipulated (e.g., moved between locations or physically constrained to a given location, e.g., of a reaction vessel such as a flow cell chamber) using electromagnetic forces. A bead may have one or more different dimensions including a diameter. A dimension of the bead (e.g., the diameter of the bead) may be on an order of less than about 1 millimeters (mm), less than about 0.1 mm, less than about 0.01 mm, less than about 0.001 mm (or 1 micrometer ($\mu$m)), 0.1 $\mu$m, 0.01 $\mu$m, 0.001 $\mu$m (or 1 nanometer (nm)). Alternatively, a bead may have a dimension greater than about 1 mm. A bead may have a dimension from about 1 nm to about 100 nm, from about 1 μm to about 100 μm, or from about 1 mm to about 100 mm.

A collection of beads may comprise one or more beads having the same or different characteristics. For example, a first bead of a collection of beads may have a first diameter and a second bead of the collection of beads may have a second diameter. The first diameter may be the same or approximately the same as or different from the second diameter. Similarly, the first bead may have the same or a different shape and composition than a second bead. In an example, the first bead may comprise a first polymeric material and the second bead may comprise a second polymeric material. The first polymeric material may be the same or different as the second polymeric material. The first bead may comprise a first material, such as a first oligonucleotide (e.g., primer) coupled thereto, and a second bead may comprise a second material, such as a second oligonucleotide (e.g., primer) coupled thereto. The first and second oligonucleotides may be the same or different. For example, the first oligonucleotide (e.g., first primer) may have the same nucleic acid sequence as the second oligonucleotide (e.g., second primer) or a different nucleic acid sequence. The first and second oligonucleotides may have partially overlapping and partially different sequences. The oligonucleotides may comprise one or more functional sequences, such as identifying sequences (e.g., barcodes, sample-specific barcodes, molecule-specific barcodes, cell-specific barcodes, etc.), capture sequences, adapter sequences, primer sequences, random N-mer sequences, attachment sequences, spacer sequences, splint sequences, and the like. Nucleic acid sequences of oligonucleotides coupled to a bead may have any useful sequence of any useful base composition and length. In some cases, a nucleic acid sequence of an oligonucleotide coupled to a bead may comprise only canonical nucleotides, while in other cases, a nucleic acid sequence of an oligonucleotide coupled to a bead may comprise one or more nucleotide analogs. A nucleic acid sequence may comprise one or more labels or dyes, such as one or more fluorescent labels, dyes, magnetic labels, radiofrequency labels, or other tags. A nucleic acid sequence of an oligonucleotide coupled to a bead may comprise one or more additional features such as a replication block, cleavable base, or reversible terminator.

The term "sequencing," as used herein, generally refers to a process for generating or identifying a sequence of a biological molecule, such as a nucleic acid molecule. Such sequence may be a nucleic acid sequence, which may include a sequence of nucleic acid bases (e.g., nucleobases). Sequencing may be, for example, single molecule sequencing, sequencing by synthesis, sequencing by hybridization, or sequencing by ligation. Sequencing may be performed using template nucleic acid molecules immobilized on a support, such as a flow cell or one or more beads. A sequencing assay may yield one or more sequencing reads corresponding to one or more template nucleic acid molecules.

The term "read," as used herein, generally refers to a nucleic acid sequence, such as a sequencing read. A sequencing read may be an inferred sequence of nucleic acid bases (e.g., nucleotides) or base pairs obtained via a nucleic acid sequencing assay. A sequencing read may be generated by a nucleic acid sequencer, such as a massively parallel array sequencer (e.g., Illumina or Pacific Biosciences of California). A sequencing read may correspond to a portion, or in some cases all, of a genome of a subject. A sequencing read may be part of a collection of sequencing reads, which may be combined through, for example, alignment (e.g., to a reference genome), to yield a sequence of a genome of a subject.

The term "subject," as used herein, generally refers to an individual or entity from which a biological sample (e.g., a biological sample that is undergoing or will undergo processing or analysis) may be derived. A subject may be an animal (e.g., mammal or non-mammal) or plant. The subject may be a human, dog, cat, horse, pig, bird, non-human primate, simian, farm animal, companion animal, sport animal, or rodent. A subject may be a patient. The subject may have or be suspected of having a disease or disorder, such as cancer (e.g., breast cancer, colorectal cancer, brain cancer, leukemia, lung cancer, skin cancer, liver cancer, pancreatic cancer, lymphoma, esophageal cancer or cervical cancer) or an infectious disease. Alternatively or in addition, a subject may be known to have previously had a disease or disorder. The subject may have or be suspected of having a genetic disorder such as achondroplasia, alpha-1 antitrypsin deficiency, antiphospholipid syndrome, autism, autosomal dominant polycystic kidney disease, Charcot-Marie-tooth, cri du chat, Crohn's disease, cystic fibrosis, Dercum disease, down syndrome, Duane syndrome, Duchenne muscular dystrophy, factor V Leiden thrombophilia, familial hypercholesterolemia, familial Mediterranean fever, fragile x syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency, sickle cell disease, spinal muscular atrophy, Tay-Sachs, thalassemia, trimethylaminuria, Turner syndrome, Velo-Cardio-Facial Syndrome (VCFS), WAGR syndrome, or Wilson disease. A subject may be undergoing treatment for a disease or disorder. A subject may be symptomatic or asymptomatic of a given disease or disorder. A subject may be healthy (e.g., not suspected of having disease or disorder). A subject may have one or more risk factors for a given disease. A subject may have a given weight, height, body mass index or other physical characteristics. A subject may have a given ethnic or racial heritage, place of birth or residence, nationality, disease or remission state, family medical history, or other characteristics.

The term "biological sample," as used herein, generally refers to a sample obtained from a subject. The biological sample may be obtained directly or indirectly from the subject. A sample may be obtained from a subject via any suitable method, such as, spitting, swabbing, blood draw, biopsy, obtaining excretions (e.g., urine, stool, sputum, vomit, or saliva), excision, scraping, and puncture. A sample may be obtained from a subject by, for example, intravenously or intraarterially accessing the circulatory system, collecting a secreted biological sample (e.g., stool, urine, saliva, sputum, etc.), breathing, or surgically extracting a tissue (e.g., biopsy). The sample may be obtained by non-invasive methods, such as: scraping of the skin or cervix, swabbing of the cheek, or collection of saliva, urine, feces, menses, tears, or semen. Alternatively, the sample may be obtained by an invasive procedure such as biopsy, needle aspiration, or phlebotomy. A sample may comprise a bodily fluid such as, blood (e.g., whole blood, red blood cells, leukocytes or white blood cells, platelets), plasma, serum, sweat, tears, saliva, sputum, urine, semen, mucus, synovial fluid, breast milk, colostrum, amniotic fluid, bile, bone marrow, interstitial or extracellular fluid, or cerebrospinal fluid. For example, a sample may be obtained by a puncture method to obtain a bodily fluid comprising blood and/or plasma. Such a sample may comprise both cells and cell-free nucleic acid material. Alternatively, the sample may be obtained from any other source such as blood, sweat, hair follicle, buccal tissue, tears, menses, feces, or saliva. The biological sample may be a tissue sample, such as a tumor biopsy. The sample may be obtained from any of the tissues provided herein comprising skin, heart, lung, kidney, breast, pancreas, liver, intestine, brain, prostate, esophagus, muscle, smooth muscle, bladder, gall bladder, colon, or thyroid. The methods of obtaining provided herein include methods of biopsy including fine needle aspiration, core needle biopsy, vacuum assisted biopsy, large core biopsy, incisional biopsy, excisional biopsy, punch biopsy, shave biopsy or skin biopsy. The biological sample may comprise one or more cells. A biological sample may comprise one or more nucleic acid molecules such as one or more deoxyribonucleic acid (DNA) and/or ribonucleic acid (RNA) molecules (e.g., included within cells or not included within cells). Nucleic acid molecules may be included within cells. Alternatively or in addition, nucleic acid molecules may not be included within cells (e.g., cell-free nucleic acid molecules). The biological sample may be a cell-free sample.

The term "cell-free sample," as used herein, generally refers to a sample that is substantially free of cells (e.g., less than 10% cells on a volume basis). A cell-free sample may be derived from any source (e.g., as described herein). For example, a cell-free sample may be derived from blood, sweat, urine, or saliva. For example, a cell-free sample may be derived from a tissue or bodily fluid. A cell-free sample may be derived from a plurality of tissues or bodily fluids. For example, a sample from a first tissue or fluid may be combined with a sample from a second tissue or fluid (e.g., while the samples are obtained or after the samples are obtained). In an example, a first fluid and a second fluid may be collected from a subject (e.g., at the same or different times) and the first and second fluids may be combined to provide a sample. A cell-free sample may comprise one or more nucleic acid molecules such as one or more DNA or RNA molecules.

A sample that is not a cell-free sample (e.g., a sample comprising one or more cells) may be processed to provide a cell-free sample. For example, a sample that includes one or more cells as well as one or more nucleic acid molecules (e.g., DNA and/or RNA molecules) not included within cells (e.g., cell-free nucleic acid molecules) may be obtained from a subject. The sample may be subjected to processing (e.g., as described herein) to separate cells and other materials from the nucleic acid molecules not included within cells, thereby providing a cell-free sample (e.g., comprising nucleic acid molecules not included within cells). The cell-free sample may then be subjected to further analysis and processing (e.g., as provided herein). Nucleic acid molecules not included within cells (e.g., cell-free nucleic acid molecules) may be derived from cells and tissues. For example, cell-free nucleic acid molecules may derive from a tumor tissue or a degraded cell (e.g., of a tissue of a body). Cell-free nucleic acid molecules may comprise any type of nucleic acid molecules (e.g., as described herein). Cell-free nucleic acid molecules may be double-stranded, single-stranded, or a combination thereof. Cell-free nucleic acid molecules may be released into a bodily fluid through secretion or cell death processes, e.g., cellular necrosis, apoptosis, or the like. Cell-free nucleic acid molecules may be released into bodily fluids from cancer cells (e.g., circulating tumor DNA (ctDNA)). Cell free nucleic acid molecules may also be fetal DNA circulating freely in a maternal blood stream (e.g., cell-free fetal nucleic acid molecules such as cffDNA). Alternatively or in addition, cell-free nucleic acid molecules may be released into bodily fluids from healthy cells.

A biological sample obtained directly from a subject may not have been further processed following being obtained from the subject. For example, a blood sample may be obtained directly from a subject by accessing the subject's circulatory system, removing the blood from the subject (e.g., via a needle), and transferring the removed blood into a receptacle. The receptacle may comprise reagents (e.g., anti-coagulants) such that the blood sample is useful for further analysis. In another example, a swab may be used to access epithelial cells on an oropharyngeal surface of the subject. Following obtaining the biological sample from the subject, the swab containing the biological sample may be contacted with a fluid (e.g., a buffer) to collect the biological fluid from the swab.

Any suitable biological sample that comprises one or more nucleic acid molecules may be obtained from a subject. A sample (e.g., a biological sample or cell-free biological sample) suitable for use according to the methods provided herein may be any material comprising tissues, cells, degraded cells, nucleic acids, genes, gene fragments, expression products, gene expression products, and/or gene expression product fragments of an individual to be tested. A biological sample may be solid matter (e.g., biological tissue) or may be a fluid (e.g., a biological fluid). In general, a biological fluid may include any fluid associated with living organisms. Examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, microbiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. Methods for determining sample suitability and/or adequacy are provided. A sample may comprise blood, plasma, tissue, cells, degraded cells, cell-free nucleic acid molecules, and/or biological material from cells or derived from cells of an individual such as cell-free nucleic acid molecules. The sample may be a heterogeneous or homogeneous population of cells, tissues, or cell-free biological material. The biological sample may be obtained using any method that can provide a sample suitable for the analytical methods described herein.

A sample (e.g., a biological sample or cell-free biological sample) may undergo one or more processes in preparation for analysis such as filtration, centrifugation, selective precipitation, permeabilization, isolation, agitation, heating, purification, and/or other processes. For example, a sample may be filtered to remove contaminants or other materials. In an example, a sample comprising cells may be processed to separate the cells from other material in the sample. Such a process may be used to prepare a sample comprising only cell-free nucleic acid molecules. Such a process may consist of a multi-step centrifugation process. Multiple samples, such as multiple samples from the same subject (e.g., obtained in the same or different manners from the same or different bodily locations, and/or obtained at the same or different times (e.g., seconds, minutes, hours, days, weeks, months, or years apart)) or multiple samples from different subjects may be obtained for analysis as described herein. In an example, the first sample is obtained from a subject before the subject undergoes a treatment regimen or procedure and the second sample is obtained from the subject after the subject undergoes the treatment regimen or procedure. Alternatively or in addition, multiple samples may be obtained from the same subject at the same or approximately the same time. Different samples obtained from the same subject may be obtained in the same or different manner. For example, a first sample may be obtained via a biopsy and a second sample may be obtained via a blood draw. Samples obtained in different manners may be obtained by different medical professionals, using different techniques, at different times, and/or at different locations. Different samples obtained from the same subject may be obtained from different areas of a body. For example, a first sample may be obtained from a first area of a body (e.g., a first tissue) and a second sample may be obtained from a second area of the body (e.g., a second tissue).

A biological sample as used herein (e.g., a biological sample comprising one or more nucleic acid molecules) may not be purified when provided in a reaction vessel. Furthermore, for a biological sample comprising one or more nucleic acid molecules, the one or more nucleic acid molecules may not be extracted when the biological sample is provided to a reaction vessel. For example, ribonucleic acid (RNA) and/or deoxyribonucleic acid (DNA) molecules of a biological sample may not be extracted from the biological sample when providing the biological sample to a reaction vessel. Moreover, a target nucleic acid (e.g., a target RNA or target DNA molecules) present in a biological sample may not be concentrated when providing the biological sample to a reaction vessel. Alternatively, a biological sample may be purified and/or nucleic acid molecules may be isolated from other materials in the biological sample.

A biological sample as described herein may be or contain a target nucleic acid. As used herein, the terms "template nucleic acid", "target nucleic acid", "nucleic acid molecule," "nucleic acid sequence," "nucleic acid fragment," "oligonucleotide," "polynucleotide," and "nucleic acid" generally refer to polymeric forms of nucleotides of any length, such as deoxyribonucleotides (dNTPs) or ribonucleotides (rNTPs), or analogs thereof, and may be used interchangeably. Nucleic acids may have any three-dimensional structure, and may perform any function, known or unknown. A nucleic acid molecule may have a length of at least about 10 nucleic acid bases ("bases"), 20 bases, 30 bases, 40 bases, 50 bases, 100 bases, 200 bases, 300 bases, 400 bases, 500 bases, 1 kilobase (kb), 2 kb, 3, kb, 4 kb, 5 kb, 10 kb, 50 kb, or more. An oligonucleotide is typically composed of a specific sequence of four nucleotide bases: adenine (A); cytosine (C); guanine (G); and thymine (T) (uracil (U) for thymine (T) when the polynucleotide is RNA). Oligonucleotides may include one or more nonstandard nucleotide(s), nucleotide analog(s) and/or modified nucleotides. Examples of nucleic acids include DNA, RNA, genomic DNA (e.g., gDNA such as sheared gDNA), cell-free DNA (e.g., cfDNA), synthetic DNA/RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, complementary DNA (cDNA), recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or following assembly of the nucleic acid. The sequence of nucleotides of a nucleic acid may be interrupted by non-nucleotide components. A nucleic acid may be further modified following polymerization, such as by conjugation or binding with a reporter agent.

A target nucleic acid may be a target RNA or a target DNA. When the target nucleic acid is a target RNA, the target RNA may be any type of RNA, including types of RNA described elsewhere herein. The target RNA may be viral RNA and/or tumor RNA. A viral RNA may be pathogenic to a subject. Examples of pathogenic viral RNA include human immunodeficiency virus I (HIV I), human immunodeficiency virus n (HIV 11), orthomyxoviruses, Ebola virus. Dengue virus, influenza viruses (e.g., H1N1, H3N2, H7N9, or H5N1), herpesvirus, hepatitis A virus, hepatitis B virus, hepatitis C (e.g., armored RNA-HCV virus) virus, hepatitis D virus, hepatitis E virus, hepatitis G virus, Epstein-Barr virus, mononucleosis virus, cytomegalovirus, SARS virus, West Nile Fever virus, polio virus, and measles virus.

A biological sample may comprise a plurality of target nucleic acid molecules. For example, a biological sample may comprise a plurality of target nucleic acid molecules from a single subject. In another example, a biological sample may comprise a first target nucleic acid molecule from a first subject and a second target nucleic acid molecule from a second subject.

As used herein, the term "primer" or "primer molecule" generally refers to a polynucleotide which is complementary to a portion of a template nucleic acid molecule or derivative thereof. For example, a primer may be complementary to a portion of a strand of a template nucleic acid molecule. The primer may be a strand of nucleic acid that serves as a starting point for nucleic acid synthesis, such as a primer extension reaction which may be a component of a nucleic acid reaction (e.g., nucleic acid amplification reaction such as PCR). A primer may hybridize to a template strand and nucleotides (e.g., canonical nucleotides or nucleotide analogs) may then be added to the end(s) of a primer, sometimes with the aid of a polymerizing enzyme such as a polymerase. For example, during replication of a DNA sample, an enzyme that catalyzes replication may start replication at the 3'-end of a primer attached to the DNA sample and copy the opposite strand. A primer (e.g., oligonucleotide) may have one or more functional groups that may be used to couple the primer to a support or carrier, such as a bead or particle.

A primer may be completely or partially complementary to a template nucleic acid or derivative thereof. A primer may exhibit sequence identity or homology or complementarity to the template nucleic acid. The homology or sequence identity or complementarity between the primer and a template nucleic acid may be based on the length of the primer. For example, if the primer length is about 20 nucleic acids, it may contain 10 or more contiguous nucleic acid bases complementary to the template nucleic acid. The complementarity or homology or sequence identity between the primer and the template nucleic acid may be limited. The length of the primer may be between 8 nucleotide bases to 50 nucleotide bases. The length of the primer may be more than 2 nucleotide bases, more than 3 nucleotide bases, 4 nucleotide bases, 5 nucleotide bases, 6 nucleotide bases, 7 nucleotide bases, 8 nucleotide bases, 9 nucleotide bases, 10 nucleotide bases, 11 nucleotide bases, 12 nucleotide bases, 13 nucleotide bases, 14 nucleotide bases, 15 nucleotide bases, 16 nucleotide bases, 17 nucleotide bases, 18 nucleotide bases, 19 nucleotide bases, 20 nucleotide bases, 21 nucleotide bases, 22 nucleotide bases, 23 nucleotide bases, 24 nucleotide bases, 25 nucleotide bases, 26 nucleotide bases, 27 nucleotide bases, 28 nucleotide bases, 29 nucleotide bases, 30 nucleotide bases, 31 nucleotide bases, 32 nucleotide bases, 33 nucleotide bases, 34 nucleotide bases, 35 nucleotide bases, 37 nucleotide bases, 40 nucleotide bases, 42 nucleotide bases, 45 nucleotide bases, 47 nucleotide bases or 50 nucleotide bases. The length of the primer may be less than 50 nucleotide bases, 47 nucleotide bases, 45 nucleotide bases, 42 nucleotide bases, 40 nucleotide bases, 37 nucleotide bases, 35 nucleotide bases, 34 nucleotide bases, 33 nucleotide bases, 32 nucleotide bases, 31 nucleotide bases, 30 nucleotide bases, 29 nucleotide bases, 28 nucleotide bases, 27 nucleotide bases, 26 nucleotide bases, 25 nucleotide bases, 24 nucleotide bases, 23 nucleotide bases, 22 nucleotide bases, 21 nucleotide bases, 20 nucleotide bases, 19 nucleotide bases, 18 nucleotide bases, 17 nucleotide bases, 16 nucleotide bases, 15 nucleotide bases, 14 nucleotide bases, 13 nucleotide bases, 12 nucleotide bases, 11 nucleotide bases, 10 nucleotide bases, 9 nucleotide bases, 8 nucleotide bases, 7 nucleotide bases, 6 nucleotide bases, 5 nucleotide bases, 4 nucleotide bases, 3 nucleotide bases or 2 nucleotide bases.

As used herein, the term "primer extension reaction" generally refers to the binding of a primer to a strand of the template nucleic acid, followed by elongation of the primer(s). It may also include, denaturing of a double-stranded nucleic acid and the binding of a primer strand to either one or both of the denatured template nucleic acid strands, followed by elongation of the primer(s). Primer extension reactions may be used to incorporate nucleotides or nucleotide analogs to a primer in template-directed fashion by using enzymes (e.g., polymerizing enzymes such as polymerases). A primer extension reaction may be a process of a nucleic acid amplification reaction.

The terms "polymerase," "polymerizing enzyme, or "polymerization enzyme," as used herein, generally refer to any enzyme capable of catalyzing a polymerization reaction and may be used interchangeably. A polymerizing enzyme may be used to extend primers with the incorporation of nucleotides or nucleotide analogs. Examples of polymerases may comprise a nucleic acid polymerase. The polymerase may be naturally occurring or synthesized. An example polymerase is a Φ29 polymerase or derivative thereof. A polymerase may be a polymerization enzyme. A transcriptase or a ligase may also be used (i.e., enzymes which catalyze the formation of a bond). Examples of polymerases include a DNA polymerase, an RNA polymerase, a thermostable polymerase, a wild-type polymerase, a modified polymerase, E. coli DNA polymerase I, T7 DNA polymerase, bacteriophage T4 DNA polymerase Φ29 (phi29) DNA polymerase, Taq polymerase, Tth polymerase, Tli polymerase, Pfu polymerase Pwo polymerase, VENT polymerase, DEEPVENT polymerase, Ex-Taq polymerase, LA-Taw polymerase, Sso polymerase Poc polymerase, Pab polymerase, Mth polymerase ES4 polymerase, Tru polymerase, Tac polymerase, Tne polymerase, Tma polymerase, Tca polymerase, Tih polymerase, Tfi polymerase, Platinum Taq polymerases, Tbr polymerase, Tfl polymerase, Pfutubo polymerase, Pyrobest polymerase, KOD polymerase, Bst polymerase, Sac polymerase, Klenow fragment polymerase with 3' to 5' exonuclease activity, and variants, modified products and derivatives thereof. The polymerase may be a single subunit polymerase. The polymerase may have high processivity, namely the capability of the polymerase to consecutively incorporate nucleotides in a nucleic acid template without releasing the nucleic acid template.

Methods and Systems for Large Volume Emulsion

The methods described herein may be conducted in a reaction vessel or processing vessel (e.g., a droplet in an emulsion, a well among a plurality of wells, or both). Any suitable reaction/processing vessel may be used. The terms reaction vessel and processing vessel may be used interchangeably where suitable herein. A reaction or process taking place in a reaction vessel or processing vessel may comprise any reaction, such as any chemical reaction and any chemical or physical part or step of a reaction or process (such as the reactions and processes mentioned or listed anywhere herein). For example, a reaction may be a PCR reaction. A process may be heating, cooling, subjecting a sample to alternate heating and cooling cycles (e.g., thermal cycling), or any other chemical or physical process for performing the methods of the present disclosure and/or any combination thereof. A reaction vessel may be configured to facilitate different types of reactions or processes.

A reaction vessel may comprise a body comprising an interior surface, an exterior surface, and, in some cases, an open end and an opposing closed end. In some cases, a reaction vessel may not comprise an open or closed end. For example, a reaction vessel may be a droplet. In other cases, a reaction vessel may comprise a cap, which cap may be configured to contact the body at an open end, such that when contact is made the open end of the reaction vessel is closed. The cap may be permanently associated with the reaction vessel such that it remains attached to the reaction vessel in open and closed configurations. The cap may be removable, such that when the reaction vessel is open, the cap is separated from the reaction vessel. A reaction vessel such as a flow cell chamber (e.g., a flow cell chamber comprising a water-in-oil emulsion or a plurality of wells) may comprise one or more inlets or outlets, which inlets or outlets may be used to provide and remove reagents for use in a reaction. Reagents may be moved in and out of the chamber via pressure and vacuum controls. A reaction vessel as used herein may be sealed, optionally hermetically sealed (e.g., a sealed microwell plate).

A reaction vessel may be of varied size, shape, weight, and configuration. Some reaction vessels may be substantially round or oval tubular shaped. Some reaction vessels may be rectangular, square, diamond, circular, elliptical, or triangular shaped. A reaction vessel may be regularly shaped or irregularly shaped. For example, a reaction vessel that is a droplet (e.g., a droplet in an emulsion, such as an aqueous droplet) may be substantially spherical. A closed end of a reaction vessel (e.g., a well of a microwell plate or flow cell) may have a tapered, rounded, or flat surface. Some examples of types of a reaction vessel may comprise a tube, a well, a capillary tube, a cartridge, a cuvette, a centrifuge tube, a droplet, or a pipette tip. Reaction vessels may be comprised of any suitable material with examples of such materials comprising glasses, metals, plastics, polymers, thermoplastic polymers, polyolefins, any material commonly used in laboratories (e.g., standard labware), immiscible fluids, organic oils and surfactants, and combinations thereof.

A reaction vessel may be a droplet, such as an aqueous droplet in an immiscible fluid such as an oil. A reaction vessel may be of any suitable size. For example, a reaction vessel may be an approximately spherical droplet having a diameter of at least about 1 nanometer (nm), 2 nm, 3 nm, 4 nm, 5 nm, 6 nm, 7 nm, 8 nm, 9 nm, 10 nm, 20 nm, 30 nm, 40 nm, 50 nm, 60 nm, 70 nm, 80 nm, 90 nm, 100 nm, 200 nm, 300 nm, 400 nm, 500 nm, 600 nm, 700 nm, 800 nm, 900 nm, 1000 nm or 1 micron (µm), 2 µm, 3 µm, 4 µm, 5 µm, 6 µm, 7 µm, 8 µm, 9 µm, 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1000 µm or 1 millimeter (mm), 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, or greater. Alternatively or in addition, the diameter may be at most about 100 mm, 90 mm, 80 mm, 70 mm, 60 mm, 50 mm, 40 mm, 30 mm, 20 mm, 10 mm, 9 mm, 8 mm, 7 mm, 6 mm, 5 mm, 4 mm, 3 mm, 2 mm, 1 mm or 1000 µm, 900 µm, 800 µm, 700 µm, 600 µm, 500 µm, 400 µm, 300 µm, 200 µm, 100 µm, 90 µm, 80 µm, 70 µm, 60 µm, 50 µm, 40 µm, 30 µm, 20 µm, 10 µm, 9 µm, 8 µm, 7 µm, 6 µm, 5 µm, 4 µm, 3 µm, 2 µm, 1 µm or 1000 nm, 900 nm, 800 nm, 700 nm, 600 nm, 500 nm, 400 nm, 300 nm, 200 nm, 100 nm, 90 nm, 80 nm, 70 nm, 60 nm, 50 nm, 40 nm, 30 nm, 20 nm, 10 nm, 9 nm, 8 nm, 7 nm, 6 nm, 5 nm, 4 nm, 3 nm, 2 nm, 1 nm or less. In some examples, the diameter of the droplets may be between about 2 µm to 10 µm. In some examples, the diameter of the droplets may be between 3 µm to 6 µm. A reaction vessel may accommodate various volumes. For example, a droplet may have a volume on the order of at least about 1 µL, 10 µL, 100 µL, 1000 µL (or 1 mL), or greater. Alternatively or in addition, a droplet may have a volume on the order of at most about 1000 µL (or 1 mL), 100 µL, 10 µL, 1 µL, or less.

A reaction vessel may be a well or microwell. In some examples, a reaction vessel may be a well having a diameter on the order of at least about 10 µm, 100 µm, 1 mm, 10 mm, 100 mm, or greater. Alternatively or in addition, the diameter may be on the order of at most about 100 mm, 10 mm, 1 mm, 100 µm, 10 µm or less. The reaction vessel may have a diameter of at least about 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1000 µm (or 1 mm), 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm or greater. Alternatively or in addition, the reaction vessel may have a diameter of at most about 100 mm, 90 mm, 80 mm, 70 mm, 60 mm, 50 mm, 40 mm, 30 mm, 20 mm, 10 mm, 9 mm, 8 mm, 7 mm, 6 mm, 5 mm, 4 mm, 3 mm, 2 mm, 1 mm (or 1000 µm), 900 µm, 800 µm, 700 µm, 600 µm, 500 µm, 400 µm, 300 µm, 200 µm, 100 µm, 90 µm, 80 µm, 70 µm, 60 µm, 50 µm, 40 µm, 30 µm, 20 µm, 10 µm, or less. The depth of a well may be the same as or different than the diameter of the well. For example, the reaction vessel may have a depth of at least about 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1000 µm (or 1 mm), 2 mm, 3 mm, 4 mm, 5 mm, 6 mm, 7 mm, 8 mm, 9 mm, 10 mm, 20 mm, 30 mm, 40 mm, 45 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, or greater. Alternatively or in addition, the reaction vessel may have a depth of at most about 200 mm, 190 mm, 180 mm, 170 mm, 160 mm, 150 mm, 140 mm, 130 mm, 120 mm, 110 mm, 100 mm, 90 mm, 80 mm, 70 mm, 60 mm, 50 mm, 40 mm, 30 mm, 20 mm, 10 mm, 9 mm, 8 mm, 7 mm, 6 mm, 5 mm, 4 mm, 3 mm, 2 mm, 1 mm (or 1000 µm), 900 µm, 800 µm, 700 µm, 600 µm, 500 µm, 400 µm, 300 µm, 200 µm, 100 µm, 90 µm, 80 µm, 70 µm, 60 µm, 50 µm, 40 µm, 30 µm, 20 µm, 10 µm, or less. In an example, the well has a diameter of about 5 mm and a depth of about 10 mm.

The shape of a cross-section of the well may be circular, cylindrical, square, cubical, rectangular, triangle, pyramidal, or any other suitable shape. The shape may be a regular shape or an irregular shape. In some examples, a well may comprise a circular cross section. For example, the well may be a cylinder. The diameter of the circular cross-section of the well may be according to any well diameter provided elsewhere herein. In some examples, the walls of the well may be curved. In some examples, a well may comprise a rectangular cross-section or a near rectangular cross-section (e.g., a rectangle with rounded corners). In some examples, the well may comprise flat surfaces. For example, the walls of the well may be flat. In some cases, flat walls of the wells and/or containers may complement the fins and facilitate or promote a close contact and effective heat transfer with the fins (e.g., fins 530 described in further detail elsewhere herein). In some examples, the sides of a cross-section (e.g., a rectangle) may be at least about 10 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1000 µm (or 1 mm), 2 mm, 3 mm, 4 mm, 5 mm, 6 mm, 7 mm, 8 mm, 9 mm, 10 mm, 20 mm, or more. In an example, a well may comprise an 8.45 mm×6.4 mm rectangular cross section and a depth of about 45 mm.

In some cases, the walls of the vessels (e.g., containers or tubes) may be relatively thin. Thin walls may allow for efficient heat transfer between an interior region and exterior region of the vessels. For example, the thickness of the walls of the wells in a well-plate array, cartridge or vessel may be at least about 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm or more. Alternatively or in addition, the thickness of the walls of the wells, vessels or containers may be at most about 2 mm, 1.9 mm, 1.8 mm, 1.7 mm, 1.6 mm, 1.5 mm, 1.4 mm, 1.3 mm, 1.2 mm, 1.1 mm, 1 mm, 0.9 mm, 0.8 mm, 0.7 mm, 0.6 mm, 0.5 mm, 0.4 mm, 0.3 mm, 0.2 mm, 0.1 mm or less.

The vessels or containers may be made of any material. In some examples, the materials used for containers may comprise a high chemical durability to withstand one or more chemical reaction conditions (e.g., thermal, optical stimuli, etc.) and/or reagents and products thereof. Materials used may be suitable for injection molding. In some examples, the wells may be made of plastics or polymers (e.g., thermoplastic polymers). In an example, the wells, cartridge, vessels, chamber, or containers may be made of materials such as polypropylene (PP), polystyrene (PS), polycarbonate, and the like.

One or more reaction vessels may be provided within a cartridge. A cartridge may comprise a plurality of reaction vessels (e.g., outer reaction vessels, inner reaction vessels). The plurality of reaction vessels may be modularly assembled in the cartridge. The plurality of reaction vessels may be integral to a single component (e.g., an integral well plate). A reaction vessel may be part of a collection or an array of reaction vessels (e.g., in or as part of a cartridge). A collection or an array of reaction vessels may be particularly useful for automating methods and/or simultaneously processing multiple samples, and/or multiple aliquots of a sample. A reaction vessel may be a well of a well plate (e.g., microwell plate) comprised of a number of wells. A reaction vessel may be disposed in a well or a well plate that is in thermal communication with a thermal block (e.g., comprising a heat exchange element such as a body of fluid) of a thermocycler. The thermal block of the thermocycler may be in direct mechanical contact or in indirect contact with multiple wells each capable of receiving one or more reaction vessels (e.g., sample-containing reaction vessels) such as to facilitate thermal transfer between the thermal block and the reaction vessels (or contents thereof) within the respective wells.

A collection or an array comprising a plurality of reaction vessels (e.g., droplets or wells) may comprise any appropriate number of reaction vessels. A collection or an array of reaction vessels may include at least 1, 2, 3, 4, 5, 6, 7, 8, 9, 10, 20, 30, 40, 50, 60, 70, 80, 90, 100, 200, 300, 400, 500, 1,000, 10,000 or more vessels. For example, a collection or an array of reaction vessels may comprise at least 2, 4, 6, 8, 10, 12, 14, 16, 18, 20, 25, 35, 48, 96, 144, 384, or more reaction vessels. In an example, an array of 96 wells is suitable for performing the methods of the present disclosure. A reaction vessel that is part of a collection or an array of reaction vessels (e.g., wells) may also be individually addressable by a fluid handling device, such that the fluid handling device may correctly identify a reaction vessel and dispense appropriate materials into the reaction vessel. Fluid handling devices may be useful in automating the addition of materials to reaction vessels.

A collection or an array comprising a plurality of reaction vessels may comprise any appropriate shape and dimensions. For example, the wells may be arranged in a rectangular plate, a circular plate, a triangular plate, a diamond plate, a square plate, or a plate with any shape or form. In some examples, an array (e.g., an array plate) may be a rectangle. The array may comprise dimensions such as width length and height (or depth). In some examples, the width or length of the plate (e.g., array plate) may be at least about 10 mm, 20 mm, 30 mm, 40 mm, 50 mm, 60 mm, 70 mm, 80 mm, 90 mm, 100 mm, 110 mm, 120 mm, 130 mm, 140 mm, 150 mm, 200 mm, 300 mm, 400 mm, or 500 mm. Alternatively, the width or length of the plate (e.g., array plate) may be at most 500 mm, 400 mm, 300 mm, 200 mm, 150 mm, 140 mm, 130 mm, 120 mm, 110 mm, 100 mm, 90 mm, 80 mm, 70 mm, 60 mm, 50 mm, 40 mm, 30 mm, 20 mm, or 10 mm. In some embodiments, the plate has a width of about 80 mm and a length of about 120 mm. In some cases, the plate may conform with standard 96-well dimensions (e.g., 86 mm×128 mm) albeit with a much deeper depth. In some examples, a plate configuration conforming with standard 96-well dimensions with a deeper depth may be preferred. In some examples, the plate may have a dimension larger than 500 mm or smaller than 10 mm.

In some examples, the depth of the array may be at least about 10 mm, 20 mm, 30 mm, 40 mm, 45 mm, 50 mm, 60 mm, 70 mm, 80 mm, 90 mm, 100 mm, 110 mm, 120 mm, 130 mm, 140 mm, 150 mm, 160 mm, 170 mm, 180 mm, 190 mm, 200 mm, or greater. Alternatively or in addition, the reaction vessel may have a depth of at most about 200 mm, 190 mm, 180 mm, 170 mm, 160 mm, 150 mm, 140 mm, 130 mm, 120 mm, 110 mm, 100 mm, 90 mm, 80 mm, 70 mm, 60 mm, 50 mm, 40 mm, 30 mm, 20 mm, or 10 mm. In an example, the array plate has a 79.86 mm×119.86 mm rectangular cross section with a depth of about 45 mm.

In some examples, an array of reaction vessels (e.g., cartridge) may comprise a plate, such as a trough plate. A cartridge may comprise a plate having a trough-like configuration. A trough plate may comprise one or more trough channels, such as at least 1, 2, 3, 4, 5, 6, 7, 8, 9, 10, 11, 12, 13, 14, 15, 16, 17, 18, 19, 20, 21, 22, 23, 24, 48, 96, or more channels. In some cases, a channel of the one or more trough channels may comprise a capacity of at least about 100 micro-Liters (µL), 200 µL, 300 µL, 500 µL, 600 µL, 700 µL, 800 µL, 900 µL, 1000 µL (1 milliLiter (mL)), 2 mL, 3 mL, 4 mL, 5 mL, 6 mL, 7 mL, 8 mL, 9 mL, 10 mL, 12 mL, 15 mL, 20 mL, 30 mL, or more. In an example, a trough plate may comprise 8 channel troughs, each channel trough may comprise from about 0.1 mL to about 15 mL capacity, and the trough plate may comprise a total capacity of from about 0.8 mL to about 120 mL. In an example, the trough plate may comprise 12 channel troughs, and each channel trough may comprise from about 0.1 mL to about 10 mL capacity, and the trough plate may comprise a total capacity of from about 1.2 mL to about 120 mL. In other examples, the trough plate may comprise any number of channels, and each channel may comprise any suitable capacity.

In some cases, the trough plate may benefit from or need tolerancing and/or material compliance in one or more dimensions. In some cases, the plate may not need tolerancing and/or material compliance in three-dimensions. For example, a trough plate may only need tolerancing and/or material compliance in 1 dimension or 2 dimensions. In an example, a plate may need tolerancing (e.g., critical tolerancing).

Figure 5A:
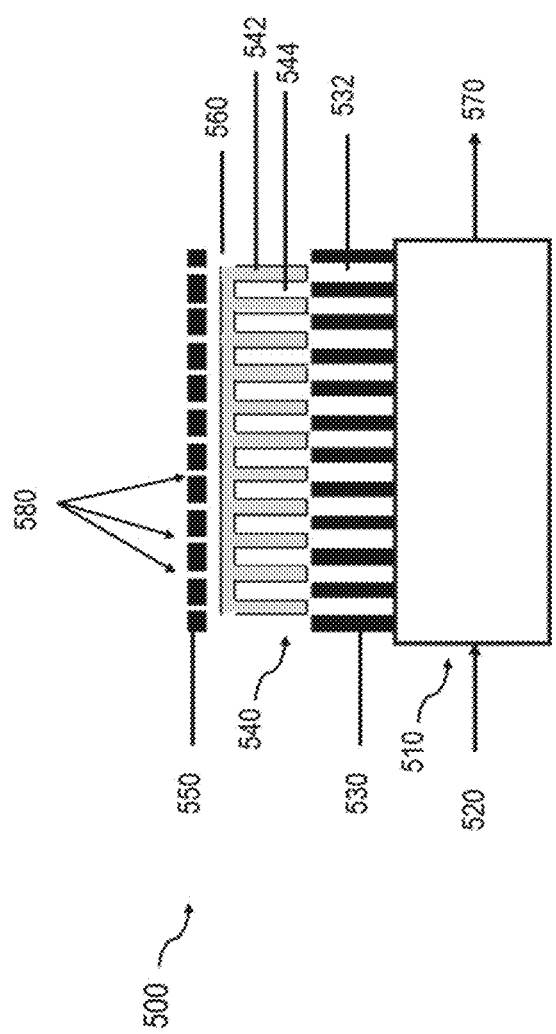
FIG. 5A shows the view from the side of an example system comprising a heat exchange system and thermocycler for performing the methods of the present disclosure.
Figure 5B:
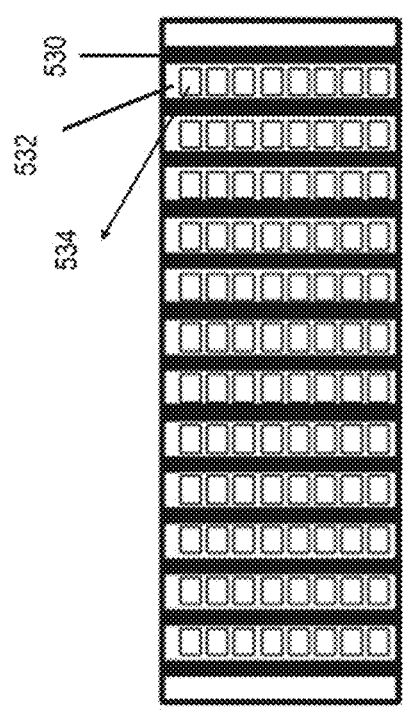
FIG. 5B shows the view from the top of the system shown in FIG. 5A.

FIG. 5B illustrates an example cartridge, array, or multi-well plate comprising a collection of reaction vessels that may be used to perform the methods of the present disclosure. A plurality of wells (e.g., 96 wells) may be provided in an array in a well plate (e.g., an array plate or multi-well plate array). The well plate may have any configuration of wells or other reaction vessels (e.g., containers, tubes, etc.). They may be arranged in a regular or irregular pattern. For example, the wells may be sorted in a rectangular array. In an example, as illustrated in FIG. 5B, 96 wells are sorted in a rectangular configuration with 8 rows and 12 columns to make a 96 (8×12) well plate. The configuration of the reaction vessels in the plate may be adjusted and customized for different applications. In some applications, the well plate may be used for warming and/or cooling a sample which may be contained in the wells. In such examples, the wells may comprise thin walls. The wells may be designed and configured according to any reaction vessel described herein. In an example, the containers used in the cartridge (e.g., well plate, e.g., 96-well configuration) can be made of polypropylene. In some examples, the example cartridge may be made by injection molding (e.g., injection molding polypropylene). In some cases, the thickness of the walls of the containers or wells may be in a range of about 0.1 mm to about 0.9 mm, or about 0.3 mm to about 0.6 mm, or about between 0.4 mm to 0.5 mm. A well of the well plate may be configured to contain at least about 0.4 milliliter (mL), 0.5 mL, 0.6 mL, 0.7 mL, 0.8 mL, 0.9 mL, 1.0 mL, 1.1 mL, 1.2 mL, 1.3 mL, 1.4 mL, 1.5 mL, 2.0 mL, 2.5 mL, or 3.0 mL of a sample. Alternatively or in addition, each well may be configured to contain at most about 3.0 mL, 2.5 mL, 2.0 mL, 1.5 mL, 1.4 mL, 1.3 mL, 1.2 mL, 1.1 mL, 1.0 mL, 0.9 mL, 0.8 mL, 0.7 mL, 0.6 mL, 0.5 mL, or 0.4 mL of a sample, or less. In some embodiments, a well may contain less than 0.4 mL or more than 3.0 mL of a sample.

In some cases, one or more reaction vessels may be included within another reaction vessel. A reaction vessel may be placed inside another reaction vessel, which may be placed inside another reaction vessel, and so on. For example, an inner reaction vessel is disposed within an outer reaction vessel, such as a droplet within a well or a droplet within another droplet. An outer reaction vessel may comprise a plurality of inner reaction vessels, such as a plurality of droplets within a well or a plurality of droplets within another droplet. The inner reaction vessel may be configured to facilitate isolation of one or more reaction components, e.g., reagents and products, within the inner reaction vessel and distinct from other reaction vessels (inner or outer). The outer reaction vessel may be configured to facilitate isolation of one or more inner reaction vessels from other inner reaction vessels (e.g., in other outer reaction vessels). The outer reaction vessel may be configured to facilitate subjecting one or more inner reaction vessels within the outer reaction vessel to one or more controlled reaction conditions (e.g., temperature change, pressure change, addition of reagents or surfactants, etc.). The outer reaction vessel may be configured to serve as efficient containers to hold inner reaction vessels and/or transfer one or more reaction conditions (e.g., temperature change, reagent transfer, etc.) through the outer reaction vessel to the inner reaction vessel(s). For example, the walls, membranes, or other component of the outer reaction vessel may be configured to permit efficient heat transfer or reagent transfer from an outer environment (e.g., heat bath) to an inner environment of the outer reaction vessel. Similarly, the walls, membranes, or other component of the inner reaction vessel may be configured to permit efficient heat transfer or reagent transfer from an outer reaction vessel environment (e.g., heat bath) to an inner environment of the inner reaction vessel For example, a plurality of droplets may be included in a container such as a beaker, test tube, flow cell chamber, well, or other container, or a plurality of wells (e.g., of a microwell plate or flow cell) may be included in a container, such as a flow cell chamber, other wells, a multi-well plate, a cartridge, or other container. In an example, a plurality of wells may be provided on a surface of a flow cell chamber, such that a nucleic acid reaction may take place directly on a flow cell. In another example, one or more droplets may be physically constrained to a given area, such as a surface of a container. Droplets may be physically constrained via, for example, an electromagnetic force, such as via a magnetic attraction between a material (e.g., surface) of the container and a material included within the droplet (e.g., a paramagnetic bead or a magnetic label coupled to a bead) or via the use of optical tweezers. In an example, droplets may be constrained within wells, such as in a well plate or flow cell, such as the well plates or cartridges described elsewhere herein.

In some examples, an emulsion of droplets may be generated and processed inside a plurality of containers such as wells (e.g., in an array well plate, such as a 96-well plate). Processing may comprise forming droplets, warming and/or cooling the sample and/or the emulsion, subjecting an emulsion of droplets to thermal cycling, performing reactions in the sample and/or emulsion, breaking, merging, or coalescing droplets, pooling the contents of droplets, subjecting the contents of droplets or sample to sequencing or any other type of measurement or analysis, centrifugation, separating various sample components, any combination and/or sequence thereof, and more.

A reaction vessel (e.g., droplet or well) may comprise multiple thermal zones. Thermal zones may be created within a reaction vessel with the aid of thermal sensitive layering materials within the reaction vessels. In such cases, heating of the thermal sensitive layering materials may be used to release reaction mixtures from one thermal zone to the next. A reaction vessel may comprise 2, 3, 4, 5, 6, 7, 8, 9, 10, 11, 12, 13, 14, 15, 20 or more thermal zones. Thermal zones within a reaction vessel may be achieved by exposing different regions of the reaction vessel to different temperature cycling conditions. For example, different regions of a flow cell chamber (e.g., comprising a plurality of wells and/or droplets) may be subjected to different temperature cycling conditions. Alternatively, one or more reaction vessels of an array or a collection of reaction vessels may be subjected to one or more different thermal zones. For example, a first set of reaction vessels may be placed within a first thermal zone and a second set of reaction vessels may be placed within a second thermal zone (e.g., by physically separating the various reaction vessels).

Alternatively or in addition, one or more reaction vessels of an array or a collection of reaction vessels may be subjected to multiple different temperatures (e.g., at different times throughout a process). Temperatures applied to a reaction vessel may be suitable for, for example, initialization of a nucleic acid reaction, annealing of nucleic acid molecules, extension of an annealed nucleic acid molecule (e.g., primer extension), partial or complete denaturation of a double-stranded nucleic acid sequence or portion thereof, or any other useful process. For example, temperatures may be controlled according to a thermocycling protocol. In an example, all or a portion of a reaction vessel may be subjected to a first temperature at a first time for a first duration, and the reaction vessel or portion thereof may subsequently be subjected to a second temperature at a second time for a second duration. The first temperature may be, for example, a temperature suitable for initialization of a nucleic acid reaction (e.g., PCR) or annealing (e.g., hybridization) of a first nucleic acid molecule to a second nucleic acid molecule. The second temperature may be, for example, a temperature suitable for extension of an annealed nucleic acid molecule (e.g., a primer molecule) and/or denaturation of annealed nucleic acid molecules. Additional different temperatures may also be applied. Temperatures may be repeated any suitable number of times (e.g., for any number of thermocycles).

Provided herein are systems and methods that can facilitate performing emulsion PCR in large volumes at high-throughput (e.g., comprising a faster rate compared to conventional methods, facilitating processing a given volume of sample in a shorter period). In some examples, the methods may comprise one or more steps. The one or more steps of the methods may comprise droplet formation, thermal cycling, droplet breaking, washing, enrichment, sample preparation, PCR reaction, any combination or sequence thereof, and more. The methods or the one or more steps of the methods may be completed in a given duration of time. The duration of time may be any duration of time. In some examples, the methods may be fast or high-throughput.

In some cases, the methods (e.g., some or all of the steps of the methods) can be performed (e.g., to facilitate processing of about 100 milliliters (mL) or another amount of a sample) in at most about 25 hours, 20 hours, 19 hours, 18 hours, 17 hours, 16 hours, 15 hours, 14 hours, 13 hours, 12 hours, 11 hours, 10 hours, 9 hours, 8 hours, 7 hours, 5 hours, 4 hours, 3 hours, 2 hours, 1 hour, 50 minutes (min), 40 min, 40 min, 20 min, 10 min, or less. In some cases, the methods may facilitate processing at least about 10 mL, 20 mL, 30 mL, 40 mL, 50 mL, 60 mL, 70 mL, 80 mL, 90 mL, 100 mL, 110 mL, 120 mL, 130 mL, 140 mL, 150 mL, 160 mL, 170 mL, or more volume in at most about 25 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, or less.

In some examples, the rate of sample processing may be at least about 4 mL/hr (milliliters per hour), 5 mL/hr, 6 mL/hr, 7 mL/hr, 8 mL/hr, 9 mL/hr, 10 mL/hr, 11 mL/hr, 12 mL/hr, 13 mL/hr, 14 mL/hr, 15 mL/hr, 16 mL/hr, 17 mL/hr 18 mL/hr, 19 mL/hr, 20 mL/hr, 30 mL/hr, or more. The rates provided herein may be from a few times to several orders of magnitude faster than existing emulsion PCR (ePCR) methods. For example, the sample processing rates facilitated by the methods of the present disclosure may be at least about 2 times, 3 times, 5 times, 6 times, 8 times, 9 times, 10 times, 11 times, 15 times, 20 times, 25 times, 30 times, 100 times, or to a greater extent faster than existing ePCR workflows. In a particular example, the methods and systems provided herein facilitate completing an ePCR for 10 times larger sample volumes within a given time, compared to existing methods, systems, and technologies.

In an example, a step of the one or more steps of the methods provided herein may comprise performing a PCR reaction. A PCR reaction may be according to the PCR reactions provided elsewhere herein. In some examples, a PCR reaction may be completed in a duration of time such as at most about 12 hours, 11 hours, 10 hours, 9 hours, 8 hours, 7 hours, 6 hours, 5 hours, 4 hours, 3 hours, 2 hours, 1 hour, 50 minutes (min), 40 min, 40 min, 20 min, 10 min, or less.

The systems and methods provided herein may process a sample. The sample may comprise a biological sample, such as a nucleic acid molecule or a plurality of nucleic acid molecules. The sample may comprise a plurality of beads. The methods and systems provided herein may facilitate processing the beads in the sample at a faster rate than, for example, a conventional method which, with one round of the procedure or during a given duration of time, processes about 200 million beads. The methods and systems provided herein may facilitate processing larger volumes of the sample in the same duration of time. In some examples, the methods and systems provided herein may be configure to process at least about 300 million, 400 million, 500 million, 600 million, 700 million, 800 million, 900 million, 1 billion, 2 billion, 3 billion, 4 billion, 5 billion, 6 billion, 7 billion, 8 billion, 9 billion, 10 billion, 11 billion, 12 billion, 13 billion, 14 billion, 15 billion, 16 billion, 17 billion, 18 billion, 19 billion, 20 billion, or more beads. The methods and systems provided herein may facilitate processing larger volumes than, for example, a convention method which, with one round of the procedure or during a given duration of time, processes about 10 mL volume. The methods and systems provided herein may be capable of processing at least about 10 mL, 20 mL, 30 mL, 40 mL, 50 mL, 60 mL, 70 mL, 80 mL, 90 mL, 100 mL, 110 mL, 120 mL, 130 mL, 140 mL, 150 mL, 200 mL, or more in one round.

Provided herein are systems and methods comprising a plurality of modules and procedures for performing a reaction, such as an emulsion PCR (ePCR) or other processes or reactions. The system may comprise manual and/or automated modules and procedures. The methods and systems may comprise providing and using one or more devices. The devices may comprise an ePCR device. The methods may facilitate large-volume ePCR (e.g., performing ePCR in large volumes). Samples processed by the ePCR system may be further subjected to sequencing by one or more sequencers. For example, the sample may be processed by the ePCR methods and systems provided herein before being loaded on a sequencing machine. In some cases, the timing requirement of the ePCR system may be configured to match a timescale of a sequencing machine that may be used in combination with (e.g., after) the methods provided herein. In some cases, the output of the ePCR device may feed more than one sequencing machine, such as 2, 3, 4, 5, or more sequencing machines. Example sequencing systems that can be used with the ePCR system described herein are described in, e.g., U.S. Patent Pub. No. 2021/0079464 and International Patent Pub. No. WO2020/118172, each of which is entirely incorporated herein by reference.

The systems and methods may comprise one or more modules and/or procedures. For example, there may be 1, 2, 3, 4, 5, 6, 7, 8, 9, 10, or more modules. A simplified schematic of an example workflow which may be used to perform the methods of the present disclosure (e.g., any process or reaction described herein, such as ePCR) is shown in FIG. 1. The modules or procedures may be used or performed in a given order. For example, the first module 101 may be first in the sequence of modules or procedures, the second module 102 may be used or performed after the first module 101 and before the third module 103, and so on. Alternatively, the modules may be performed in different orders. For example, another module other than the first module 101 is used to perform a procedure on the sample first. In another example, the fourth module 104 is performed before the second module 102. In another example, multiple modules are used in parallel or substantially simultaneously. Various sequences and workflows can be used and optimized as suitable.

The first module 101 may comprise methods and systems for emulsion formation. Emulsion formation may comprise generating a plurality of partitions such as droplets. For example, a sample may be compartmentalized in a plurality of droplets. The droplets may be any droplets described elsewhere herein. For example, the droplets may comprise aqueous droplets in an immiscible oil phase. Droplets may be formed using various techniques. In some examples, the first module may comprise or be a microfluidic device. Alternatively, droplets may be formed without the aid of a microfluidic device. In some examples, droplets may be formed by adding an immiscible oil to an aqueous sample in a container (e.g., a tube or any container of any shape or form), or vice versa where an aqueous sample is added to the immiscible fluid, and subjecting the container to agitation on a platform, block, vortex, or other system. An example of such system is shown as system 1710 in FIG. 17 or system 1810 or system 1820 in FIG. 18. The first module 101 may comprise a system or portion of a system comprising a container or a plurality of containers such as wells or chambers (e.g., a custom 96-well array plate of suitable characteristics described herein). The first module 101 may comprise a cartridge which comprises a plurality of containers (e.g., cartridge 540 in FIG. 5A). In an example, a sample of about 96 ml or 100 mL in volume is distributed among the wells or chambers of the cartridge, for example, to distribute 1 mL per well (96×1=96 mL). In other examples, other volumes of samples are distributed among the wells or containers of the cartridge (e.g., evenly or unevenly) to be processed using the modules and procedures provided herein.

The first module 101 may comprise systems and methods for providing an immiscible fluid (e.g., oil) in addition to the sample (e.g., aqueous sample) in the containers (e.g., in the cartridge 540) and subjecting the cartridge to agitation. An example schematic of emulsion formation is shown in FIG. 2. An aqueous sample 240 and an oil 220 which may be immiscible with the sample may be provided in a container (e.g., in the cartridge 540). The container may be subjected to agitation to generate an emulsion 260 of aqueous droplets in the oil in the container. This agitation or shaking may be facilitated by a shaking platform that subjects the container (or its contents) to agitation. The shaking platform may be mechanically coupled to the container, a cartridge (e.g., cartridge 540) comprising the container, a cartridge holder, or any system or device, or portion thereof mechanically coupled to the container. In some cases, the shaking platform may be integrated with a heat exchange system 500 or mechanically coupled to the system 500. Agitation may be provided at a speed of at least about 1000 revolutions per minute (RPM), 1500 RPM, 2000 RPM, 2500 RPM, 3000 RPM, 3500 RPM, 4000 RPM, 4500 RPM, of a moving component or more. Alternatively or in addition, agitation may be provided at a speed of at most about 7000 RPM, 6000 RPM, 5000 RPM, 4500 RPM, 4000 RPM, 3500 RPM, 3000 RPM, 2500 RPM, 2000 RPM, 1500 RPM, of a moving component or less. This agitation may create shear forces in the fluid contained in the container to form aqueous droplets of suitable sizes. Droplet sizes may be according to any droplet size described elsewhere herein. In some examples, droplet sizes may be at least about 1 micron, 2 microns, 3 microns, 4 microns, 5 microns, 6 microns, 7 microns, 8 microns, or more, in diameter. In some examples, droplet sizes may be at most about 10 microns, 9 microns, 8 microns, 7 microns, 6 microns, 5 microns, 4 microns, 3 microns, or less in diameter. In some cases, the droplets may be surrounded by a surfactant which can help keep them stable during any of the processes described herein (e.g., during droplet formation, during thermal cycling, etc.). Surfactant may be included in the immiscible oil. The amount of surfactant may be optimized to achieve droplets of suitable stability based on the given application.

With continued reference to FIG. 1 and FIGS. 5A-5D, the second module 102 may comprise a heat exchange system 500 for heat transfer. The heat exchange system 500 may comprise a thermocycler 510, fins 530, trough-like cavities 532 between each pair of neighboring fins for receiving reaction wells, cartridge 540, lid 550, a seal 560, and one or more holes 580. The heat exchange system 500 may be configured to receive cartridge 540 (e.g., a 96-well plate provided herein), and bring the cartridge in contact with thermocycler 510 to subject the sample in the cartridge to thermal cycling, such as to perform a PCR reaction (e.g., ePCR). The second module 102 may be configured to heat the sample to a predefined temperature or temperature threshold, maintain the sample in the predefined temperature or temperature threshold, cool down the sample to a predefined temperature or temperature threshold, maintain the sample at a predefined temperature or temperature threshold for a predefined period, and any combination thereof. In some cases, the second module 102 may be configured to subject the sample to thermal cycling. The second module of the one or more modules may occur subsequent to the first module 101.

The thermocycler 510 may comprise a metal block. The metal block may comprise one or more ridges or indentations. The ridges may be configured to contact, interact with, or support one or more containers of cartridge 540. A heat exchange system or apparatus of any kind, such as the methods and systems for heat transfer described herein, may be used to change or cycle the temperature of the thermocycler 510. In some examples, it may take at least about 10 seconds (s), 15 s, 20 s, 30 s, 35 s, 40 s, 45 s, 50 s, 55 s, 60 s, 65 s, 70 s, or more to change the temperature of the sample to a predefined temperature or temperature threshold inside the container. In some examples, the thermocycler may not comprise a metal block.

In some examples, thermal cycling may be performed using one or more peltiers or peltier-driven thermal cyclers. Peltier-driven thermal cycling may comprise controlling or adjusting the temperature of a metal block (e.g., electrical peltiers) to a suitable temperature and using it to subject the sample to thermal cycling (e.g., to perform a PCR reaction such as ePCR).

In some examples, thermal cycling may comprise moving a sample, manually or automatically, between fluid baths of various temperatures, thereby subjecting the sample to a set of heating and cooling cycles (e.g., thermal cycling). For example, a robotic arm may be used to move the sample between a number of water baths set at different temperatures to subject the sample to thermal cycling. The fluid baths may be precisely temperature-controlled and their temperatures may be modulated to the temperatures of the PCR reaction. The fluid baths may comprise one or more water baths, such as 2, 3, 4, 5, 6, 7, 8, 9, 10, or more water baths.

In an aspect, provided herein is a system, comprising: a thermocycler comprising (i) a plurality of fins configured to receive a cartridge comprising a plurality of containers between at least a subset of the plurality of fins and (ii) a fluid channel in thermal communication with the plurality of fins. A cavity defined by at least two of the plurality of fins may be configured to receive therein at least two containers of the plurality of containers. The system may further comprise a controller operably coupled to the thermocycler. The controller may be configured to, when the plurality of containers is received by the thermocycler, (i) subject a gap between respective walls of the at least two containers and respective walls of the cavity to negative pressure, thereby creating a vacuum to decrease a distance of the gap, and (ii) subject fluid to flow through the fluid channel, thereby thermocycling a sample in the plurality of containers.

Figure 5C:
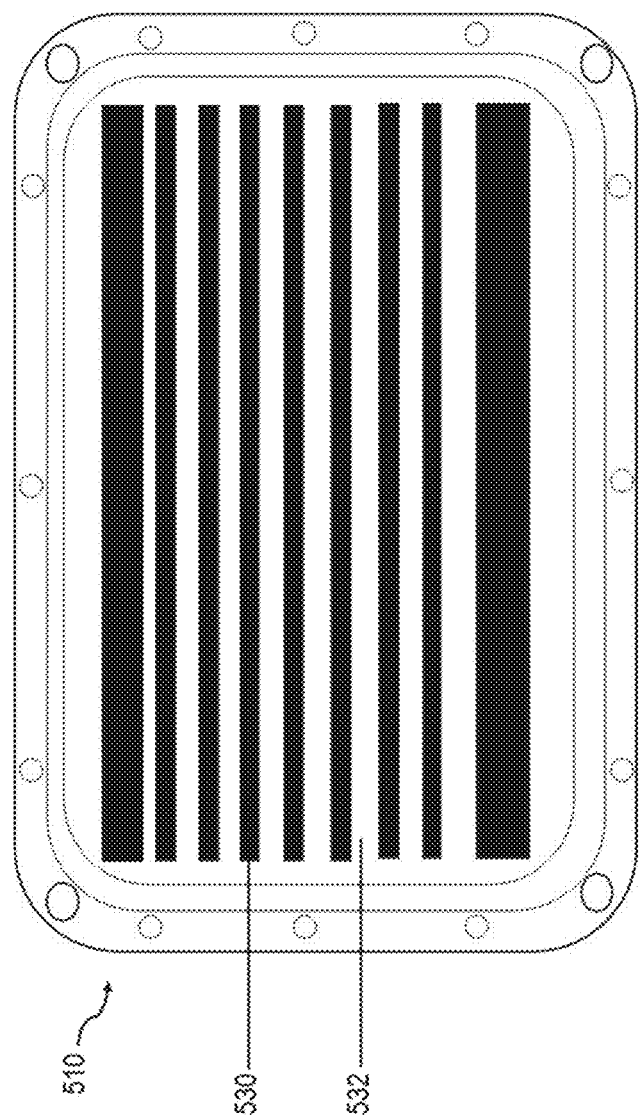
FIG. 5C shows a view from the top of example fins in the systems provided herein.

Examples of a plurality of fins configured to receive a cartridge comprising a plurality of containers are shown in FIGS. 5A, 5B, and 5C. For example, FIG. 5A shows a plurality of fins 530 configured to receive a cartridge 540. Cartridge 540 may comprise a plurality of containers described in further detail elsewhere herein. FIG. 5B shows an example of the fins 530 receiving the plurality of the containers 534 of the cartridge. A cavity 532 may be defined between at least two of the plurality of the fins 530 and may be configured to receive at least two containers 534 of the plurality of containers of the cartridge 540. FIGS. 5E-5F show a top perspective view and bottom perspective view, respectively, of an example of a sample cartridge. For example, the sample cartridge may comprise twelve containers in each row for receipt in each cavity (e.g., 532) defined by the fins (e.g., 530), with eight such rows of containers for receipt in eight cavities. FIGS. 5G-H show a top perspective view and bottom perspective view, respectively, of another example of a sample cartridge. For example, the sample cartridge may comprise eight containers in each row for receipt in each cavity (e.g., 532) defined by the fins (e.g., 530), with twelve such rows of containers for receipt in twelve cavities. Embodiments and views of a sample cartridge are also described in U.S. Design patent application No. 29/740,346, which is entirely incorporated herein by reference for all purposes.

Figure 5D:
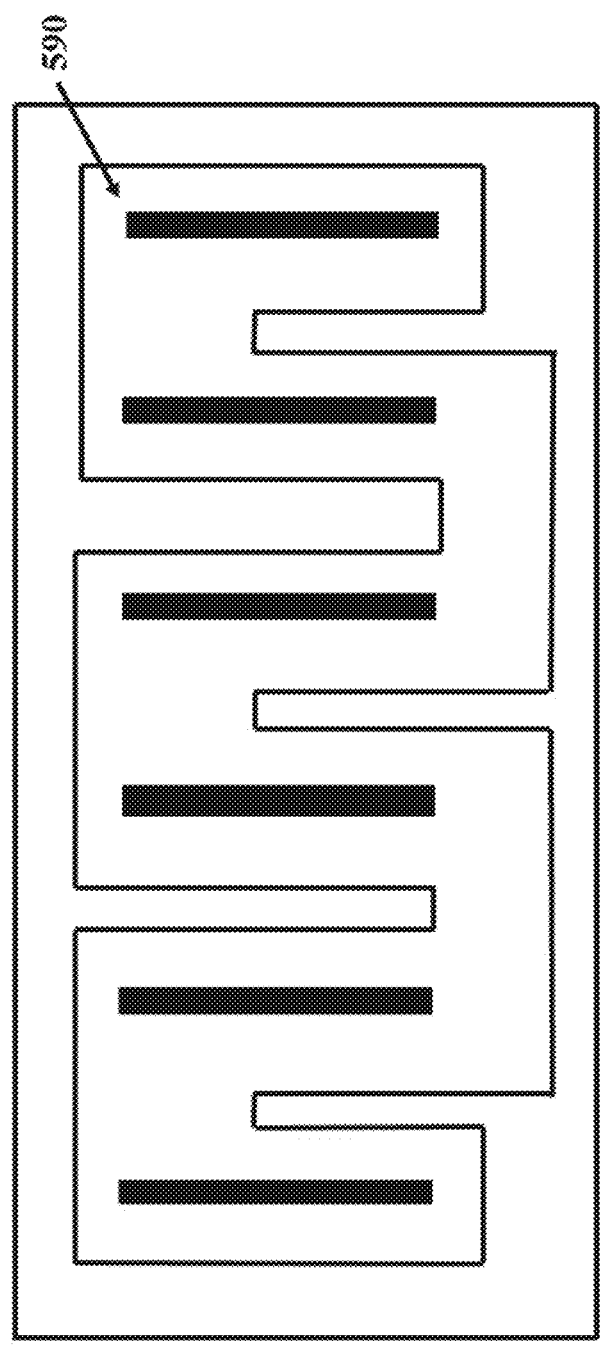
FIG. 5D shows a view from the top of example fluid channels provided herein.
Figure 5F:
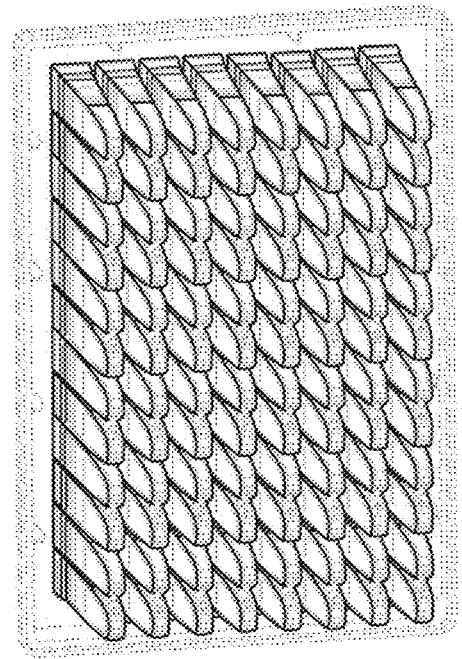
FIGS. 5E-5F show a top perspective view and bottom perspective view, respectively, of a sample cartridge.
Figure 5E:
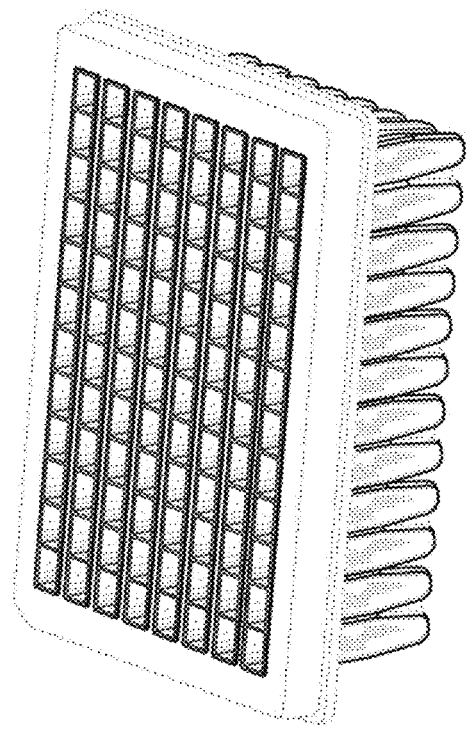
Figure 5H:
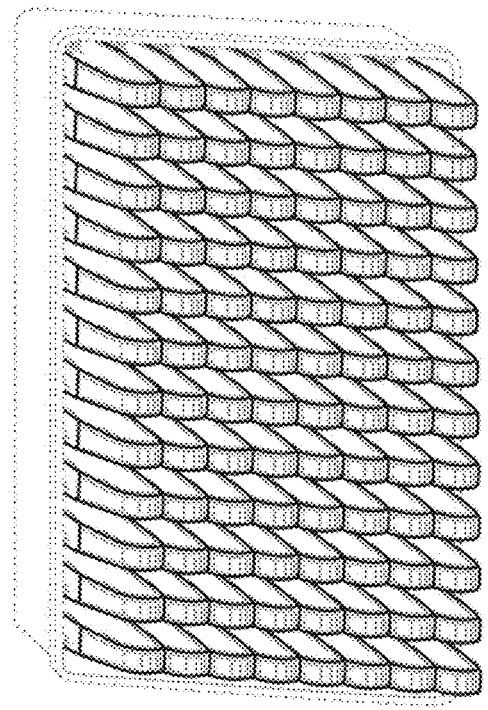
FIGS. 5G-5H show a top perspective view and bottom perspective view, respectively, of another sample cartridge.
Figure 5G:
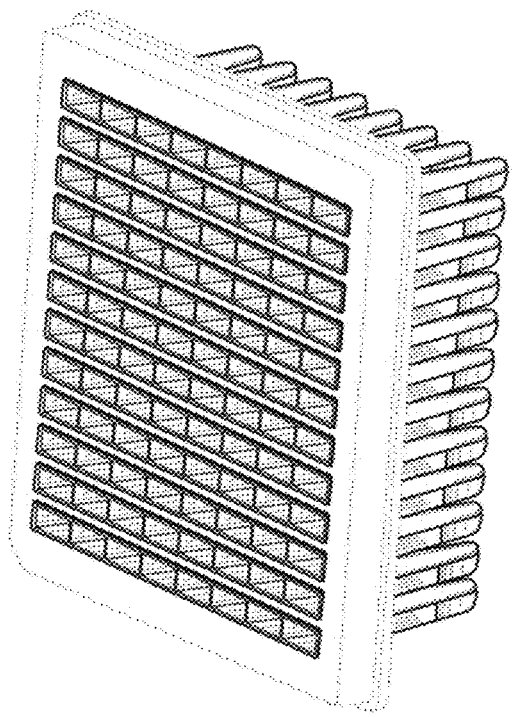

The system may further comprise a fluid channel, such as fluid channel 590 shown in FIG. 5D which may be in fluid communication with the fins. For example, fluid channel 590 may be placed underneath the fins.

In some examples, the plurality of thermal fins may comprise or be made of metal. Metal may comprise any metal, in some examples, aluminum. The system may further comprise a lid (e.g., lid 550 shown in FIG. 5A) which may be configured to close the thermocycler. The controller may be operably coupled to the lid and configured to maintain the lid at a temperature or temperature threshold.

In some examples, the system further comprises the cartridge. The plurality of containers may be a plurality of wells, tubes, or any other container of any shape or form, such as the containers or tubes described anywhere herein. In some examples, a container of plurality of containers may configured to hold at least 1 milliliter (1 mL) of fluid. In other examples, the container may hold any other volume provided elsewhere herein. In some examples, the cavity 532 is configured to receive therein at least four containers of the plurality of containers. In some examples, the cavity is configured to receive therein at least eight containers of the plurality of containers. In some examples, the cavity is configured to receive therein at least twelve containers of the plurality of containers. In some examples, the cavity may be configured to hold at least 1, 2, 3, 4, 5, 6, 7, 8, 9, 10, 12, 14, 16, or more containers.

In some examples, such as shown in FIG. 5B, a plurality of cavities 532 may be defined by the plurality of fins 530, wherein each cavity 532 of the plurality of cavities may be configured to receive at least two containers 534 of the plurality of containers. In some examples, each cavity 532 of the system (e.g., formed between the fins) may be configured to receive any number of containers provided anywhere herein.

In some example, such as shown in FIG. 5B, the plurality of cavities 532 may be disposed as an array of substantially parallel lanes of cavities. In some examples, the cavity may comprise one or more features (not shown) configured to guide individual containers of the at least two containers within the cavity. In some examples, the one or more features may be coupled to one or more walls of the plurality of fins. In some examples, the one or more features are integrated with one or more walls of the plurality of fins. For example, the features may comprise curved walls and/or surfaces. In some cases, features may comprise dented features.

In some examples, the cavity 532 comprises a first substantially planar wall, and a container of the at least two containers comprises a second substantially planar wall configured to interface the first substantially planar wall. See examples of such substantially planar walls of containers in FIGS. 5E-5H. A cavity may be defined by two substantially planar walls, where each container of a sample cartridge is configured to interface one or both of the substantially planar walls. For example, a container may comprise at two substantially planar walls opposing each other, the two substantially planar walls configured to interface the two substantially planar walls defining the cavity, when the continue is received by the cavity. A gap between the cavity walls and the container walls may exist between any two interface points, for example, there may be two gaps, one between each cavity wall-container wall pair. Upon application of negative pressure to the gap(s) (e.g., vacuum), the distance of a single gap may decrease. Alternatively, the respective distances of a plurality of gaps may decrease. Alternatively or in addition, the respective distances of each gap may decrease.

In an aspect, provided herein is a method of sample processing comprising: (a) providing a thermocycler comprising (i) a plurality of fins (e.g., fins 530) configured to receive a cartridge (e.g., cartridge 540) comprising a plurality of containers (e.g., containers 534) between at least a subset of the plurality of fins and (ii) a fluid channel (e.g., channel 590 shown in FIG. 5D) in thermal communication with the plurality of fins, wherein a cavity defined by at least two of the plurality of fins is configured to receive therein at least two containers of the plurality of containers; (b) receiving a cartridge comprising a plurality of containers between at least a subset of the plurality of fins in the thermocycler, wherein a container of the plurality of containers comprises a sample; and (c) thermocycling the sample by (i) subjecting a gap between respective walls of the at least two containers and respective walls of the cavity to negative pressure, thereby creating a vacuum to decrease a distance of the gap, and (ii) subjecting fluid to flow through the fluid channel, thereby thermocycling a sample in the plurality of containers.

As shown in FIG. 5A, the heat exchange system 500 may comprise a thermocycler 510. An entering stream of fluid 520 may flow into the thermocycler to change its temperature and later exit the thermocycler as an exit stream of fluid 570. The entering stream of fluid 520 may comprise a temperature higher than the initial temperature of the thermocycler 510 and can thereby increase the temperature of the thermocycler 510 by flowing through it. Alternatively, the entering stream of fluid 520 may comprise a lower temperature compared to the initial temperature of the thermocycler 510 and can thereby decrease the temperature of the thermocycler 510 by flowing therein. Fluid may flow in one or more fluid lines outside and/or inside the thermocycler. Fluid lines may comprise pipes, channels, conduits, or any other paths for fluid flow. Fluid lines may be insulated with an insulating material (e.g., outside the thermocycler. The thermocycler may receive fluids at distinct temperatures from distinct fluid sources, such as separate tanks.

The thermocycler 510 may comprise or be connected to (e.g., located on top of) a fluid channel 590. An example of a fluid channel 590 that may be coupled to or be comprised in the thermocycler 510 is shown in FIG. 5D. The fluid channel 590 may comprise or be a path for fluid flow in which the fluid streams (520 and 570) may flow. The fluid channel 590 or path shown in FIG. 5D, may be underneath fins 530 (also shown in FIG. 5C). FIG. 5C shows a view from the top of the fins 530. By alternating the temperature of the fluid flowing in fluid path, the temperature of the fins 530 can be changed. The fins 530 which may be made of a material with high thermal diffusivity may conduct the heat from a hot fluid to the cartridge 540 and sample, or may be cooled down by a cold fluid, and thereby decrease the temperature of the cartridge 540 and the sample inside the cartridge. As such, the temperature of the sample could be changed, and/or be subjected to thermal cycling by switching between hot and cold streams of fluid in the fluid path (e.g., the fluid path shown in FIG. 5D).

The heat exchange system 500 may further comprise one or more fins 530 (also shown in FIG. 5C). Fins may be made of a material with a high thermal diffusivity to conduct heat from the thermocycler 510 to the sample, such as the sample contained in the cartridge 540. The material used in the fins may comprise aluminum, copper, bronze, brass, silver, gold, titanium, iron, nickel, or any combination or alloy thereof with any composition. In some examples, the material used in the fins may be aluminum. A view from the top of the fins 530 is shown in FIG. 5C. It will be appreciated that the fins may be arranged in any suitable configuration. For example, the fins 530 may comprise any number of fins, such as 1, 2, 3, 4, 5, 6, 7, 8, 9 10, 11 12, 13, 14, 20, 30, 40, 50, 60, 70, 80, 90, 100 or more fins in any shape, size, or configuration.

Fins may be designed to receive tubes, containers, or wells of different shapes. In some cases, the architecture, shape, and/or size of the fins and features thereof may be designed to match the shape of a given container. In some examples, such as the examples shown in FIGS. 5A and 5B, the tubes and fins may have flat surfaces that interface when the tubes are received by the fins. The tubes may fit well in the fins, such as to enable a tight clearance fit, prior or subsequent to vacuum. Vacuum may further enhance the contact between the wells and the fins. In other examples, the tubes may have curved walls. The tubes may comprise any shape, form, or size, such as the shapes and sizes described elsewhere herein. In some cases, tubes or containers may comprise curved surfaces. In such examples, the fins may also comprise one or more curved and/or dented features in which may match the shape and size of the tubes and may guide or facilitate proper contact between the tubes and the fins and prevent the sliding of the fins and/or cartridges within cavities defined by the fins. The features may be coupled to one or more walls of the fins. Alternatively or in addition, the features may be integrated in one or more walls of the fins. The features may protrude from a planar surface of a wall. Alternatively or in addition, the features may intrude into a planar surface of a wall.

A reaction vessel or cartridge, such as cartridge 540 may be brought into contact with the fins 530. In some examples, the cartridge 540 used in the second module 102 (shown in FIG. 1) in combination with the heat exchange system may comprise a cartridge or an array plate provided elsewhere herein. In one particular example, the cartridge 540 may comprise an array plate comprising 96 wells or chambers (or any other number of wells), made with a thermoplastic material such as Polypropylene or any other suitable material. The cartridge 540 may be thin-walled to enhance heat transfer to the sample. For example, the thickness of the walls of the cartridge 540 may be between 0.1 mm to 1 mm, in some cases, between about 0.3 to 0.6 mm. Alternatively, the cartridge may be according to the cartridges and well plates provided anywhere herein.

In some examples, a heat exchange system may comprise one or more cartridges, such as 1, 2, 3, 4, 5, 6, 7, 8, 9, 10, or more cartridges. In a particular example, a heat exchange system may comprise 2 cartridges that may be arranged side-by-side. Alternatively, the heat exchange system may comprise more than two cartridges that may be arranged in any suitable configuration. A system comprising more than one cartridge may comprise a higher number of fins compared to a system comprising one cartridge. Increasing the number of fins and cartridges (e.g., doubling the number of fins and cartridges) may increase the total throughput of the system and methods such as thermocycling throughput (e.g., double the thermal cycling throughput).

Referring to FIG. 5A, in some cases, cartridge 540 may be held tight in place on heat transfer fins 530. For example, the containers or chambers of the cartridge may be interlaced between heat transfer fins that conduct heat from the thermocycler (also referred to herein as a thermocycle block, thermocycling block, or thermocycler block). This may facilitate better heat transfer, avoid energy loss, and enhance the efficiency of the heat transfer, reaction, and/or process. For example, multiple reaction chambers of cartridge 540 can be arranged a linear array 542 and received in a trough-like cavity 532 between heat transfer fins 530. The trough-like cavity 532 is sized and shaped to ensure good fitting between heat transfer fins 530 and linear array 542. In some embodiments, linear array 542 and trough-like cavity 532 may have complementing cross-sectional surfaces, including but not limited to a rectangle, a square, a rounded triangle, or a trapezoid (acute, right, isosceles, or 3-sides equal). In some embodiments, reaction chambers within an array are partially connected (e.g., at the top). Between adjacent arrays 542 is a downward trough-like cavity 544. Similarly, downward trough-like cavity 544 is also shaped and sized to accommodate a heater transfer fin 530. In some embodiments, heat transfer fins 530 and downward trough-like cavity 544 may have complementing cross-sectional surfaces, including but not limited to a rectangle, a square, a rounded triangle, or a trapezoid (acute, right, isosceles, or 3-sides equal). In some embodiments, the downward trough-like cavity 544 is an isosceles trapezoid where the angle formed by the side and height of the trapezoid is between 1 and 10 degrees, between 1.5 and 8 degrees, between 2 and 6 degrees, or between 2.5 and 4 degrees. As disclosed here, a limit in each range can be within a certain error limit; e.g., ±0.5 degree, ±0.4 degree, ±0.3 degree, ±0.2 degree, ±0.1 degree, ±0.05 degree, or even smaller. For example, an angle range between 2 and 6 degrees can cover anything between 1.5 to 6.5, 1.6 to 6.4, 1.7 to 6.3, 1.8 to 6.2, 1.9 to 6.1, down to 1.95 to 6.05.

In some examples, the cartridge 540 (e.g., a thin-walled consumable array plate of suitable size, shape or form) may be tightened against the heat transfer fins 530 using mechanical parts and/or pieces, such as screws, holes, or other tools. In some example, a chemical, such as glue may be used to tighten the cartridge 540 to the fins 530. In some examples, the cartridge may be removably attached or held on or adjacent to the fins. In some cases, the cartridge may be permanently attached to the fins. Alteration to the system may be made to achieve set goals and objectives for the reaction and/or process.

In some examples, a vacuum may be applied which may hold the cartridge 540 tight in place on or adjacent to the fins 530 or otherwise stabilize the support. The vacuum may comprise a partial vacuum. The vacuum may comprise any pressure. In some cases, a vacuum may comprise a pressure of at most about 14.7 pounds per square inch (psi). In some cases, a vacuum may comprise a pressure of at most about 14.5 psi, 14 psi, 13.5 psi, 13 psi, 12.5 psi, 12 psi, 11.5 psi, 11 psi, 10.2 psi, 10 psi, or less. The vacuum may strengthen or enhance the thermal contact between the cartridge and the fins. For example, the gap between the cartridge (e.g., a consumable plate) and the fins may be subject to negative pressure. In some cases, the cartridge (e.g., consumable plate) may comprise thin walls and may be deformable. For example, the cartridge may be made of polypropylene or a material mentioned elsewhere herein. The vacuum may pull the cartridge (e.g., plate) down. In some cases, vacuum may also deform the walls of the plate outward. This may further enhance the contact of between the containers of the cartridge and the fins. In some cases, vacuum may prevent the walls from caving in. In some cases, vacuum may prevent the cartridge from sliding. In some embodiments, vacuum is applied and maintained throughout a reaction cycle; for example, through each reaction cycle. In some embodiments, vacuum is applied only for part of a reaction cycle.

The methods provided herein may comprise detaching the plate from the heat exchange system (e.g., from the fins). The vacuum may be removed, so that the plate can be released. In some cases, the method may further comprise applying a positive pressure to facilitate or at least partially assist with detaching the plate from the heat exchange system. In some cases, the method may further comprise providing one or more devices to facilitate detaching the cartridge from the heat transfer system. The one or more devices may be configured to apply one or more forces comprising pressure (e.g., positive pressure), mechanical forces, magnetic forces, electrical forces, or other forces to facilitate removing and/or detaching the cartridge from the heat exchange system.

In some cases, the heat exchange system, or parts of the heat exchange system may be moved or shaken to provide agitation, mixing, or turbulence in the system. Increasing turbulence in the heat exchange system may increase the rate of heat transfer as well unifying and homogenizing heat transfer therein. In some example, the thermocycler 510 may be agitated at a speed of at least about 50 rotations per minute (RPM), 100 RPM, 200 RPM, 300 RPM, 400 RPM, 500 RPM, 600 RPM, 700 RPM, 800 RPM, 900 RPM, 1000 RPM, 1100 RPM, 1200 RPM, 1300 RPM, 1400 RPM, 1500 RPM, 1600 RPM, 1800 RPM, 2000 RPM, 2500 RPM, 3000 RPM, 3500 RPM, 4000 RPM, 5000 RPM, or more. The agitation speed may depend on application.

In some examples, shaking is performed for heat transfer, mixing, and/or uniformity purposes. For example, shaking may unify or homogenize the contents of each container by mixing. Shaking and/or mixing may promote heat transfer in the containers. Beneficially, the agitation or shaking may increase the convection coefficient to promote heat transfer. Alternatively or in addition, shaking or agitation may be performed for emulsion formation. The rate of agitation or shaking may depend on the application and outcome. For example, in some cases, the rate of shaking may be faster for emulsion formation compared to agitation for heat transfer purposes (e.g., mixing). In one particular example, the agitation speed (e.g., for thermal cycling) may be about 1000 RPM. In another example, the agitation speed (e.g., for emulsification or droplet breakup) may be at least about 2000 RPM.

Agitation or shaking may be performed using a shaking platform. Shaking platform may comprise a surface on which the heat exchange module may be placed, and thereby facilitating shaking the heat exchange system 500 and/or the thermocycler 510.

In some examples, emulsion generation may comprise adding an aqueous sample and an oil in a container and subjecting the container to agitation. The ratio of oil to aqueous phase may in some cases affect the droplet size. In some examples, the oil to sample ratio may be about 3:1. In other examples, this ration may be 2:1, 4:1, 5:1, or other ratios. The oil to sample ratio may depend on various factors such as the contents of the oil and sample, temperature, equipment and method of emulsion generation, and more. The ratio can comprise any suitable ratio in each case and can be optimized according to the varying factors. Each condition of emulsion generation may result in a droplet size distribution. In some examples, including beads in the aqueous sample may result in a suitable droplet size distribution. In some examples, a droplet size of between about 2.5 microns to 6 microns, or, for example, droplet sizes of about 3.5 microns may be generated.

The view from the top of the example system shown in FIG. 5A is illustrated in FIG. 5B. FIG. 5B shows rows of the cartridge 540 (e.g., consumable well plate) which may be alternated between the rows of the fins 530 of the heat exchange system 500. The cartridge can have any configuration, for example, a 12×8=96 well plate configuration. Alternatively, the cartridge can comprise any number of wells and any configuration. In some embodiments, the cartridge comprises 8 horizontal rolls, each roll including 12 partially connected reaction chambers. Each roll of reaction chambers is received in a trough-like cavity 532 between two adjacent heat transfer fins 530 (see, e.g., FIG. 5A and FIG. 5C). In some embodiments, the cartridge comprises 12 vertical columns, each column including 8 partially connected reaction chambers. For examples, instead of being arranged horizontally as shown in FIG. 5C, heat transfer fins 530 and trough-like cavity 532 can be arranged in vertical orientation as shown in FIG. 5A (depicting 11 columns being received in 11 troughs). The reaction chambers can be arranged in any number of rolls or columns. In some embodiments, the reactions chambers can be arranged into non-linear patterns, including but not limited to circles, ovals, semi-circles, triangles, rectangles, squares and more. In some embodiments, cartridge 540 can include a skirt structure at the top extending outward and covering the top portion of the reaction chambers. The skirt-like design can provide extended side surfaces for easy handling of the cartridge, for example, by an automated system.

The heat exchange system 500 may further comprise a seal 560 on the cartridge. For example, the cartridge 540 may be sealed using the seal 560 on top of the cartridge 540 and containers thereof to keep the sample contained in the container and isolated from the environment until the seal 560 is removed (e.g., after the reaction or process is completed). The seal 560 may comprise or be a film. The seal 560 film may be made of any material, such as aluminum. In some cases, the seal 560 may be made of aluminum foil further comprising a Polypropylene laminate. For example, the seal may cover the containers (e.g., array plate). In an example, the array plate comprising a plurality of reaction vessels or containers may comprise a seal. The array plate may be sealed down, for example, it can be a closed system during the operation. This may reduce the time and energy needed for thermal cycling because thermal mass and contact resistance can be decreased or substantially eliminated.

The heat exchange system 500 may further comprise a lid 550. The lid 550 may comprise one or more holes 580. The holes may facilitate access to the containers as needed, for example, by pipettes, needles, robotic handlers, hand, etc. In some cases, the lid may be configured to be heated. The lid may comprise or be made of any material. In some cases, the lid may comprise or be made of a metal. Metal may comprise iron, silver, aluminum, copper, bronze, brass, any other metal, and/or any combination or alloy of the mentioned metals. In some examples, the lid may be heated using a heater, such as a resistance heater, or any other kind of heater to a temperature of at least about 40° C., 50° C., 60° C., 70° C., 80° C., 90° C., 100° C., or more. The heated metal lid may be placed on top of the cartridge 540 as shown in FIG. 5A. This may prevent condensation and provide or allow for a more even temperature distribution.

In some examples, the heat exchange system may comprise a non-contact lid. For example, air (e.g., hot air) may be blown over top of the collection of containers (e.g., array plate) to seal it. In an example, the heat exchange system may comprise a heated block. The heated block may sit above the containers (e.g., plate) and may heat the thin film of air above the containers. In some cases, the containers (e.g., array plate) may be pressed down. Pressing the plate down may be accomplished by mechanical tools such as a gripper, or other tools and/or techniques. In some cases, vacuum pull may get engaged and the plate or containers may be secured.

Figure 4:
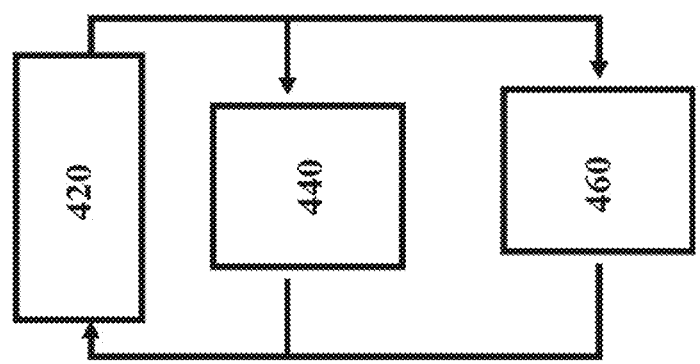
FIG. 4 shows an example workflow for performing the methods of the present disclosure.

Provided herein are methods and systems for thermocycling. In some examples, the systems for thermocycling may comprise the heat exchange transfer system 500 (e.g., heat transfer system) shown in FIG. 5A. The heat transfer system may comprise a thermocycler 510. In some examples, the thermocycler may be in communication with one or more reservoirs or tanks. For example, a reservoir may comprise a tank comprising liquid at a defined temperature. A schematic of an example workflow for thermocycling is shown in FIG. 4. Provided is a system 400 for thermocycling which may comprise a thermocycler 420 which may be in communication with one or more heat reservoirs (440 and 460). In some examples, the thermocycler 420 (in FIG. 4) may be the same as the thermocycler 510 (in FIG. 5A). Each of the one or more reservoirs may be set at a given temperature. For example, reservoir 440 may be set at temperature T1, and reservoir 460 may be at temperature T2. The temperature of the reservoirs may depend on the target temperature of the sample or emulsion. In one particular example, the sample may need to reach a temperature of about 96° C. In this example, the temperature of a hot tank may need to be set to about 105° C. In an example, the sample may be targeted to be cooled down to a cold temperature of about 68° C. In this example, the temperature of a cold tank may be set to a temperature of about 62° C. The temperatures of the tanks in each example may be calculated using principles of heat transfer. In some examples, the platform comprising the heat transfer equipment, the cartridge, and other parts may be entirely or partially moved or shaken (e.g., at a temperature of about 1000 RPM) to enhance the heat transfer. Alternatively or in addition, shaking speeds may be adjusted based on the application, for example, according to the methods provided elsewhere herein.

An example reservoir or tank may comprise any size or volume. In some examples, the volume of the tank may be about 3 gallons. In some examples, the volume of a reservoir or tank may be at least about 0.5 gallon, 1 gallon, 1.5 gallons, 2 gallons, 2.5 gallons, 3 gallons, 3.5 gallons, 4 gallons, 4.5 gallons, 5 gallons, or more. In some examples, the volume of the reservoir or tank may be at most about 10 gallons, 8 gallons, 7 gallons, 6 gallons, 5 gallons, 4 gallons, 3.5 gallons, 3 gallons, 2 gallons, 1.5 gallons, 1 gallon, or less.

Provided herein is a system (e.g., system 300 shown in FIG. 3) comprising a first fluid source container (e.g., reservoir 320), which may be configured to maintain fluid at a first temperature or first temperature range; a second fluid source container (e.g., reservoir 3600), which may be configured to maintain fluid within at a second temperature or second temperature range different from said first temperature or temperature range. The system (e.g., system 300) may further comprise a thermocycler (e.g., thermocycler 380). The thermocycler 380 may be similar to the heat exchange system 500 shown in FIGS. 5A-5D. The thermocycler (e.g., thermocycler 380) may comprise a plurality of fins (e.g., similar to fins 530 shown in FIG. 5A and FIG. 5C) and a fluid channel (e.g., similar to channel 590 shown in FIG. 5D) which may be in thermal communication with the plurality of fins (e.g., fins 530). In some cases, the fluid channel (e.g., channel 590) of the thermocycler (e.g., thermocycler 380 shown in FIG. 3) may be fluidically connected to the first fluid source container (e.g., reservoir 320) and the second fluid source container (e.g., reservoir 3600). In some examples, the thermocycler (e.g., thermocycler 380 shown in FIG. 3 or thermocycler 510 shown in FIG. 5A) may be configured to receive a cartridge (e.g., similar to cartridge 540) which may comprise a plurality of containers between at least a subset of the plurality of fins (e.g., fins 530). The system may further comprise a controller which may be operably coupled to the thermocycler (e.g., thermocycler 380), the first fluid source container (e.g., reservoir 320), and the second fluid source container (e.g., reservoir 3600). The controller may be configured to, when the plurality of containers is received by the thermocycler, (i) subject a gap between the at least the subset of the plurality of fins and the plurality of containers (e.g., containers of the cartridge 540) to negative pressure, thereby creating a vacuum to decrease a distance of the gap, and (ii) subject fluid from the first fluid source container and the second fluid source container, in sequence, thereby thermocycling a sample in the plurality of containers, for example, inside a thermocycler similar to thermocycler 380 or inside the cartridge 540 of the heat exchange system 500.

Figure 3:
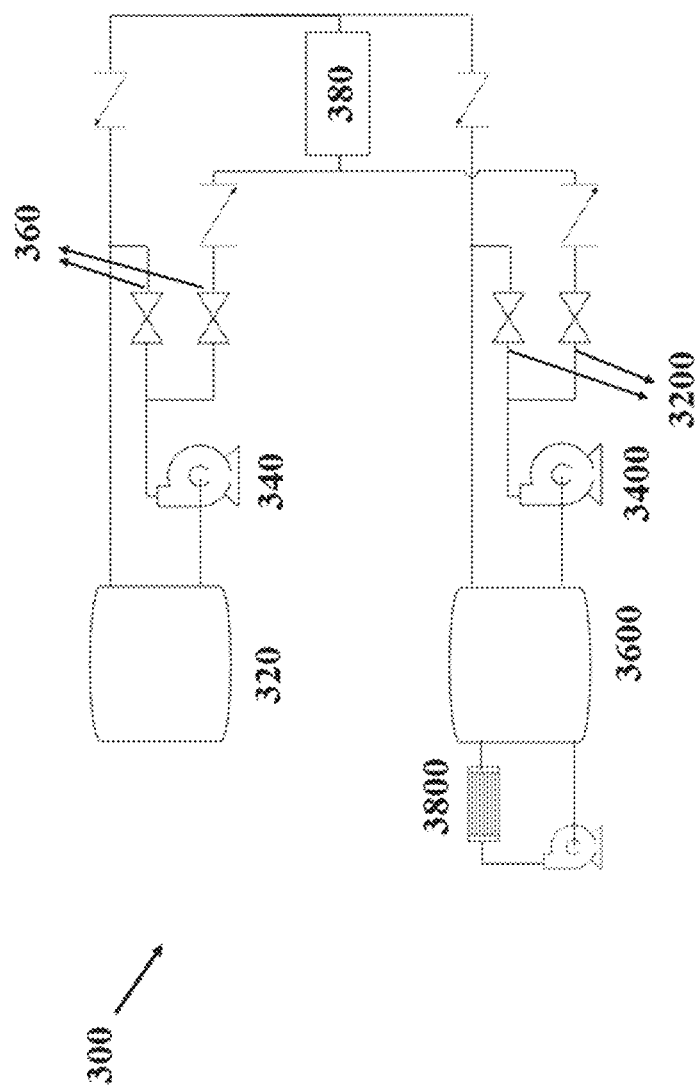
FIG. 3 shows an example system and process provided herein.

In some examples, the methods and systems for thermocycling may comprise a process or workflow, and/or facility. An example of a system and process 300 which may be used to perform thermocycling is shown in FIG. 3. The system 300 for thermocycling may comprise one or more reservoirs or tanks (e.g., 320 and 3600). The system 300 may further comprise one or more pumps (340 and 3400). The pumps may be configured to pump liquids from and to the reservoirs (320 and 3600). Optionally, the system 300 may further comprise one or more heat exchangers (3800). The heat exchangers may be configured to adjust the temperature of the liquids in the one or more reservoirs. In some cases, a pump may be used to facilitate fluid flow between the heat exchanger and the reservoir, for example through a pipeline. The system 300 may further comprise one or more valves (360 and 3200). Valves may be any kind of valves. In some examples, valves may be check valves. The system 300 may comprise a thermocycler 380. The thermocycler may be configured to subject a sample described herein to thermal cycling, for example to perform a PCR (e.g., ePCR). The valves 360 and 3200 (e.g., check valves) may be used to start and stop fluid flow through the pipe lines and in and out of the thermocycler.

With continued reference to FIG. 3, in an example workflow, the pumps (340 and 3400) may be running. For example, the pumps may be continuously running for an extended duration of time, and the valves (360 and 3200) may be configured to cycle hot and/or cold water to the block, and thereby subjecting a sample to thermocycling. For example, Reservoir 320 may be a hot tank. Reservoir 3600 may be a cold tank. Pumps may be on. One or more valves may be open and/or closed to let a hot fluid stream (e.g., from the hot tank 320) into the thermocycler 380, while one or more valves may be open and/or closed to stop a cold stream of fluid (e.g., from the cold tank 3600) to enter the thermocycler. One or more valves may be configured to let a stream from the cold tank 3600 circulate, for example in a closed loop without entering the thermocycler 380. This may help keep the cold tank mixed while it is not in use. In some cases, one or more valves (e.g., check valves) may be configured to prevent the hot and cold streams from mixing (e.g., in the pipelines or in any part of the system). Alternatively, in some cases, the hot and cold streams may be allowed to mix. For example, the system may be configured to let the two streams mix for some applications.

In some examples, the tanks may be switched, and cold fluid from the cold tank may be allowed in the thermocycler by one or more valves accordingly. Cold fluid passing through the thermocycler may cool down the temperature of the thermocycler and its contents (e.g., reaction vessels and samples therein). In some examples, the system may further comprise a control scheme for controlling (e.g., actively) flow rate of fluids to/from the pumps. The control scheme may comprise using computer systems and measurement tools. The control scheme may be according to any control scheme described elsewhere herein. Measurement tools and/or equipment may comprise any tool or piece of equipment which may be configured to measure a fluid flow in any point in the process (e.g., a flow generated by a pump). For example, the measurement tools and/or equipment may comprise one or more sensors (e.g., flow meter, flow sensor, etc.). The measurement taken by the measurement tool may be converted to a digital signal and further processed by the control scheme such as through computer systems.

In some examples, the method may comprise providing fine temperature control. In some cases, thermocycling may comprise cooling down the thermocycler to the cold temperature tank, heating the thermocycler to the hot temperature tank, and/or bringing the thermocycler to a temperature which is in the range between the temperature of the hot and cold tank, and may comprise mixing streams of fluid from the hot and cold tank (e.g., before cycling it through the thermocycler). In some examples, such mixing may be facilitated by one or more valves (e.g., mixing valves). For example, the system may further comprise one or more valves (e.g., mixing valves, not shown in FIG. 3) configured to mix a liquid from a hot tank (e.g., reservoir 320) with liquid from a cold tank (e.g., reservoir 3600). The valves (e.g., mixing valves) may be any suitable valves. In some examples, a valve suitable for mixing hot and cold liquids from the hot and cold tank/reservoir may comprise or be an electronically controlled valve. A suitable mixing valve may be a 3-way valve. In some cases, A mixing valve may be a controlled 3-way valve (e.g., electronically controlled). The method may further comprise mixing hot and cold liquids from the hot and cold reservoirs using the mixing valve. The method may comprise controlling the fluid mixing conditions, such as the temperature and flow rate of the fluids to be mixed, the timing of mixing, and other parameters. For example, the system may comprise equipment and/or tools for measuring fluid properties such as a temperature, a flow rate, a pressure, a concentration of a compound and/or any other relevant parameter as needed. The computer systems provided in FIG. 6 may be used to control a parameter such as mixing of fluids.

The method may comprise providing a process control scheme. The process control scheme may comprise methods for temperature control (e.g., fine temperature control) and controlling other characteristics of the process such as composition of fluids (e.g., comprising concentration of various compounds in each stream), temperature of fluids, pressure of fluidics, flow rates of different streams, timing of each event or change, and more. In some cases, a control scheme may comprise a feedback system. The control scheme may comprise measuring a parameter from a pre-defined point in the process and converting it to a digital signal. The control scheme may comprise a computer-readable medium such as code and/or algorithm (e.g., as described in FIG. 6) which may provide a feedback accordingly, such as to make or trigger a change in a predefined point or region in the process. In some cases, mixing of hot and cold fluids may at least partially contribute to providing temperature control (e.g., fine temperature control) to the process, such as to the thermocycling process performed in the cartridge. A more controlled and/or enhanced temperature control in the cartridge and/or containers may enhance the quality of products and/or results performed in the thermocycler, such as, in a PCR (e.g., ePCR).

In some examples, the system may further comprise one or more heaters (e.g., booster heaters). The booster heaters may facilitate heat transfer, for example, in addition to the tanks. In some cases, the amount of heat energy that the heaters provide to the system may be similar to the amount of heat provided by the tanks or less. In some cases, the heaters may provide significantly less heat compared to the tanks. The heaters (e.g., booster heaters) may have some advantages, such as convenient and/or efficient heat transfer and/or temperature control. Temperature control may be important during processes such as thermal cycling, for example at the denaturation temperature or other instances during the processes provided herein. The methods and systems may further comprise a control scheme. For example, a tank may be maintained at a given temperature (e.g., 94° C.), and may provide cooling to the system. In addition, booster heaters may provide heating to the system (e.g., in combination or as an alternative to hot tank). The system may comprise a controller which may turn on the heaters and/or the pumps (e.g., with variable flow rates) to facilitate heating and cooling. Such mechanism or procedure may reduce the pressure of the hot tank, and thereby prevent phase change in it.

In some examples, the methods of temperature control and/or thermocycling may comprise various combinations of the methods provided elsewhere herein. For example, the method may comprise using booster heaters, active flow rate control of the pumps, mixing liquids from the hot and cold tanks/reservoirs (e.g., with an electronically controlled 3-way valve) and/or any combination thereof.

Figure 17:
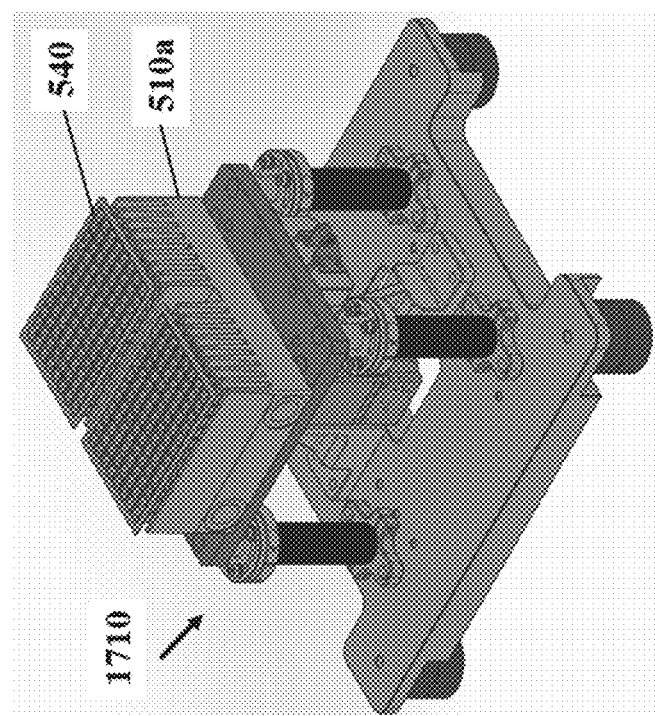
FIG. 17 shows a system or platform according to the methods of the present disclosure.

Though FIG. 5A illustrates a single cartridge (e.g., 540) being received and processed by a single thermocycling block (e.g., 510), it will be appreciated that the system (e.g., 500) may be adapted to process multiple cartridges in parallel. For example, as shown in FIG. 17, in system 1710, a single thermocycler block 510a is configured to receive two cartridges (e.g., two of cartridge 540) by comprising two sets of fins (e.g., 530) and troughs (e.g., 532) with each set being configured to receive a cartridge. FIG. 18 illustrates, on the left, in a system 1810, a single thermocycler block has received a single cartridge 540, and on the right, in a system 1820, a single thermocycler block has received two cartridges (e.g., two of cartridge 540). A single thermocycling block may be configured to any number of cartridges, such as 1, 2, 3, 4, 5, 6, 7, 8, 9, 10, 11, 12, 13, 14, 15, 16, 17, 18, 19, 20, or more cartridges. Alternatively or in addition, the system may comprise multiple thermocycling blocks each configured to receive one or more of a plurality of cartridges.

With reference to FIG. 1, the third module 103 of the one or more modules may comprise a method or system (or a set of methods and/or systems) for emulsion breaking. The third module 103 may facilitate breaking, coalescing, or disturbing one or more (e.g., a plurality of) partitions such as droplets (e.g., after they are formed and/or processed). In an example, droplets are formed in the first module 101, processed in the second module 102, and broken in the third module 103. Processing may comprise subjecting the droplets to conditions sufficient to perform a reaction such as ePCR. Breaking may comprise merging the droplets. For example, a plurality of droplets may be disrupted, and their contents may be rejoined and pooled. Emulsion breaking may be accomplished using various techniques, such as techniques described in further detail elsewhere herein. As an example, the volumes of the sample contained in the containers (e.g., in the cartridge 540) may be compiled and combined, such as in one container. The emulsion in this container may then be subjected to conditions sufficient to break the emulsion, merge or coalesce the droplets, and rejoin the contents of the droplets as an aqueous solution, which may also contain an oil phase thereon.

Emulsion breaking may comprise providing a system, such as a machine, or a device and/or a stimulus or combinations thereof to disrupt the droplets, such as by destabilizing them. The stimulus may comprise a chemical or a physical stimulus or combinations thereof. In some examples, the stimulus may be an antistatic force. In some examples, the methods and systems for emulsion breaking (e.g., third module 103 in FIG. 1) may comprise providing an electrical field. An emulsion to be broken may be subjected to the electrical field, such as by passing through the electrical field. The droplets may become electrically charged. The droplets may be static or dynamic. In some cases, droplets may be moving (e.g., rapidly in one or more directions, or randomly). Moving droplets may collide with one another and walls of the container, and may grow in size, such as by merging with one another. At some point, the droplet sizes may reach a threshold which may cause such droplets to settle.

Emulsion breaking may have various applications. In some examples, emulsion breaking may be used to recover a sample from an emulsion, which may be further processed or analyzed. For example, a sample comprising a nucleic acid molecule may be recovered using emulsion breaking after being amplified by an ePCR, such as the reactions and processes provided herein. In some examples, the methods may be performed to recover a plurality of beads from the sample. In some cases, beads may be recovered at a yield of at least about 30%, 40%, 50%, 60%, 70%, 80%, 90%, 99%, or more. In some examples, the yield of bead recovery may be at most about 99%, 90%, 80%, 70%, 60%, 50%, 40%, or less.

Provided herein are methods and systems for emulsion breaking. The emulsion breaking methods provided herein may facilitate processing larger amounts of samples compared to existing methods or workflows. Samples may comprise molecular biology samples to be processed in a laboratory, such as a molecular biology lab or similar. In some cases, it may be suitable to perform emulsion breaking for larger amounts of samples compared to existing methods using instruments of a given size. For example, in some cases, it may not be suitable or appropriate to use extremely large instruments for this application. Methods and systems of the present disclosure may allow for performing emulsion breaking of large sample sizes in a reasonable size of instruments that may be available in molecular biology or other relevant labs.

In some example, an emulsion sample which may be subjected to emulsion breaking may comprise a volume of at least about 30 mL, 40 mL, 50 mL, 60 mL, 70 mL, 80 mL, 90 mL, 96 mL, 100 mL, 110 mL, 120 mL, 150 mL, 170 mL, 200 mL, or more. An example of such sample may be an amplified DNA product.

Figure 7:
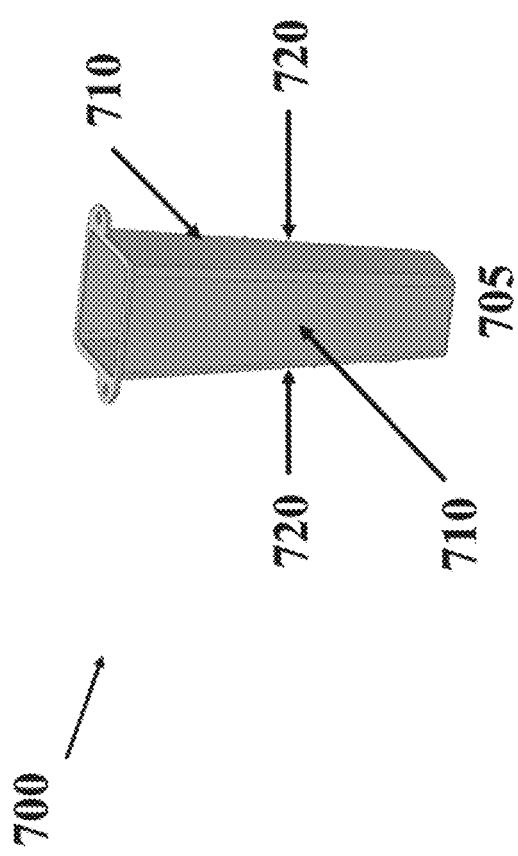
FIG. 7 shows an example container of the systems provided herein.

Emulsion breaking may be performed in a separate container from the reaction vessels provided for emulsion formation and/or emulsion processing (e.g., heat transfer), as described with respect to modules 101, 102 in FIG. 1, as illustrated in FIG. 7, or performed in the same reaction vessels provided for emulsion formation and/or emulsion processing (e.g., heat transfer). For example, for the former, the emulsion may be moved from the reaction vessels (e.g., in a cartridge) to a separate container (e.g., container 705 described elsewhere herein). Such movement can be facilitated by pipetting out, for example, or pouring from the reaction vessels into a separate container (e.g., container 705).

Referring to FIG. 7, the methods and systems for emulsion breaking (e.g., third module 103 in FIG. 1) may comprise a system 700. The system 700 may comprise a container, such as container 705, shown in FIG. 7. In some cases, the method may comprise breaking the emulsion and separating the sample from oil within the same container 705. Alternatively, more than one container may be used for same or various procedures. The sample may be separated from oil at once (in the same step in the same container 705). Alternatively, the methods may comprise more than one step, such as multiple steps, and the same or multiple container(s) may be used to carry on the method.

The method for emulsion breaking may be performed at a suitable temperature. The suitable temperature may vary in different applications. In some examples, the temperature may be set to at least about 25° C., 30° C., 40° C., 50° C., 60° C., 70° C., 80° C., 90° C., or more. In some examples, the temperature may be at most about 90° C., 80° C., 70° C., 60° C., 50° C., 40° C., 30° C., 25° C., or less. In some examples, the temperature may be below 25° C. depending on the application. In an example, the temperature may be about 60° C. In some examples, increasing the temperature of the emulsion to a given temperature, such as 60° C., may increase or accelerate the rate of droplet coalescence or droplet/emulsion breaking. For example, increasing the temperature of the container and/or sample may increasing the kinetic energy within the fluid which may increase the rate of droplet coalescence. The systems for emulsion breaking may comprise temperature control, such as a temperature control module. The temperature control system may be controlled by one or more processors or a computer system, such as the computer system 601 (shown in FIG. 6).

Provided herein is a system (e.g., 700 or 800), comprising a container (e.g., container 705 and 840). In some examples, the container may have a volume of at most 1 liter (L). Alternatively, the container may have other volumes listed elsewhere herein. The container may comprise a first surface (e.g., surface 850) and a second surface (e.g., surface 860) which may be substantially opposite from the first surface. In some cases, the container may further comprise a third surface and a fourth surface different from the first surface and the second surface. As an example, FIG. 7 shows a 3D schematic of a container 705 which contains a first surface, a second surface, a third surface, and a fourth surface (surfaces not labeled in FIG. 7).

The system may further comprise a first electrostatic block which may be in electrical communication with the first surface. The first electrostatic block may comprise one or more first electrodes (e.g., electrodes 820). The system may further comprise a second electrostatic block. The second electrostatic block may be in electrical communication with the second surface (e.g., surface 860). The second electrostatic block may comprise one or more second electrodes (e.g., electrodes 830). Alternatively or in addition to the electric block(s), the system may further comprise one or more thermal block(s) in thermal communication with the container, such as with one or more surfaces of the container. The system may further comprise a controller which may be operatively coupled to the first electrostatic block, the second electrostatic block, and/or the thermal block. The controller may be configured to: (i) activate the first electrostatic block and the second electrostatic block (e.g., simultaneously) to subject an electrode of the first electrostatic block or the second electrostatic block to alternate between positive and neutralizing ion at a predetermined frequency and/or (ii) using the thermal block, change or maintain a temperature of a content (e.g., sample 810) of the container at a predetermined temperature or temperature range. In some examples, the system may be used to break an emulsion or merge a plurality of droplets in the sample. In some examples, the predetermined temperature may be at least about 30° C., 40° C., 50° C., 60° C., 70° C., 80° C., 90° C., or more. In an example, the predetermined temperature may be from about 75° C. to 95° C. In an example, the predetermined temperature may be about 80° C. In another example, the predetermined temperature may be about 90° C.

Figure 8:
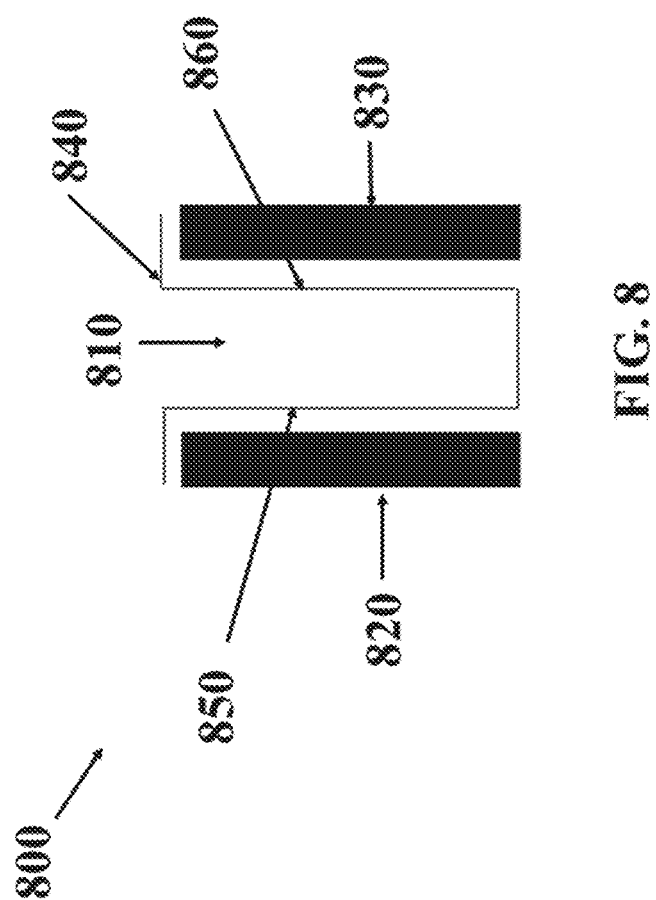
FIG. 8 shows an example system comprising a container and one or more electrostatic blocks.

Referring to FIGS. 7 and 8, system (700 or 800) may be used for emulsion breaking. The system may comprise a container, such as an emulsion breaking container (705 or 840). The container may be of any kind, shape, or form. The container may be, for example, similar to the container 705 shown in FIG. 7. Alternatively, the container may be similar to any container, reaction vessel, tube, or other kind of container provided anywhere herein. A sample 810 may be contained in the container (e.g., 705 or 840). The sample 810 may comprise an emulsion which may have gone through processing through first module 101 to second module 102 (shown in FIG. 1). For example, the sample may have been subjected to thermal processing using a system similar to the heat exchange system 500 shown in FIGS. 5A to 5D. The sample may further be subjected to emulsion breaking in the third module 103 (referring to FIG. 1).

The method of emulsion breaking may comprise providing an antistatic force 710, for example using the one or more first electrodes (e.g., electrodes 820) and/or the one or more second electrodes (e.g., electrodes 830). The force may be applied at any direction in any angle relative to the container (e.g., container 705 or 840) or surfaces thereof (e.g., surface 850 or surface 860). The electrodes (e.g., 820 and 830) may apply electrostatic forces to the sample (e.g., sample 810) from the sides of the container. Alternatively, the electrodes and the container may have any other configuration, angle, and setting.

The electrodes of the electrostatic blocks, such as the first one or more electrodes (e.g., electrodes 820) and the second one or more electrodes (e.g., electrodes 830) may be any kind of electrodes of any size, shape, form, configuration in the system, power, characteristics, etc. In an example, the one or more electrodes may comprise at least 1, 2, 3, 4, 5, 6, 7, 8, 9, 10, 11, 12, 13, 14, 15, 16, 17, 18, 19, 20, or more electrodes. In an example, the system may comprise 2 electrostatic blocks, each containing 12 electrodes. The electrodes may comprise various configurations, such as relative to each other, or the location and/or position of each electrode with respect to other electrodes, the container (e.g., container 705), and the rest of the system (e.g., system 700 or 800). In an example, one or more electrodes 820 are located on or adjacent to one face of the container (705 or 840), and one or more electrodes 830 are located on or adjacent to another face of the container which may be opposing the face of the container the other set of electrodes 820 are located. The electrodes 820 and the electrodes 830 may provide conditions sufficient to spread the ions of the solution on or adjacent to the two faces of the container 705. This may facilitate droplet coalescence and/or merging, which may result in breaking the solution.

In an example configuration, the system may comprise two electrostatic blocks. Each electrostatic block may comprise one or more electrodes (e.g., electrodes 820 and 830). the one or more electrodes may comprise at least 1, 2, 3, 4, 5, 6, 7, 8, 9, 10, 11, 12, 13, 14, 15, 16, 17, 18, 19, 20, or more electrodes. In an example, each electrostatic block may comprise 12 electrodes. The electrodes may be positioned next two each other. The configuration may comprise a defined spacing between each two adjacent electrodes. The spacing between two example electrodes may be at least about 0.1 inch, 0.15 inch, 0.2 inch, 0.25 inch, 0.3 inch, 0.35 inch, 0.375 inch, 0.38 inch, 0.39 inch, 0.4 inch, or more. In some examples, the spacing between two example electrodes may be at most about 2 inch, 1.5 inch, 1 inch, 0.9 inch, 0.8 inch, 0.7 inch, 0.6 inch, 0.5 inch, 0.4 inch, 0.38 inch, 0.35 inch, 0.3 inch, 0.2 inch, 0.1 inch, or less. In some example, the spacing between each two adjacent electrodes may be substantially zero.

The electrodes may alternate between a positive and neutralizing ion at a defined frequency. The frequency may be at least about 10 Hz, 20 Hz, 30 Hz, 40 Hz, 50 Hz, 60 Hz, 70 Hz, 80 Hz, 90 Hz, 100 Hz, 150 Hz, 200 Hz, 250 Hz, 300 Hz, or more.

The electrodes may provide electrostatic forces which may charge the aqueous droplets and promote coalescence of the droplets, such as by overcoming the surface tension forces promoted by surfactants in the solution. The droplets to be broken may have been formed using one or more reagents. For example, a droplet may comprise an aqueous sample compartmentalized in an oil immiscible with the aqueous phase, which may further comprise a surfactant. The surfactant may comprise specific chemistry and characteristics and may be used at suitable amounts in the oil depending on the application. The characteristics and amounts of the surfactant used may affect the stability level of the droplets, and subsequently the methods and systems for breaking such droplets. The methods for emulsion breaking may comprise providing and applying a force, such as an electrostatic force with suitable characteristics based on the characteristics of the droplets. The electrostatic force may be configured to overcome the force of the surfactant which may be keeping the droplets stable, and thereby coalesce the droplets.

Alternatively or in addition to the electrostatic force generation/manipulation system comprising the electrostatic block(s), the emulsion breaking system (700 or 800) may further comprise one or more temperature control equipment, such as a heater, a cooler, a heat exchanger, channels for fluid flow, a thermostat, or other tools or equipment for heating the sample, or any combinations thereof. In an example, a container, such as container 705 (also referred to as the emulsion breaking container herein) may comprise or be attached to one or more tools for temperature control, such as one or more heaters 720. In some cases, the heaters 720 may be used to increase the temperature of the sample to a suitable temperature for emulsion breaking. In some examples, the suitable temperature is about 60° C. In some examples, the suitable temperature is about 80° C. In other examples, other methods of temperature control may be used to adjust the temperature of the sample to a temperature suitable for performing the methods.

The method of emulsion breaking may further comprise providing and/or using given reagents or chemicals, such as buffers, ions, or other reagents. In some cases, ions may be used to help neutralize the charge of the sample or droplets. For example, a reagent, such as an ion may be added to the sample to accelerate droplet coalescence.

Also provided herein are systems and methods for performing emulsion breaking in absence of moving the emulsion to a separate container subsequent to emulsion formation and/or emulsion processing (e.g., thermocycling). For example, emulsion breaking may be performed while the emulsions are still contained in the reaction vessels in a cartridge (e.g., cartridge 540). In this case, subsequent to thermocycling, the cartridge instead of the separate container may be subjected to electrostatic and/or heating stimuli, as described elsewhere herein. For example, one or more electrostatic blocks and/or temperature blocks may be contacted or otherwise operably connected to the cartridge to effect the emulsion breaking. In some cases only electrostatic stimuli is applied. In some cases, only heating stimuli is applied. In some cases, a combination of electrostatic and heating stimuli is applied. In another example workflow, the contents of the cartridge may be subjected to heating, such as at or above about 100° C., to cause evaporation of the aqueous phase in the emulsion. A ceiling may be provided above the cartridge to provide a surface for condensation of such evaporated aqueous phase. The ceiling may be a foil material ceiling, for example. It will be appreciated that the cartridge may be subjected to any temperature or temperature range sufficient to cause evaporation. It will be appreciated that the ceiling may comprise any material sufficient to capture or cause condensation. In some cases, a temperature or temperature range of the ceiling may be changed or maintained to facilitate the condensation (e.g., such as by a thermal block or any other heating or cooling mechanism described herein). Upon condensation, the contents of the aqueous phase may rain down (via gravity) into the cartridge, such that the emulsions are successfully broken, with the contents of the emulsions being still contained within the cartridge.

Accordingly, provided herein is an integrated method for performing sample preparation and emulsion breaking in a same cartridge (or reaction vessel thereof). Emulsion formation, thermocycling, and emulsion breaking may be performed within the same cartridge in absence of removing a sample from the cartridge after initial input (for sample preparation). Such integration may help prevent sample loss and other reagent/product loss (e.g., bead loss) that can be caused by movement of the sample mixture between different reaction environments. A method may comprise (a) providing a sample in a reaction vessel in a cartridge, according to methods described herein, (b) forming an emulsion comprising a droplet comprising a nucleic acid molecule of the sample and a bead in the reaction vessel in the cartridge, according to methods described herein, and (c) breaking the droplet in the reaction vessel in the cartridge, according to the methods described herein.

Referring to FIG. 1, the fourth module 104 of the one or more modules may comprise methods and systems for sample handling or processing. In some examples, sample handling may comprise further processing of a sample which has gone through an ePCR and optionally, further emulsion breaking after the ePCR. Sample handling may comprise separating or otherwise manipulating the sample or components thereof to reach defined goals, such as a suitable sample composition or purity. For example, separating an oil from a sample comprising an aqueous and an oil phase. In some cases, sample handling or processing may be done to enrich a sample with a given component thereof, for example, a plurality of beads in the sample which in some cases, may have been processed by ePCR or another reaction (e.g., through modules 101, 102, and 103 shown in FIG. 1). Sample handling may comprise spinning the sample at various speeds for various durations using any spinning device (e.g., a centrifuge).

The methods and systems provided herein may comprise methods, systems, and procedures for sample processing. Sample processing may comprise a number of modules, procedures, and/or workflows. In some cases, samples may be subjected to PCR (ePCR), and later be subjected to an example workflow for separation of certain components from the sample, such as purifying or enriching the sample, or a component of the sample. In some examples, the samples may comprise a bead or a plurality of beads. Beads may be subjected to amplification using the methods and systems provided herein. The sample may be further processed to enrich the beads in the sample, such as by removing extra liquid or oil from the sample, by subjecting the sample to one or more washing and/or centrifugation procedures or protocols. In some cases, the total volume of the sample may be reduced during or after such procedures or workflows. Therefore, a concentration of a remaining component in the sample, such as beads or other constituents in the sample may increase or be enriched. The methods may comprise providing and/or using systems comprising a centrifuge, liquid handling device, such as a hand-held liquid handling device, a pipette, a robotic liquid handling system, a manual or automated liquid handling device or system, or any combination thereof.

The fourth module 104 may comprise a centrifuge. The fourth module 104, may further comprise or be coupled to a liquid handling module (e.g., a robotic liquid handler) For example, the third module 103 may comprise breaking, merging or coalescing a plurality of droplets resulting in two immiscible liquid phases (e.g., the aqueous sample and the oil), which may be on top of each other. For example, the oil phase may be on top of the aqueous phase. In such example, the fourth module 104, may comprise separating the oil from the sample. Following emulsion breaking using the third module 103, the fourth module 104 may comprise removing the oil phase, in part or in whole. For example, at least about 60%, 70%, 80%, 90%, 95%, 99%, or more of the oil may be removed from the container. In some example, oil may be removed from the container in one or more steps or one more rounds (e.g., repetitive rounds) of the one or more steps. In some cases, a pipette may be used the remove the oil and/or add a liquid to the sample or pellet. Alternatively, a liquid handling system (manual or automatic), such as a robotic liquid handling system (e.g., comprising pipettes or needles) may be used to pull up the oil. In some cases, one or more reagents may further aid removing oil, such as residual oil from the sample.

In some examples, after partial or complete oil removal from a sample contained in a container (e.g., container 705 or 840), the remaining contents of the container may comprise about 10 mL to 30 mL, 15 mL to 15 mL, or 16 mL to 20 mL of aqueous solution, or any other amounts of the solution. The sample may be divided into more than one portion, such as 2 portions, 3 portions, 4 portions, 5 portions, 6 portions, or more. In a particular example, approximately 16 ml to 20 ml of aqueous sample may remain in the container which may be subsequently divided into 4 portions and distributed into a plurality of containers (e.g., in this example, 4 containers). The containers may be wells or tubes, such as any container, reaction vessel, well, chamber or tube provided herein. In an example, containers may be centrifuge tubes. Containers may further comprise additional reagents such as a buffer. The reagents or buffer may further comprise a surfactant in a suitable amount based on the application. The reagents, such as a buffer comprising a surfactant may be configured to further remove potential remaining oil, such as residual oil, from the sample. The container may further be subjected to centrifugation to separate the residual oil. During or after centrifugation, the residual oil may be further separated from the sample using a liquid handling apparatus, device, or system, such as a pipette, robotic liquid handling system, or other system. These steps may be repeated. For example, more sample may be processed through modules 101, 102, and 103 and may be further added to the same or different containers including oil-free samples from the previous step (or round). The steps may be repeated a number of times, such as once, twice, 3 times, 4 times, 5 times, 6 times, or more, until a given amount of sample is processed. For example, at least about 10 mL, 20 mL, 30 mL, 50 mL, 60 mL, 70 mL, 90 mL, 100 mL, 120 mL, 130 mL, 140 mL, 150 mL, 170 mL, 200 mL, 210 mL, 220 mL, 250 mL, 300 mL or more volumes of the sample may be processed, such as through modules 101, 102, 103, and 104 shown in FIG. 1 and using the example system shown in FIGS. 5A-5D.

An emulsion may comprise an oil phase and an aqueous phase. The oil phase may comprise a surfactant or emulsifier. In some cases, the oil may comprise at least about 1%, 2%, 3%, 4%, 5%, 6%, 7%, 8%, 9%, 10%, 12%, 15%, 20%, or more emulsifier. Oil and emulsifier chemistries may be similar to chemistries and compositions disclosed in U.S. Pat. Nos. 8,715,934, 9,260,751, International Patent Application Publication No. WO2007149432, U.S. Pat. No. 9,803,226, International Patent Application Publication No. WO2014068407, European Patent No. EP2912196, U.S. Pat. Nos. 8,715,934, 9,260,751, and 9,803,226 each of which is incorporated by reference herein in its entirety for all purposes.

Figure 9:
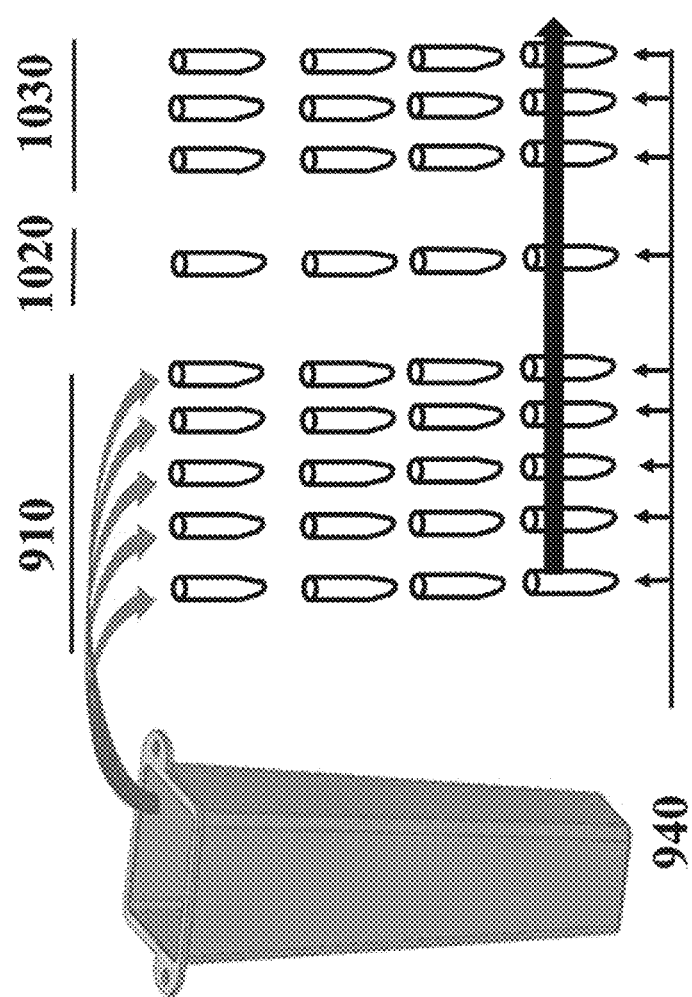
FIG. 9 shows an example method of sample processing provided herein.

An example of such workflow is shown in FIG. 9. For example, a sample may go through modules 101, 102, 103, shown in FIG. 1. Emulsions may be formed in the sample, sample comprising the emulsion may be subjected to thermal cycling using heat exchange system 500 or any other system, an ePCR may be performed on the sample (such as to amplify a plurality of beads), the sample may comprise beads among other reagents, materials, analytes, etc. The sample may be further subjected to emulsion breaking. Droplets in the sample may be coalesced, and the contents of the droplets may be merged as a liquid phase. The container (e.g., container 705) may contain the sample. Sample may be moved from container 705 or another container to one or more tubes (e.g., procedure 910 shown in FIG. 9). In an example, the sample may be moved from the emulsion breaking container 705 to a tube 940. In this example, the same tube 940 may be used in the rest of the workflow illustrated in FIG. 9. In this example and figure, the same tube is used to conduct a plurality of steps for further processing the sample. Procedure 910 may comprise moving the sample from container 705 to tube 940. The tube 940 may be centrifuged resulting in a pellet and a supernatant. The pellet may be substantially solid or semi-solid. The supernatant may be substantially liquid. In some cases, the supernatant may comprise some solid materials in it. The supernatant may be removed from the tube (e.g., procedure 910), such as after centrifugation and phase separation (solid from liquid), leaving behind the pellet. A first surfactant may be added to the pellet. More aqueous sample may further be added to the pellet. The pellet may be resuspended in the added liquids using any liquid handling device (pipette, hand-held device, robotic device comprising needles or any other kind of device). The centrifugation and removal of supernatant may be repeated for e second time. A second surfactant may be added to the pellet this time. Each of the steps in this workflow may be repeated for a suitable number of times, such as once, twice, 3 times, 4 times, 5 times, or more. For example, this workflow may be used to purify the sample from a certain chemical. This workflow may be performed after removing residual oil from the container.

In some examples, a plurality of supports, such as beads may be used in the methods provided herein. Supports or beads may comprise any support or bead, such as beads provided anywhere herein. In some examples, beads may comprise magnetic beads. In some cases, magnetic beads may be configured to be separated from the sample using magnetic or electromagnetic forces. Such magnetic separation may be further comprised in the workflows, methods, and protocols provided herein.

Figure 10:
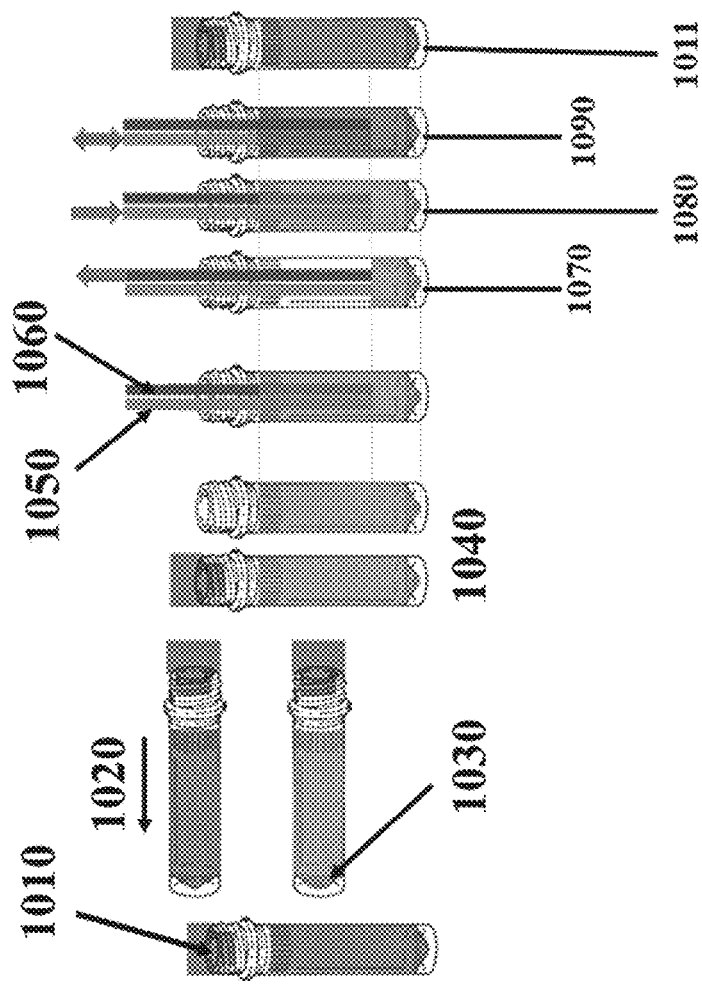
FIG. 10 shows an example method of sample processing provided herein.

FIG. 10 further illustrates an example of a method for further processing a sample. The tube (e.g., tube 940, such as a centrifuge tube) may comprise a cap or lid 1010 or tube hat. In some examples, the tube may comprise a sample, which may be a homogenous sample. For example, the sample may comprise a homogenous solution of beads. Alternatively, the sample may be non-homogenous. Beads may have been subjected to and processed by ePCR (e.g., using the methods and systems provided herein). The tube may be centrifuged 1020 at a defined rate. The beads may form a pellet 1030. The tube cap or tube hat (e.g., lid 1010) may be removed 1040 to allow the sample to be accessed by a device, apparatus, or system.

A liquid handling system may be used to further process the sample. The liquid handling system may be manual or automatic. The liquid handling system may comprise a robot or be robotic. The liquid handling system may be controlled by a computer system or one or more processors. The liquid handling system may comprise one or more tube grippers, one or more transfer needles, one or more dual needles, a waster chamber, liquid lines or pipes, processors, other mechanical and/or electrical parts, a power source, a control system, one or more processors, a computer system (e.g., computer system 601), hardware, software, and other parts. The liquid handling system may comprise one or more needles (e.g., 1050 and 1060). For example, two needles or a dual reagent needle may be inserted into the tube solution. The supernatant may be removed 1070. A fluid comprising suitable reagents and compositions (such as a buffer) may be dispensed. The liquid handling system may provide or facilitate mixing 1090 in the tube, such as using the needles and/or other parts, for example, by moving the liquid in a vertical direction. The cap or hat may be installed 1011. The steps may be repeated for one or more rounds, such as 1, 2, 3, 4, 5, 6, 7, 8, 9. 10, or more rounds until a suitable or defined state or characteristic is reached in the sample.

The present disclosure provides a method of sample processing. The method may comprise providing a thermocycler comprising a plurality of fins and a fluid channel in thermal communication with the plurality of fins. The method may further comprise providing a first fluid source container. The first fluid source container may be configured to maintain fluid within at a first temperature or temperature range. The method may further comprise providing a second fluid source container. The second fluid source container may be configured to maintain fluid within at a second temperature or temperature range which may be different from the first temperature or temperature range.

In some examples, the fluid channel may be fluidically connected to the first fluid container and the second fluid container. The method may further comprise receiving a cartridge which may comprise a plurality of containers between at least a subset of the plurality of fins in the thermocycler. In some examples, a container of the plurality of containers may comprise a sample. The method may comprise thermocycling the sample by subjecting a gap between the at least the subset of the plurality of fins and the plurality of containers to negative pressure, thereby creating a vacuum to decrease a distance or width of the gap. A cartridge may comprise or be a plate.

The method may further comprise subjecting fluid from the first fluid source container and the second fluid source container, in sequence, to flow through the fluid channel.

In some examples, the method may further comprise subjecting the sample to washing in a washing module which may be operably coupled to the thermocycler. In some examples, the method may further comprise (e.g., prior to the washing), receiving a second cartridge in the thermocycler. In some examples, the second cartridge may comprise a second sample. In some examples, the method may further comprise (e.g., during the washing of the sample in the washing module), subjecting the second sample to thermocycling in the thermocycler.

In some examples, the method may further comprise, subsequent to washing of the sample, subjecting the sample to enrichment in an enrichment module operably coupled to the washing module. In some examples, the method may further comprise (e.g., prior to the enrichment) receiving a third cartridge on the thermocycler. The third cartridge may comprise a third sample. In some examples, the method may further comprise (e.g., during the enrichment of the sample), subjecting the third sample to thermocycling. In some examples, the method may further comprise (e.g., subsequent to the washing), subjecting the sample to enrichment in an enrichment module operably coupled to the washing module.

In some examples, the method may further comprise (e.g., prior to the enrichment), receiving a second cartridge or plate on the thermocycler. The second cartridge may comprise a second sample. In some examples, the method may further comprise (e.g., during the enrichment of the sample) subjecting the second sample to thermocycling. In some examples, the method may further comprise (e.g., subsequent to the washing), incubating the sample at a predetermined temperature or a range thereof. In some examples, the method may further comprise (e.g., subsequent to the incubating), subjecting the sample to enrichment in an enrichment module.

In some examples, the method may further comprise (e.g., subsequent to thermocycling), subjecting the sample to sequencing. In some examples, the method may further comprise loading the cartridge by an operator. In some examples, receiving the cartridge in the thermocycler may be automated.

In some cases, the method may comprise a number of operations such as one or more of loading a plate or cartridge comprising a sample on the system, thermal cycling, washing (e.g., bead cleanup), incubation at a predefined temperature, enrichment, sequencing, and more. A few examples of various workflows, configurations, such as example orders at which various operations can be performed are provided in FIGS. 11-16.

Figure 11:
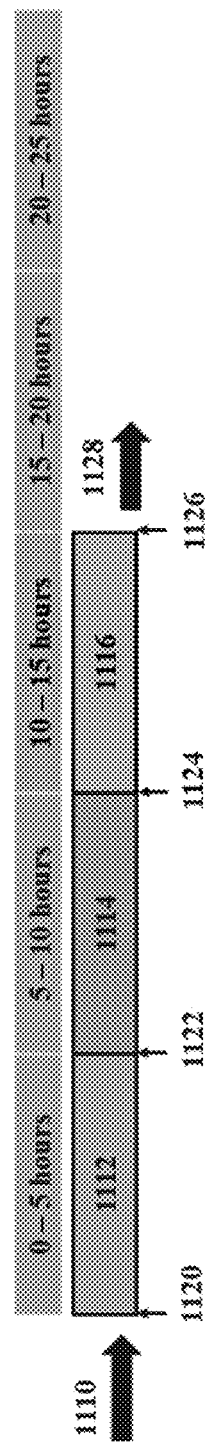
FIG. 11 shows an example serial operation workflow according to the methods of the present disclosure.
Figure 12:
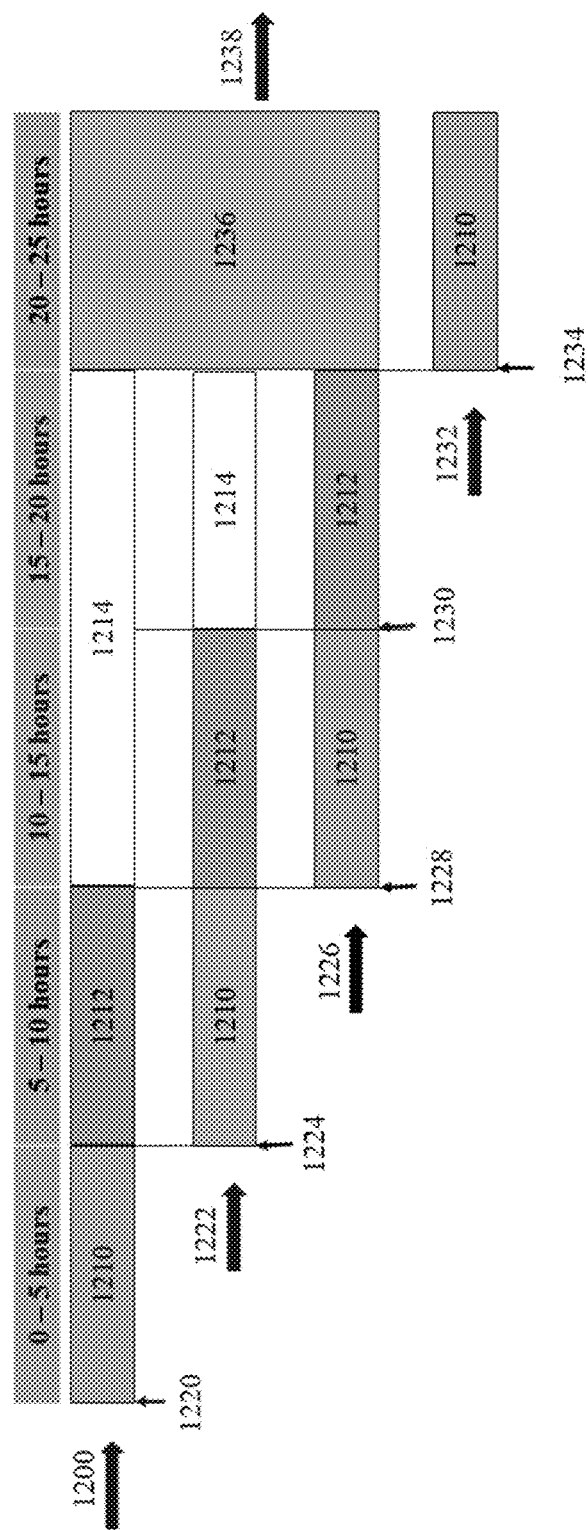
FIGS. 12-16 show examples of parallel processing workflow for performing the methods of the present disclosure.

For example, the method may comprise a continuous batch operation. FIGS. 11 and 12 provide two example workflows that may be used for performing the methods of the present disclosure. FIG. 11 shows an example of a serial operation. The serial operation may show the steps for preparing a sample for sequencing according to the methods and systems provided herein. In a serial operation, the first step may comprise loading the plate 1110. The plate may be any plate, such as the array plates comprising reaction vessels provided elsewhere herein. The plate may be loaded by a user, an automated system or robot at a given time, for example, at an initial stable pause point 1120. In an example, the sample may be provided in the cartridge of the systems provided herein by a user or a robotic and/or other automated system. The method may comprise thermal cycling 1112 for a given period (e.g., about 5 hours). During this step, the sample may be subjected to thermal cycling and PCR (e.g., in the heat exchange system), as described elsewhere herein. The operation or workflow may reach another stable pause point 1122 after a given time (e.g., after 5 hours from the beginning of the workflow as shown in this example). The given time may vary based on application and process. The given time may be at least about 10 minutes (min), 20 min, 30 min, 40 min, 50 min, 60 min (1 hour (hr)), 2 hr, 3 hr, 4 hr, 5 hr, 6 hr, 7 hr, 8 hr, 9 hr, 10 hr, or longer. Alternatively or in addition to, the given time may be at most about 10 minutes (min), 20 min, 30 min, 40 min, 50 min, 60 min (1 hour (hr)), 2 hr, 3 hr, 4 hr, 5 hr, 6 hr, 7 hr, 8 hr, 9 hr, 10 hr, or shorter. The second step in the process may comprise or be washing 1114 (such as bead cleanup of beads in the sample). The sample may be subject to washing in a washing module. For example, washing may comprise subjecting the sample to a washing solution or buffer. For example, in a washing module, the contents of the plurality of partitions (e.g., droplets of an emulsion) may be pooled (e.g., nucleic acid molecules and corresponding amplification products and beads may be released from droplets of a plurality of droplets in an emulsion). Upon release of a bead-nucleic acid molecule complex (or complexes) from the partition of the plurality of partitions, the bead-nucleic acid molecule complex (or complexes) may be separated (e.g., magnetically separated) from other materials (e.g., from the pooled contents of droplets of a plurality of droplets of an emulsion) by the end of, for example, 5 to 10 hours from the beginning of the workflow. At this stage, the process may reach another stable pause point 1124.

The sample may be further subjected to enrichment 1116. In some examples, enrichment may comprise generating or isolating a pre-assembled support (e.g., a bead), generally referred to herein as an assembly, wherein the assembly comprises a single template nucleic acid molecule immobilized to a single support. Enrichment may comprise isolating a subset of beads (e.g., positively amplified beads comprising amplified products coupled thereto) from a larger population of beads (e.g., mixture of positively amplified beads and negative beads which do not comprise amplified products coupled thereto). Enrichment may comprise isolating a population of beads form any mixture. Enrichment may be performed in an enrichment module.

Enrichment may be accomplished by the end of a given time, for example, 10-15 hours from the beginning of the workflow leading to another stable pause point 1126. The given time may vary based on the process and/or application. In some examples, after, for example 15-20 hours from the beginning of the workflow, the sample may be ready for sequencing 1128. In some examples, a nucleic acid molecule or any amplification products corresponding thereto or derivatives thereof of a partition of the plurality of partitions that may have formed by the methods described herein may be assayed or analyzed (e.g., by determining the nucleotide sequence in a sequencer).

In some examples, the systems provided herein may comprise one or more modules and may run continuously. For example, the process may be end-to-end integrated. For example, the user or an automated system or robot can start new batches on the front end and products (e.g., finished products) may come out the other end. For example, the user or automated system or robot may not need to wait for a sample to finish processing before they can load another sample. Multiple samples may run in parallel and continuously. Running samples in parallel and/or continuously may increase the throughput of the system compared to a serial operation and/or a system through which only one sample can be run at a time.

FIG. 12 shows an example workflow comprising parallel processing. One or more processes comprising steps identical or similar to the steps described in FIG. 11 may be performed in parallel. For example, at an initial pause point 1220, a user (e.g., an operator), a machine, and/or an automated and/or robotic system may load a cartridge or plate (e.g., plate 1). The sample may be subject to thermal cycling 1210, PCR, and washing 1212 (e.g., bead cleanup), the sample may be incubated at a predefined temperature or temperature range for a predefined period 1214. The sample may be incubated in an incubator module, a refrigerator, or any other module, such as the immediately preceding module. For example, the sample may be held at 4° C. (e.g., in a refrigerator kept at 4° C.) for a given incubation time which can vary depending on several factors. The sample may be held at any other temperature or temperature range. At another stable pause point 1224 (e.g., after 5-10 hours from the beginning of the process) the user or automated system may load another plate or cartridge (e.g., plate 2). The sample in plate 2, may undergo a process similar to that of plate 1. At other stable pause points, such as third 1228, fourth 1230, fifth 1234, sixth, or other pause points, more plates, such as 1, 2, 3, 4, 5, 6, 7, 8, 9, or more plates can be loaded and may undergo a similar process. In some cases, the samples from the cartridges or plates (e.g., all the samples from all plates may undergo enrichment 1236, in some cases, together at the same time). The samples may be ready for sequencing 1238 at the end of the process. The process shown in the example of FIG. 12 may have a higher throughput compared to the process of FIG. 11 due to continuous operation and/or parallelization.

In some examples, the processes of thermal cycling, washing, and enrichments may all be performed in parallel on a number of samples. Each sample may go through the process and be subjected to each procedure of the workflow (e.g., in sequence). For example, a sample may follow process 1200: be thermocycled 1210 during the first stage of a workflow starting at a first time, then proceed to be washed 1212, and next be enriched 1236. At the same time, the samples in another cartridge may be going through another one of the abovementioned processes (e.g., process 1222 starting with thermal cycling 1210 at a second and later time, then washing 1212, and then enriching 1236), and other samples in other cartridges may be processed through other different procedures in parallel (e.g., process 1226 starting with thermal cycling 1210 at a third and later time, then washing 1212, and then enriching 1236; and process 1232 starting with thermal cycling 1210 at a fourth and later time, and etc.). In one or more of the parallel processes, an incubating period 1214 may be added. Each cartridge may exit the workflow upon completion of all the procedures. Upon exiting the workflow, such sample may then be moved (manually and/or automatically) to a sequencer or sequencing module and be subjected to sequencing. Parallel processing may increase the throughput of the process.

Examples of parallel processing workflows are provided in FIGS. 13-16. For example, at any pause point (e.g., 1310, 1312, 1314, 1316), a cartridge may be loaded on the system such as described elsewhere herein. The cartridge and the samples therein may sequentially undergo processing through each of the mentioned procedures (e.g., thermal cycling 1210, washing 1212, and enrichment 1236, e.g., in sequence).

Figure 13:
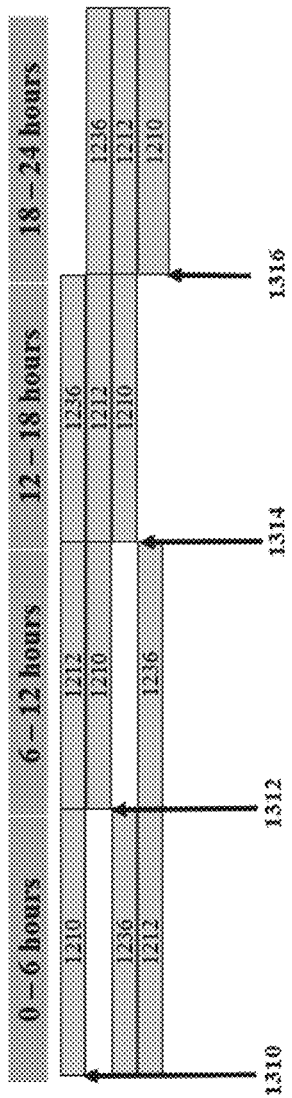

With reference to FIG. 13, at a first given time period (e.g., between pause points 1310 and 1312), in parallel, one or more cartridges or plates may be processing through thermal cycling 1210, while at the same time, one or more other cartridges are processing through washing 1212, and one or more other cartridges are processing through enrichment 1236. At a later time (e.g., pause point 1312), each cartridge may advance to the next procedure (e.g., thermal cycling 1210 to washing 1212, washing 1212 to enrichment 1236, enrichment 1236 to exit), while one or more new cartridges may be loaded on the system (e.g., for thermal cycling 1210) and go through the procedures in parallel. The cartridge that is being enriched (e.g., during the time between pause point 1312 and 1314) may be the cartridge that has gone through washing in the previous stage (e.g., during the time period between pause point 1310 and 1312), and thermocycling in the preceding stage. The above may be repeated for each pause point. For example, at pause point 1314, one or more new cartridges may be loaded (e.g., for thermal cycling 1210). The different cartridges may undergo enrichment 1236, washing 1212 and thermal cycling 1210 in parallel, for example until pause point 1316 is reached. At pause point 1316, one or more new cartridges may be loaded and may undergo a similar parallel process as the previous stages. Cartridges from one stage may undergo a different procedure in the next stage. Each sample may exit the workflow once it has completed all the stages. Such sample may then be ready for sequencing.

Figure 14:
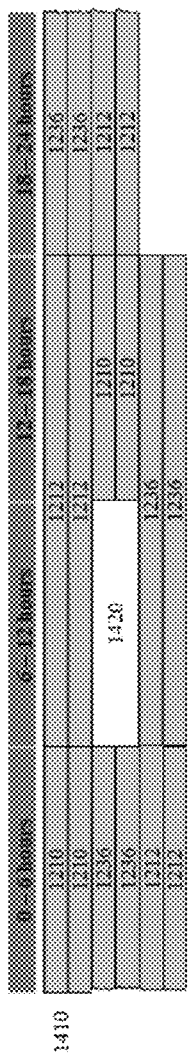

Another example workflow is shown in FIG. 14, where multiple cartridges are processed with the same operation in parallel. In this example, during the first stage (e.g., 0-6 hours from the beginning of the workflow on a given day), two cartridges may be loaded at point 1410 and undergo thermal cycling. In parallel, two cartridges which may have been previously thermocycled and washed may undergo enrichment 1236, and two cartridges which may have been previously thermocycled may undergo washing 1212. The cartridges thermocycled during the first stage (e.g., 0-6 hrs from the beginning of the workflow on the same day) may proceed to be processed in the next stage (e.g., 6-12 hrs from the beginning of the workflow). Such processing may comprise washing (e.g., bead cleanup) and/or other procedures. The cartridges that are being thermocycled during a given stage may have been loaded during the same and/or the previous stage of the workflow.

With continued reference to FIG. 14, the workflow may comprise a time window (e.g., time window 1420) for cartridge/plate and/or reagent loading (e.g., at this stage or any other stage during the workflow). The time window may begin at a pause point (e.g., 1310 1312, 1314, 1316 with reference to FIG. 13), and end at any other subsequent pause point, such as at the next immediate pause point, at the second pause point, at the third pause point, etc. For example, the time window may span one or more operation time blocks. In some cases, in parallel to the loading time window, one or more cartridges or plates (e.g., two cartridges or plates) may be enriched (e.g., 1236), and one or more other cartridges or plates may be washed (e.g., 1212). In this example, the time window 1420 is shown to be during the time period from about 6 hours after starting the workflow to about 12 hours from starting the workflow; however, many other possibilities for the duration and timing of the time window may be applied. The plates undergoing washing and enriching may remain in these same processes, while the time window for loading passes, and the loaded plates are thermocycled (e.g., 1210). At the next pause point, the plates that are thermally cycled (e.g., from about 12 to about 18 hours from the beginning of the workflow) may be moved to the next stage (e.g., washing), along with the plates that are enriched moving to the next stage (e.g., exiting) and the plates that are washed moving to the next stage (e.g., enrichment). In some examples, after the workflow (e.g., the workflow shown in FIG. 14) is completed, the samples processed and/or prepared in the workflow may be transferred (e.g., manually or automatically/robotically) to a sequencing module and/or system and be subjected to sequencing for example, to determine the sequence of the nucleic acid molecules in the samples. In some cases, the samples may further be incubated at a predefined temperature for a predefined period, for example, prior to sequencing. It will be appreciated that the workflow may comprise any type and any number of processes, that may be staggered (e.g., as in FIG. 11) and/or parallel (e.g., as in FIGS. 13-16). It will be appreciated that while FIG. 14 illustrates the parallel processing of two plates for each operation (e.g., thermocycling, washing, enrichment), any number of plates can be parallelly processed for each operation, as the system capacity allows. For example, at least 1, 2, 3, 4, 5, 6, 7, 8, 9, 10, 20 or more plates or cartridges may be parallelly processed for each operation.

Figure 15:
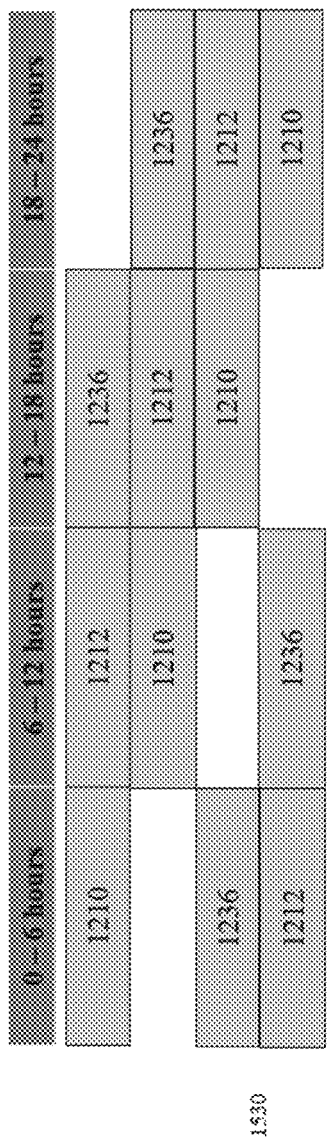

FIG. 15 shows another example workflow. In this example, one or more cartridges may be processed during the first stage of the workflow (e.g., the duration from about 0 to about 6 hours from the beginning of the workflow on a given day). The first stage of the workflow shown in FIG. 15 may comprise thermocycling 1210 the samples in one or more cartridges, enriching 1236 the samples in one or more other cartridges, and washing 1212 the samples in one or more other cartridges in parallel. In some cases, the samples that are subjected to enrichment and/or washing at this time may have been thermocycled at an earlier time 1530. The earlier time 1530 may comprise the previous round of the workflow.

Figure 16:
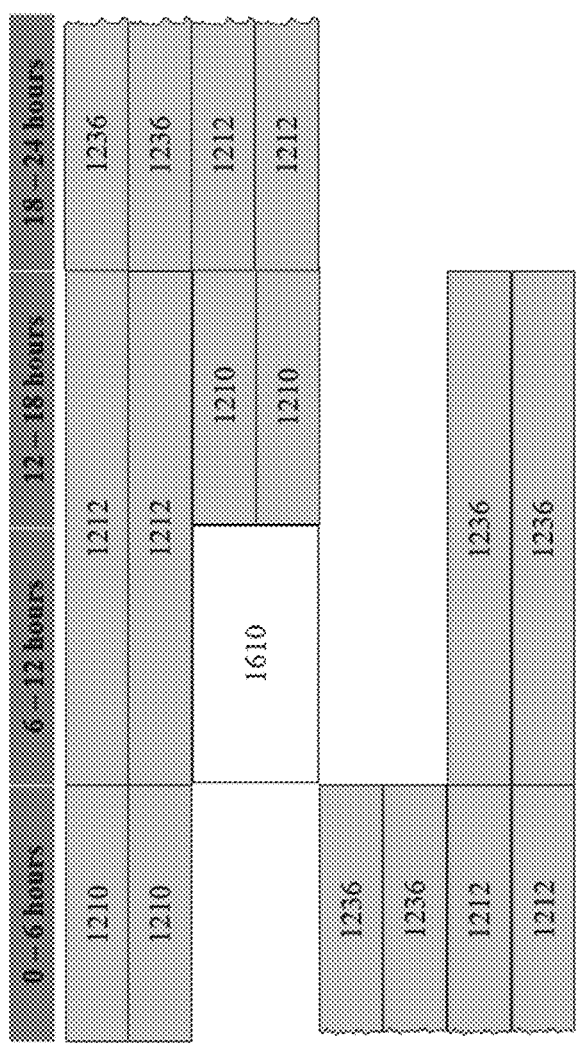

FIG. 16 shows another example of a parallel processing workflow for performing the methods of the present disclosure. The workflow shown in FIG. 16 may comprise four or more stages which may be completed in, for example, 24 hours or any other duration of time. As an example, the first stage may comprise any duration of time, for example, the duration of time from about 0 to about 6 hours from the beginning of the workflow. During the first stage, samples in one or more cartridges (e.g., two cartridges) may be subject to thermal cycling 1210, samples in one or more cartridges (e.g., two cartridges) may be subject to enrichment 1236, and samples in one or more other cartridges (e.g., two cartridges) may be subject to washing 1212 in parallel. The second stage may comprise a duration of time, such as the duration of time from 6 hours to 12 hours from the beginning of the workflow. The second stage or any other stage of the workflow may comprise a time window (e.g., time window 1610) during which cartridges and/or reagents may be loaded (e.g., by an operator and/or a robot). The third stage may comprise a duration of time from about 12 hours to about 18 hours from the beginning of the workflow. In some examples, during the second and third stages of the workflow, the samples of one or more (e.g., two) cartridges may be subjected to washing 1212. The samples being washed in this stage may have been thermocycled in the previous stage. In parallel, the samples of one or more (e.g., two) cartridges may be subjected to thermal cycling 1210. As an example, the samples being thermocycled 1210 in the third stage may have been loaded during the time window 1610 in the second stage. In parallel, the samples of one or more (e.g., two) cartridges may be enriched 1236 during the second and/or third stage of the workflow. In some cases, the samples enriched in this stage may have been washed in the previous stage. During the fourth stage (e.g., time period from about 18 to about 24 hours from the beginning of the workflow), the samples of one or more (e.g., two) cartridges may be enriched 1236, and the samples of one or more (e.g., two) cartridges may be washed 1212. The samples enriched during the fourth stage may have been washed during the third stage. The samples being washed during the fourth stage may have been thermocycled during the third stage. After 24 hours, the workflow may repeat on the next 24 hours. Samples that have been processed through the last stage of the workflow may exit the workflow (e.g., to be sequenced), for example if they have completed all stages of the process and are ready. In case the samples need further processing after 24 hours, they may be processed through the first stage of the workflow on the next 24 hours. Various other configurations and timings may be applied as appropriate.

Computer Control Systems

Figure 6:
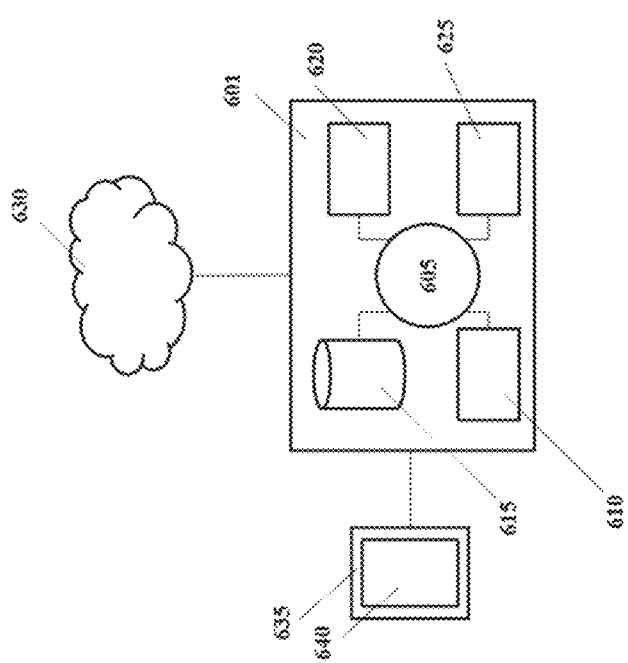
FIG. 6 shows a computer control system that is programmed or otherwise configured to implement methods provided herein.

The present disclosure provides computer control systems that are programmed to implement methods of the disclosure. FIG. 6 shows a computer system 601 that is programmed or otherwise configured to implement methods and systems of the present disclosure, such as performing nucleic acid sequence and sequence analysis.

The computer system 601 includes a central processing unit (CPU, also "processor" and "computer processor" herein) 605, which may be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 may be a data storage unit (or data repository) for storing data. The computer system 601 may be operatively coupled to a computer network ("network") 630 with the aid of the communication interface 620. The network 630 may be the Internet, an internet and/or extranet, or an intranet and/or extranet that is in communication with the Internet. The network 630 may be a telecommunication and/or data network. The network 630 may include one or more computer servers, which may enable distributed computing, such as cloud computing. The network 630, with the aid of the computer system 601, may implement a peer-to-peer network, which may enable devices coupled to the computer system 601 to behave as a client or a server.

The CPU 605 may execute a sequence of machine-readable instructions, which may be embodied in a program or software. The instructions may be stored in a memory location, such as the memory 610. The instructions may be directed to the CPU 605, which may subsequently program or otherwise configure the CPU 605 to implement methods of the present disclosure. Examples of operations performed by the CPU 605 may include fetch, decode, execute, and writeback.

The CPU 605 may be part of a circuit, such as an integrated circuit. One or more other components of the computer system 601 may be included in the circuit. The circuit may be an application specific integrated circuit (ASIC).

The storage unit 615 may store files, such as drivers, libraries and saved programs. The storage unit 615 may store user data, e.g., user preferences and user programs. The computer system 601 may include one or more additional data storage units that are external to the computer system

601, such as located on a remote server that is in communication with the computer system 601 through an intranet or the Internet.

The computer system 601 may communicate with one or more computer systems through the network 630. For instance, the computer system 601 may communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user may access the computer system 601 via the network 630.

Methods as described herein may be implemented by way of machine (e.g., computer processor) executable code stored on an electronic storage location of the computer system 601, such as, for example, on the memory 610 or electronic storage unit 615. The machine-executable or machine-readable code may be provided in the form of software. During use, the code may be executed by the processor 605. The code may be retrieved from the storage unit 615 and stored on the memory 610 for ready access by the processor 605. In some situations, the electronic storage unit 615 may be precluded, and machine-executable instructions are stored on memory 610.

The code may be pre-compiled and configured for use with a machine having a processor adapted to execute the code or may be compiled during runtime. The code may be supplied in a programming language that may be selected to enable the code to execute in a pre-compiled or as-compiled fashion.

Some of the systems and methods provided herein, such as the computer system 601, may be embodied in programming. Various aspects of the technology may be thought of as "products" or "articles of manufacture" typically in the form of machine (or processor) executable code and/or associated data that is carried on or embodied in a type of machine readable medium. Machine-executable code may be stored on an electronic storage unit, such as memory (e.g., read-only memory, random-access memory, flash memory) or a hard disk. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, such as a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 may include or be in communication with an electronic display 635 that comprises a user interface (UI) 640 for providing, for example, a state or condition of a module, compartment, or unit of the system, a process control scheme, measurements taken at various points of the process, such as a temperature, pressure, flow rate, a concentration of a compound, or other parameters. In some examples, the UI may display the results of nucleic acid sequence (e.g., sequence reads, consensus sequences, etc.). In some examples, the UI may display images of a sample at a given point during the process. Examples of UI's may comprise a graphical user interface (GUI) and web-based user interface.

Methods and systems of the present disclosure may be implemented by way of one or more algorithms. An algorithm may be implemented by way of software upon execution by the central processing unit 605. The algorithm can, for example, implement methods of the present disclosure.

It is intended that the following claims define the scope of the invention and that methods and structures within the scope of these claims and their equivalents be covered thereby.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system, comprising:
a container having a volume from 30 milliliters (mL) to 1 liter (L), wherein said container comprises a first surface, a second surface substantially opposite from said first surface, and a third surface connected with said first surface and said second surface, wherein said third surface is substantially perpendicular to said first surface and said second surface, wherein said container is configured to contain a solution comprising a plurality of droplets, wherein said solution is in contact with said first surface and said second surface;
one or more first electrodes in electrical communication with said first surface and located adjacent to said first surface;
one or more second electrodes in electrical communication with said second surface and located adjacent to said second surface;
a heat exchange system in thermal communication with said third surface; and
a controller operatively coupled to said one or more first electrodes, said one or more second electrodes, and said heat exchange system, wherein said controller is configured to: simultaneously (i) activate said one or more first electrodes and said one or more second electrodes to alternate between positive and neutralizing ions at a predetermined frequency, and (ii) using said heat exchange system, change or maintain a temperature of said solution at a predetermined temperature or temperature range, wherein said predetermined frequency and/or said predetermined temperature or temperature range are sufficient to merge or coalesce said plurality of droplets in said container.

2. The system of claim 1, wherein said container has a volume of at most 500 milliliters (mL).

3. The system of claim 2, wherein said container has a volume of at most 300 mL.

4. The system of claim 1, wherein said predetermined frequency is at least 30 Hertz (Hz).

5. The system of claim 4, wherein said predetermined frequency is at least 50 Hz.

6. The system of claim 1, wherein said predetermined temperature or temperature range is at least 30 degrees Celsius (° C.).

7. The system of claim 6, wherein said predetermined temperature or temperature range is at least 50 degrees Celsius (° C.).

8. The system of claim 7, wherein said predetermined temperature or temperature range is at least 60 degrees Celsius (° C.).

9. The system of claim 1, wherein said one or more first electrodes comprises at least 5 electrodes.

10. The system of claim 9, wherein said one or more first electrodes comprises at least 10 electrodes.

11. The system of claim 10, wherein said one or more first electrodes comprises at least 12 electrodes.

12. The system of claim 1, wherein at least two of said one or more first electrodes are spaced at least ⅛ inch apart.

13. The system of claim 12, wherein at least two of said one or more first electrodes are spaced at least ⅜ inch apart.

14. The system of claim 1, wherein said container has a third surface and a fourth surface different from said first surface and said second surface, wherein said third surface is substantially opposite from said fourth surface, and wherein said heat exchange system is in thermal communication with said third surface or said fourth surface.

15. The system of claim 14, further comprising a second heat exchange system in thermal communication with said third surface, and wherein said heat exchange system is in thermal communication with said fourth surface.

16. The system of claim 1, wherein said predetermined frequency and said predetermined temperature or temperature range are sufficient to merge or coalesce said plurality of droplets in said container.

17. The system of claim 1, wherein said one or more first electrodes and said one or more second electrodes are located outside of said container.

18. The system of claim 1, wherein said first surface and said second surface are separated by said third surface and a fourth surface of said container, wherein said fourth surface is substantially opposite from said third surface and is substantially perpendicular to said first surface and to said second surface.

* * * * *